(12) United States Patent
Chianelli et al.

(10) Patent No.: US 8,278,452 B2
(45) Date of Patent: Oct. 2, 2012

(54) HETEROCYCLIC COMPOUNDS AND COMPOSITIONS AS C-KIT AND PDGFR KINASE INHIBITORS

(75) Inventors: Donatella Chianelli, San Diego, CA (US); Xiaolin Li, San Diego, CA (US); Xiaodong Liu, San Diego, CA (US); Jon Loren, San Diego, CA (US); Valentina Molteni, San Diego, CA (US); Juliet Nabakka, San Diego, CA (US); Vince Yeh, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 12/918,801

(22) PCT Filed: Feb. 20, 2009

(86) PCT No.: PCT/US2009/034778
§ 371 (c)(1),
(2), (4) Date: Feb. 18, 2011

(87) PCT Pub. No.: WO2009/105712
PCT Pub. Date: Aug. 27, 2009

(65) Prior Publication Data
US 2011/0183997 A1    Jul. 28, 2011

Related U.S. Application Data

(60) Provisional application No. 61/030,912, filed on Feb. 22, 2008.

(51) Int. Cl.
*C07D 471/02* (2006.01)
(52) U.S. Cl. .................................................. 546/122
(58) Field of Classification Search .................. 546/123, 546/122; 514/300
See application file for complete search history.

(56) References Cited

U.S. PATENT DOCUMENTS

| 6,172,079 B1 | 1/2001 | Ohno et al. |
| 2004/0019210 A1 | 1/2004 | Chivikas et al. |
| 2007/0054916 A1 | 3/2007 | Patel et al. |

FOREIGN PATENT DOCUMENTS

| WO | WO9909030 | 2/1999 |
| WO | WO03066630 | 8/2003 |
| WO | WO2006052936 | 5/2006 |
| WO | WO2007021795 | 2/2007 |
| WO | WO2005034869 | 4/2007 |
| WO | WO2007038669 | 4/2007 |
| WO | WO2007136465 | 11/2007 |
| WO | WO2008034008 | 3/2008 |
| WO | WO2008051757 | 5/2008 |
| WO | WO2008137605 | 11/2008 |
| WO | WO2008137794 | 11/2008 |

*Primary Examiner* — Nizal Chandrakumar
(74) *Attorney, Agent, or Firm* — Daniel E. Raymond; Genomics Institute of the Novartis Research Foundation

(57) ABSTRACT

The invention provides a novel class of compounds of Formula I: (I) pharmaceutical compositions comprising such compounds to treat or prevent diseases or disorders associated with abnormal or deregulated kinase activity, particularly diseases or disorders that involve abnormal activation of c-kit, PDGFRα and PDGFRβ kinases.

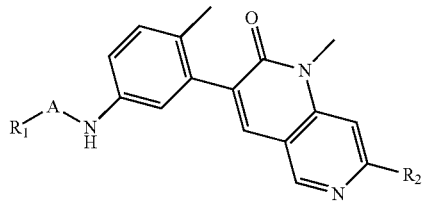

(I)

14 Claims, No Drawings

HETEROCYCLIC COMPOUNDS AND COMPOSITIONS AS C-KIT AND PDGFR KINASE INHIBITORS

CROSS-REFERENCE TO RELATED APPLICATION

This application is a 371 U.S. national phase application of international application number PCT/US2009/034778 filed 20 Feb. 2009, which claims priority to U.S. provisional patent application No. 61/030,912, filed 22 Feb. 2008. The full disclosure of these applications is incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of c-kit, PDGFRα and PDGFRβ kinases.

2. Background

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the nerve growth factor receptor, trkB, and the fibroblast growth factor receptor, FGFR3, B-RAF; non-receptor tyrosine kinases such Abl and the fusion kinase BCR-Abl, Lck, Bmx and c-src; and serine/threonine kinases such as c-RAF, sgk, MAP kinases (e.g., MKK4, MKK6, etc.) and SAPK2α and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

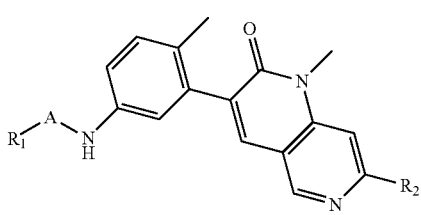

in which:

$R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, =N(OH), $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1NR_{3a}R_{3b}$, —$X_1C(O)R_{3a}$, —$X_1C(O)OR_{3a}$, —$X_1OR_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein $R_{3a}$ and $R_{3b}$ are independently selected from hydrogen and $C_{1-6}$alkyl; $R_2$ is selected from methyl and ethyl;

A is an unsaturated 5 member ring containing 2 or 3 heteroatoms or groups selected from =N—, —$NR_4$—, —O— and —$S(O)_{0-2}$—; wherein $R_4$ is selected from hydrogen, $C_{1-4}$alkyl and $C_{3-8}$cycloalkyl; wherein said $C_{1-4}$alkyl or $C_{3-8}$cycloalkyl of $R_4$ can have a methylene replaced with a heteroatom selected from O, $S(O)_{0-2}$ and $NR_{30}$; wherein $R_{30}$ is selected from hydrogen and $C_{1-4}$alkyl; wherein A can be optionally substituted with $C_{1-2}$alkyl; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly c-kit, PDGFRα and/or PDGFRβ activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly c-kit, PDGFRα and/or PDGFRβ activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, $C_{6-10}$aryl as used in this application, includes but is not limited to phenyl or naphthyl, preferably phenyl. "Arylene" means a divalent radical derived from an aryl group.

"Heteroaryl" is a 5 to 15 member, unsaturated ring system containing 1 to 3 heteroatoms independently selected from —O—, —N=, —NR—, —C(O)—, —S—, —S(O)— or —$S(O)_2$—, wherein R is hydrogen, $C_{1-4}$alkyl or a nitrogen protecting group. For example, $C_{1-10}$heteroaryl ("$C_{1-10}$" meaning between one and ten carbon atoms are present in the ring system), as used in this application includes, but is not limited to, pyrazolyl, pyridinyl, indolyl, thiazolyl, 3-oxo-3,4- dihydro-2H-benzo[b][1,4]oxazin-6-yl, furanyl, benzo[b]furanyl, pyrrolyl, 1H-indazolyl, imidazo[1,2-a]pyridin-3-yl, oxazolyl, benzo[d]thiazol-6-yl, 1H-benzo[d][1,2,3]triazol-5-yl, quinolinyl, 1H-indolyl, 3,4-dihydro-2H-pyrano[2,3-b]pyridinyl and 2,3-dihydrofuro[2,3-b]pyridinyl, 3-oxo-3,4-dihydro-2H-benzo[b][1,4]oxazin-7-yl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means a 3 to 8 member, saturated or partially unsaturated ring system containing 1 to 3 heteroatoms independently selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes, but is not limited to, morpholino, pyrrolidinyl, azepanyl, piperidinyl, isoquinolinyl, tetrahydrofuranyl, pyrrolidinyl, pyrrolidinyl-2-one, piperazinyl, piperidinylone, 1,4-dioxa-8-aza-spiro[4.5]dec-8-yl, etc.

"Halogen" (or halo) preferably represents chloro or fluoro, but may also be bromo or iodo.

"Kinase Panel" is a list of kinases comprising Abl(human), Abl(T315I), JAK2, JAK3, ALK, JNK1α1, ALK4, KDR, Aurora-A, Lck, Blk, MAPK1, Bmx, MAPKAP-K2, BRK, MEK1, CaMKII(rat), Met, CDK1/cyclinB, p70S6K, CHK2, PAK2, CK1, PDGFRα, CK2, PDK1, c-kit, Pim-2, c-RAF, PKA(h), CSK, PKBα, cSrc, PKCα, DYRK2, Plk3, EGFR, ROCK-I, Fes, Ron, FGFR3, Ros, Flt3, SAPK2α, Fms, SGK, Fyn, SIK, GSK3β, Syk, IGF-1R, Tie-2, IKKβ, TrKB, IR, WNK3, IRAK4, ZAP-70, ITK, AMPK(rat), LIMK1, Rsk2, Ax1, LKB1, SAPK2β, BrSK2, Lyn (h), SAPK3, BTK, MAPKAP-K3, SAPK4, CaMKIV, MARK1, Snk, CDK2/cyclinA, MINK, SRPK1, CDK3/cyclinE, MKK4(m), TAK1, CDK5/p25, MKK6(h), TBK1, CDK6/cyclinD3, MLCK, TrkA, CDK7/cyclinH/MAT1, MRCKβ, TSSK1, CHK1, MSK1, Yes, CK1d, MST2, ZIPK, c-Kit (D816V), MuSK, DAPK2, NEK2, DDR2, NEK6, DMPK, PAK-4, DRAK1, PAR-1Bα, EphA1, PDGFRβ, EphA2, Pim-1, EphA5, PKBβ, EphB2, PKCβI, EphB4, PKCδ, FGFR1, PKCη, FGFR2, PKCθ, FGFR4, PKD2, Fgr, PKG1β, Flt1, PRK2, Hck, PYK2, HIPK2, Ret, IKKα, RIPK2, IRR, ROCK-II(human), JNK2α2, Rse, JNK3, Rsk1(h), PI3 Kγ, PI3 Kδ and PI3-Kβ. Compounds of the invention are screened against the kinase panel (wild type and/or mutation thereof) and inhibit the activity of at least one of said panel members.

"Mutant forms of BCR-Abl" means single or multiple amino acid changes from the wild-type sequence. Mutations in BCR-ABL act by disrupting critical contact points between protein and inhibitor (for example, Gleevec, and the like), more often, by inducing a transition from the inactive to the active state, i.e. to a conformation to which BCR-ABL and Gleevec is unable to bind. From analyses of clinical samples, the repertoire of mutations found in association with the resistant phenotype has been increasing slowly but inexorably over time. Mutations seem to cluster in four main regions. One group of mutations (G250E, Q252R, Y253F/H, E255K/V) includes amino acids that form the phosphate-binding loop for ATP (also known as the P-loop). A second group (V289A, F311L, T315I, F317L) can be found in the Gleevec binding site and interacts directly with the inhibitor via hydrogen bonds or Van der Waals' interactions. The third group of mutations (M351T, E355G) clusters in close proximity to the catalytic domain. The fourth group of mutations (H396R/P) is located in the activation loop, whose conformation is the molecular switch controlling kinase activation/inactivation. BCR-ABL point mutations associated with Gleevec resistance detected in CML and ALL patients include: M224V, L248V, G250E, G250R, Q252R, Q252H, Y253H, Y253F, E255K, E255V, D276G, T277A, V289A, F311L, T315I, T315N, F317L, M343T, M315T, E355G, F359V, F359A, V379I, F382L, L387M, L387F, H396P, H396R, A397P, S417Y, E459K, and F486S (Amino acid positions, indicated by the single letter code, are those for the GenBank sequence, accession number AAB60394, and correspond to ABL type 1a; Martinelli et al., Haematologica/The Hematology Journal, 2005, April; 90-4). Unless otherwise stated for this invention, Bcr-Abl refers to wild-type and mutant forms of the enzyme.

"Treat", "treating" and "treatment" refer to a method of alleviating or abating a disease and/or its attendant symptoms.

DESCRIPTION OF THE PREFERRED EMBODIMENTS

The c-kit gene encodes a receptor tyrosine kinase and the ligand for the c-kit receptor is called the stem cell factor (SCF), which is the principal growth factor for mast cells. The activity of the c-kit receptor protein tyrosine kinase is regulated in normal cells, and the normal functional activity of the c-kit gene product is essential for maintenance of normal hematopoeisis, melanogenesis, genetogenesis, and growth and differentiation of mast cells. Mutations that cause constitutive activation of c-kit kinase activity in the absence of SCF binding are implicated in various diseases ranging from asthma to malignant human cancers.

In one embodiment, with reference to compounds of Formula I, are compounds of Formula Ia:

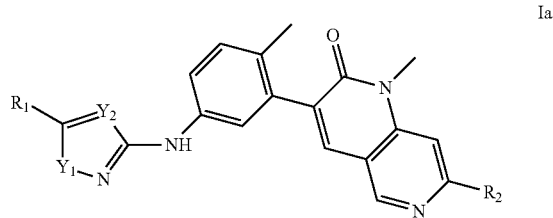

Ia in which:

$R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, =N(OH), $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1$NR$_{3a}$R$_{3b}$, —$X_1$C(O)R$_{3a}$, —$X_1$C(O)OR$_{3a}$, —$X_1$OR$_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein $R_{3a}$ and $R_{3b}$ are independently selected from hydrogen and $C_{1-6}$alkyl; $R_2$ is selected from methyl and ethyl; $Y_1$ is selected from O, S and NR$_4$; wherein $R_4$ is selected from hydrogen and $C_{1-4}$alkyl; and $Y_2$ is selected from N and CR$_4$; wherein $R_4$ is selected from hydrogen and $C_{1-4}$alkyl.

In another embodiment, $R_1$ is selected from halo, $C_{1-6}$alkyl, $C_{3-12}$cycloalkyl, $C_{3-8}$heterocycloalkyl, $C_{6-10}$aryl and C$_{3-10}$heteroaryl; wherein said C$_{1-6}$alkyl of R$_1$ is optionally substituted with 1 to 3 radicals independently selected from hydroxy, halo, C$_{1-6}$alkoxy, benzoxy and =N(OH); wherein said cycloalkyl, heterocycloalkyl, aryl or heteroaryl of R$_1$ is optionally substituted with 1 to 3 radicals independently selected from halo, hydroxy, cyano, C$_{1-6}$alkyl, halo-substituted-C$_{1-6}$alkyl, hydroxy-substituted-C$_{1-6}$alkyl, C$_{1-6}$alkoxy, halo-substituted-C$_{1-6}$alkoxy, —X$_1$NR$_{3a}$R$_{3b}$, —OR$_{3a}$, —C(O)R$_{3a}$ and C$_{3-10}$heteroaryl; wherein X$_1$ is selected from a bond and C$_{1-4}$alkylene; wherein R$_{3a}$ and R$_{3b}$ are independently selected from hydrogen and C$_{1-6}$alkyl; and R$_2$ is selected from methyl and ethyl.

In another embodiment, R$_1$ is selected from ethyl, t-butyl, t-butyl-methyl, isobutyl, propyl, isopropyl, neopentyl, sec-butyl, pentan-3-yl, 2-hydroxypropan-2-yl, 1-hydroxy-2-methylpropan-2-yl, 1-hydroxy-propan-2-yl, 1-hydroxy-2-methylpropyl, 1,1-difluoroethyl, 2-hydroxy-2-methylpropyl, 2-hydroxypropyl, ethoxy-methyl, 1-methoxyethyl, 1-phenoxyethyl, 1-(hydroxyimino)ethyl, pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl and cyclohexyl; wherein said pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl or cyclohexyl is optionally substituted with 1 to 3 radicals independently selected from chloro, fluoro, bromo, hydroxy, hydroxy-methyl, pyridinyl, cyano, methyl, methoxy, amino-methyl, methyl-carbonyl, trifluoromethyl, difluoroethyl and trifluoromethoxy.

In another embodiment are compounds selected from: 1,7-dimethyl-3-(2-methyl-5-(5-(pyridin-2-yl)-1,2,4-oxadiazol-3-ylamino)phenyl)-1,6-naphthyridin-2(1H)-one; 1,7-dimethyl-3-(2-methyl-5-(6-methylpyridin-3-yl)-1,2,4-oxadiazol-3-ylamino)phenyl)-1,6-naphthyridin-2(1H)-one; 3-(5-{[5-(6-chloropyridin-3-yl)-1,2,4-oxadiazol-3-yl]amino}-2-methylphenyl)-1,7-dimethyl-1,2-dihydro-1,6-naphthyridin-2-one; 3-(5-{[5-(2,5-dimethylfuran-3-yl)-1,2,4-oxadiazol-3-yl]amino}-2-methylphenyl)-1,7-dimethyl-1,2-dihydro-1,6-naphthyridin-2-one; 3-{5-[(5-cyclopropyl-1,2,4-oxadiazol-3-yl)amino]-2-methylphenyl}-1,7-dimethyl-1,2-dihydro-1,6-naphthyridin-2-one; 1,7-dimethyl-3-[2-methyl-5-({5-[6-(trifluoromethyl)pyridin-3-yl]-1,2,4-oxadiazol-3-yl}amino)phenyl]-1,2-dihydro-1,6-naphthyridin-2-one; 3-{5-[(5-ethyl-1,2,4-oxadiazol-3-yl)amino]-2-methylphenyl}-1,7-dimethyl-1,2-dihydro-1,6-naphthyridin-2-one; 1,7-dimethyl-3-(2-methyl-5-{[5-(propan-2-yl)-1,2,4-oxadiazol-3-yl]amino}phenyl)-1,2-dihydro-1,6-naphthyridin-2-one; 1,7-dimethyl-3-{2-methyl-5-[(5-phenyl-1,2,4-oxadiazol-3-yl)amino]phenyl}-1,2-dihydro-1,6-naphthyridin-2-one; 3-(5-{[5-(2-chlorophenyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(1,3-thiazol-2-yl)-1,2,4-oxadiazol-3-yl]amino}phenyl)-1,2-dihydro-1,6-naphthyridin-2-one; 1,7-dimethyl-3-(2-methyl-5-{[5-(pyridin-3-yl)-1,2,4-oxadiazol-3-yl]amino}phenyl)-1,2-dihydro-1,6-naphthyridin-2-one; 3-{5-[(5-cyclobutyl-1,2,4-oxadiazol-3-yl)amino]-2-methylphenyl}-1,7-dimethyl-1,2-dihydro-1,6-naphthyridin-2-one; 3-(5-{[5-(4-chlorophenyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(4-methylphenyl)-1,2,4-oxadiazol-3-yl]amino}phenyl)-1,2-dihydro-1,6-naphthyridin-2-one; 3-(5-{[5-(4-methoxyphenyl)-1,2,4-oxadiazol-3-yl]amino}-2-methylphenyl)-1,7-dimethyl-1,2-dihydro-1,6-naphthyridin-2-one; 3-{5-[(5-cyclopentyl-1,2,4-oxadiazol-3-yl)amino]-2-methylphenyl}-1,7-dimethyl-1,2-dihydro-1,6-naphthyridin-2-one; 1,7-dimethyl-3-(2-methyl-5-{[5-(2-methylphenyl)-1,2,4-oxadiazol-3-yl]amino}phenyl)-1,2-dihydro-1,6-naphthyridin-2-one; 1,7-dimethyl-3-(2-methyl-5-{[5-(3-methylphenyl)-1,2,4-oxadiazol-3-yl]amino}phenyl)-1,2-dihydro-1,6-naphthyridin-2-one; 3-{5-[(5-cyclohexyl-1,2,4-oxadiazol-3-yl)amino]-2-methylphenyl}-1,7-dimethyl-1,2-dihydro-1,6-naphthyridin-2-one; 3-(5-{[5-(2,2-dimethylpropyl)-1,2,4-oxadiazol-3-yl]amino}-2-methylphenyl)-1,7-dimethyl-1,2-dihydro-1,6-naphthyridin-2-one; 3-(5-{[5-(3-chlorophenyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(1-methyl-1H-pyrrol-2-yl)-1,2,4-oxadiazol-3-yl]amino}phenyl)-1,2-dihydro-1,6-naphthyridin-2-one; 1,7-dimethyl-3-(2-methyl-5-{[5-(1-methyl-1H-imidazol-2-yl)-1,2,4-oxadiazol-3-yl]amino}phenyl)-1,2-dihydro-1,6-naphthyridin-2-one; 1,7-dimethyl-3-(2-methyl-5-{[5-(1-methylpyrrolidin-2-yl)-1,2,4-oxadiazol-3-yl]amino}phenyl)-1,2-dihydro-1,6-naphthyridin-2-one; 3-(5-{[5-(4-fluorophenyl)-1,2,4-oxadiazol-3-yl]amino}-2-methylphenyl)-1,7-dimethyl-1,2-dihydro-1,6-naphthyridin-2-one; 3-(5-{[5-(5-fluoropyridin-2-yl)-1,2,4-oxadiazol-3-yl]amino}-2-methylphenyl)-1,7-dimethyl-1,2-dihydro-1,6-naphthyridin-2-one; 3-(5-{[5-(5-chloropyridin-2-yl)-1,2,4-oxadiazol-3-yl]amino}-2-methylphenyl)-1,7-dimethyl-1,2-dihydro-1,6-naphthyridin-2-one; 3-[5-({5-[(2S)-butan-2-yl]-1,2,4-oxadiazol-3-yl}amino)-2-methylphenyl]-1,7-dimethyl-1,2-dihydro-1,6-naphthyridin-2-one; 1,7-dimethyl-3-{2-methyl-5-[(5-propyl-1,2,4-oxadiazol-3-yl)amino]phenyl}-1,2-dihydro-1,6-naphthyridin-2-one; 3-(5-{[5-(butan-2-yl)-1,2,4-oxadiazol-3-yl]amino}-2-methylphenyl)-1,7-dimethyl-1,2-dihydro-1,6-naphthyridin-2-one; 3-{5-[(5-tert-butyl-1,2,4-oxadiazol-3-yl)amino]-2-methylphenyl}-1,7-dimethyl-1,2-dihydro-1,6-naphthyridin-2-one; 1,7-dimethyl-3-(2-methyl-5-{[5-(pentan-3-yl)-1,2,4-oxadiazol-3-yl]amino}phenyl)-1,2-dihydro-1,6-naphthyridin-2-one; 3-(5-{[5-(2-hydroxypropan-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(oxan-4-yl)-1,2,4-oxadiazol-3-yl]amino}phenyl)-1,2-dihydro-1,6-naphthyridin-2-one; 1,7-dimethyl-3-(2-methyl-5-{[5-(1-methylcyclopropyl)-1,2,4-oxadiazol-3-yl]amino}phenyl)-1,2-dihydro-1,6-naphthyridin-2-one; 3-(5-{[5-(1-hydroxy-2-methylpropan-2-yl)-1,2,4-oxadiazol-3-yl]amino}-2-methylphenyl)-1,7-dimethyl-1,2-dihydro-1,6-naphthyridin-2-one; 3-(5-{[5-(4-hydroxyphenyl)-1,2,4-oxadiazol-3-yl]amino}-2-methylphenyl)-1,7-dimethyl-1,2-dihydro-1,6-naphthyridin-2-one; 4-(3-{[3-(1,7-dimethyl-2-oxo-1,2-dihydro-1,6-naphthyridin-3-yl)-4-methylphenyl]amino}-1,2,4-oxadiazol-5-yl)benzonitrile; 2-(3-{[3-(1,7-dimethyl-2-oxo-1,2-dihydro-1,6-naphthyridin-3-yl)-4-methylphenyl]amino}-1,2,4-oxadiazol-5-yl)benzonitrile; 3-(5-{[5-(3-hydroxyphenyl)-1,2,4-oxadiazol-3-yl]amino}-2-methylphenyl)-1,7-dimethyl-1,2-dihydro-1,6-naphthyridin-2-one; 3-(3-{[3-(1,7-dimethyl-2-oxo-1,2-dihydro-1,6-naphthyridin-3-yl)-4-methylphenyl]amino}-1,2,4-oxadiazol-5-yl)benzonitrile; 1,7-dimethyl-3-[2-methyl-5-({5-[4-(trifluoromethoxy)phenyl]-1,2,4-oxadiazol-3-yl}amino)phenyl]-1,2-dihydro-1,6-naphthyridin-2-one; 3-(5-{[5-(6-hydroxypyridin-2-yl)-1,2,4-oxadiazol-3-yl]amino}-2-methylphenyl)-1,7-dimethyl-1,2-dihydro-1,6-naphthyridin-2-one; 3-[5-({5-[4-(hydroxymethyl)phenyl]-1, 2,4-oxadiazol-3-yl}amino)-2-methylphenyl]-1,7-dimethyl-1,2-dihydro-1,6-naphthyridin-2-one; 1,7-dimethyl-3-[2-methyl-5-({5-[2-(pyridin-3-yl)-1,3-thiazol-4-yl]-1,2,4-oxadiazol-3-yl}amino)phenyl]-1,2-dihydro-1,6-naphthyridin-2-one; 3-(5-{[5-(2,5-dimethyl-1,3-oxazol-4-yl)-1,2,4-oxadiazol-3-yl]amino}-2-methylphenyl)-1,7-dimethyl-1,2-dihydro-1,6-naphthyridin-2-one; 3-(5-{[5-(5-chloro-1H-indol-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(6-methylpyridin-2-yl)-1,2,4-oxadiazol-3-yl]amino}phenyl)-1,2-dihydro-1,6-naphthyridin-2-one; 3-(5-{[5-(2-chloro-6-methylpyridin-3-yl)-1,2,4-oxadiazol-3-yl]amino}-2-methylphenyl)-1,7-dimethyl-1,2-dihydro-1,6-naphthyridin-2-one; 3-(5-{[5-(6-chloropyridin-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(pyridin-4-yl)-1,2,4-oxadiazol-3-yl]amino}phenyl)-1,2-dihydro-1,6-naphthyridin-2-one; 1,7-dimethyl-3-(2-methyl-5-{[5-(6-methylpyridin-3-yl)-1,2,4-oxadiazol-3-yl]amino}phenyl)-1,2-dihydro-1,6-naphthyridin-2-one; 1,7-dimethyl-3-(2-methyl-5-{[5-(pyridin-2-yl)-1,2,4-oxadiazol-3-yl]amino}phenyl)-1,2-dihydro-1,6-naphthyridin-2-one; 1,7-dimethyl-3-(2-methyl-5-{[5-(5-methylpyridin-3-yl)-1,2,4-oxadiazol-3-yl]amino}phenyl)-1,2-dihydro-1,6-naphthyridin-2-one; 3-(5-{[5-(1,1-difluoroethyl)-1,2,4-oxadiazol-3-yl]amino}-2-methylphenyl)-1,7-dimethyl-1,2-dihydro-1,6-naphthyridin-2-one; 3-(5-{[5-(2-hydroxypropyl)-1,2,4-oxadiazol-3-yl]amino}-2-methylphenyl)-1,7-dimethyl-1,2-dihydro-1,6-naphthyridin-2-one; 3-(5-{[5-(2-hydroxy-2-methylpropyl)-1,2,4-oxadiazol-3-yl]amino}-2-methylphenyl)-1,7-dimethyl-1,2-dihydro-1,6-naphthyridin-2-one; 3-(5-{[5-(1-hydroxycyclopropyl)-1,2,4-oxadiazol-3-yl]amino}-2-methylphenyl)-1,7-dimethyl-1,2-dihydro-1,6-naphthyridin-2-one; 1,7-dimethyl-3-[2-methyl-5-({5-[1-(trifluoromethyl)cyclopropyl]-1,2,4-oxadiazol-3-yl}amino)phenyl]-1,2-dihydro-1,6-naphthyridin-2-one; 1,7-dimethyl-3-(2-methyl-5-{[5-(oxan-3-yl)-1,2,4-oxadiazol-3-yl]amino}phenyl)-1,2-dihydro-1,6-naphthyridin-2-one; 3-(5-{[5-(2,6-difluorophenyl)-1,2,4-oxadiazol-3-yl]amino}-2-methylphenyl)-1,7-dimethyl-1,2-dihydro-1,6-naphthyridin-2-one; 3-(5-{[5-(2,4-difluorophenyl)-1,2,4-oxadiazol-3-yl]amino}-2-methylphenyl)-1,7-dimethyl-1,2-dihydro-1,6-naphthyridin-2-one; 3-(5-{[5-(3,4-difluorophenyl)-1,2,4-oxadiazol-3-yl]amino}-2-methylphenyl)-1,7-dimethyl-1,2-dihydro-1,6-naphthyridin-2-one; 4-(3-{[3-(1,7-dimethyl-2-oxo-1,2-dihydro-1,6-naphthyridin-3-yl)-4-methylphenyl]amino}-1,2,4-oxadiazol-5-yl)-3-fluorobenzonitrile; 3-(5-{[5-(1-hydroxy-2-methylpropyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(3-methyloxetan-3-yl)-1,2,4-oxadiazol-3-yl]amino}phenyl)-1,2-dihydro-1,6-naphthyridin-2-one; 1,7-dimethyl-3-(2-methyl-5-{[5-(oxetan-2-yl)-1,2,4-oxadiazol-3-yl]amino}phenyl)-1,2-dihydro-1,6-naphthyridin-2-one; 3-(5-{[5-(1-hydroxypropan-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(2-methylpropyl)-1,2,4-oxadiazol-3-yl]amino}phenyl)-1,2-dihydro-1,6-naphthyridin-2-one; 3-[5-({5-[1-(hydroxymethyl)cyclopropyl]-1,2,4-oxadiazol-3-yl}amino)-2-methylphenyl]-1,7-dimethyl-1,2-dihydro-1,6-naphthyridin-2-one; 1,7-dimethyl-3-(2-methyl-5-{[5-(pyrazin-2-yl)-1,2,4-oxadiazol-3-yl]amino}phenyl)-1,2-dihydro-1,6-naphthyridin-2-one; 1,7-dimethyl-3-(2-methyl-5-{[5-(5-methylpyrazin-2-yl)-1,2,4-oxadiazol-3-yl]amino}phenyl)-1,2-dihydro-1,6-naphthyridin-2-one; 1,7-dimethyl-3-(2-methyl-5-{[5-(3-oxocyclobutyl)-1,2,4-oxadiazol-3-yl]amino}phenyl)-1,2-dihydro-1,6-naphthyridin-2-one; 3-(5-{[5-(3-hydroxycyclopentyl)-1,2,4-oxadiazol-3-yl]amino}-2-methylphenyl)-1,7-dimethyl-1,2-dihydro-1,6-naphthyridin-2-one; 3-(5-{[5-(ethoxymethyl)-1,2,4-oxadiazol-3-yl]amino}-2-methylphenyl)-1,7-dimethyl-1,2-dihydro-1,6-naphthyridin-2-one; 1,7-dimethyl-3-[2-methyl-5-({5-[(2R)-oxolan-2-yl]-1,2,4-oxadiazol-3-yl}amino)phenyl]-1,2-dihydro-1,6-naphthyridin-2-one; 3-[5-({5-[(1S)-1-methoxyethyl]-1,2,4-oxadiazol-3-yl}amino)-2-methylphenyl]-1,7-dimethyl-1,2-dihydro-1,6-naphthyridin-2-one; 1,7-dimethyl-3-[2-methyl-5-({5-[(2S)-oxolan-2-yl]-1,2,4-oxadiazol-3-yl}amino)phenyl]-1,2-dihydro-1,6-naphthyridin-2-one; 1,7-dimethyl-3-(2-methyl-5-{[5-(oxolan-3-yl)-1,2,4-oxadiazol-3-yl]amino}phenyl)-1,2-dihydro-1,6-naphthyridin-2-one; 1,7-dimethyl-3-(2-methyl-5-{[5-(3-methylpyridin-2-yl)-1,2,4-oxadiazol-3-yl]amino}phenyl)-1,2-dihydro-1,6-naphthyridin-2-one; 3-(5-{[5-(2-methoxy-4-methylphenyl)-1,2,4-oxadiazol-3-yl]amino}-2-methylphenyl)-1,7-dimethyl-1,2-dihydro-1,6-naphthyridin-2-one; 3-(5-{[5-(2-chloro-4-fluorophenyl)-1,2,4-oxadiazol-3-yl]amino}-2-methylphenyl)-1,7-dimethyl-1,2-dihydro-1,6-naphthyridin-2-one; 3-(5-{[5-(2,4-dichlorophenyl)-1,2,4-oxadiazol-3-yl]amino}-2-methylphenyl)-1,7-dimethyl-1,2-dihydro-1,6-naphthyridin-2-one; 3-(5-{[5-(3-hydroxycyclobutyl)-1,2,4-oxadiazol-3-yl]amino}-2-methylphenyl)-1,7-dimethyl-1,2-dihydro-1,6-naphthyridin-2-one; 3-(5-{[5-(3-hydroxy-3-methylcyclobutyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(oxan-2-yl)-1,2,4-oxadiazol-3-yl]amino}phenyl)-1,2-dihydro-1,6-naphthyridin-2-one; 1,7-dimethyl-3-{2-methyl-5-[(5-phenyl-1,2,4-oxadiazol-3-yl)amino]phenyl}-6-oxido-2-oxo-1,2-dihydro-1,6-naphthyridin-6-ium; 3-(5-{[5-(6-methoxypyridin-3-yl)-1,2,4-oxadiazol-3-yl]amino}-2-methylphenyl)-1,7-dimethyl-1,2-dihydro-1,6-naphthyridin-2-one; 3-[5-({5-[6-(1,1-difluoroethyl)pyridin-3-yl]-1,2,4-oxadiazol-3-yl}amino)-2-methylphenyl]-1,7-dimethyl-1,2-dihydro-1,6-naphthyridin-2-one; 3-[5-({5-[4-(1,1-difluoroethyl)phenyl]-1,2,4-oxadiazol-3-yl}amino)-2-methylphenyl]-1,7-dimethyl-1,2-dihydro-1,6-naphthyridin-2-one; 3-[5-({5-[4-(aminomethyl)phenyl]-1,2,4-oxadiazol-3-yl}amino)-2-methylphenyl]-1,7-dimethyl-1,2-dihydro-1,6-naphthyridin-2-one; 3-(5-{[5-(2-fluoropyridin-3-yl)-1,2,4-oxadiazol-3-yl]amino}-2-methylphenyl)-1,7-dimethyl-1,2-dihydro-1,6-naphthyridin-2-one; 3-[5-({5-[(1R)-1-hydroxy-2-methylpropyl]-1,2,4-oxadiazol-3-yl}amino)-2-methylphenyl]-1,7-dimethyl-1,2-dihydro-1,6-naphthyridin-2-one; 3-[5-({5-[(1S)-1-hydroxy-2-methylpropyl]-1,2,4-oxadiazol-3-yl}amino)-2-methylphenyl]-1,7-dimethyl-1,2-dihydro-1,6-naphthyridin-2-one; 3-(5-{[5-(2-acetylphenyl)-1,2,4-oxadiazol-3-yl]amino}-2-methylphenyl)-1,7-dimethyl-1,2-dihydro-1,6-naphthyridin-2-one; 3-(5-{[5-(4-acetylphenyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(1-phenoxyethyl)-1,2,4-oxadiazol-3-yl]amino}phenyl)-1,2-dihydro-1,6-naphthyridin-2-one; 1,7-dimethyl-3-[2-methyl-5-({5-[(2R)-2-methyloxolan-2-yl]-1,2,4-oxadiazol-3-yl}amino)phenyl]-1,2-dihydro-1,6-naphthyridin-2-one; 3-(5-{[5-(2,3-dihydro-1-benzofuran-2-yl)-1,2,4-oxadiazol-3-yl]amino}-2-methylphenyl)-1,7-dimethyl-1,2-dihydro-1,6-naphthyridin-2-one; 1,7-dimethyl-3-[2-methyl-5-({5-[(2R)-oxan-2-yl]-1,2,4-oxadiazol-3-yl}amino)phenyl]-1,2-dihydro-1,6-naphthyridin-2-one; 1,7-dimethyl-3-[2-methyl-5-({5-[(2S)- oxan-2-yl]-1,2,4-oxadiazol-3-yl}amino)phenyl]-1,2-dihydro-1,6-naphthyridin-2-one; 3-(5-{[5-(3-hydroxy-3-methylcyclobutyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(5-methylpyridin-2-yl)-1,2,4-oxadiazol-3-yl]amino}phenyl)-1,2-dihydro-1,6-naphthyridin-2-one; 3-(5-{[5-(5-methoxypyridin-2-yl)-1,2,4-oxadiazol-3-yl]amino}-2-methylphenyl)-1,7-dimethyl-1,2-dihydro-1,6-naphthyridin-2-one; 7-ethyl-1-methyl-3-(2-methyl-5-{[5-(propan-2-yl)-1,2,4-oxadiazol-3-yl]amino}phenyl)-1,2-dihydro-1,6-naphthyridin-2-one; 7-ethyl-1-methyl-3-(2-methyl-5-{[5-(pyridin-2-yl)-1,2,4-oxadiazol-3-yl]amino}phenyl)-1,2-dihydro-1,6-naphthyridin-2-one; and 1,7-dimethyl-3-{2-methyl-5-[(5-phenyl-1,2,4-thiadiazol-3-yl)amino]phenyl}-1,2-dihydro-1,6-naphthyridin-2-one.

In another embodiment, are compounds of Formula Ib:

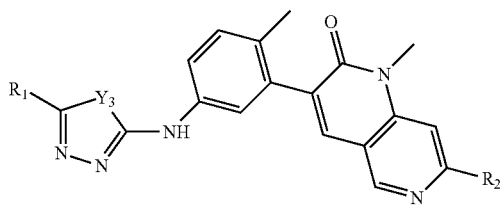

Ib in which: $R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1NR_{3a}R_{3b}$, —$X_1C(O)R_{3a}$, —$X_1C(O)OR_{3a}$, —$X_1OR_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein $R_{3a}$ and $R_{3b}$ are independently selected from hydrogen and $C_{1-6}$alkyl; $R_2$ is selected from methyl and ethyl; and $Y_3$ is selected from O, S and $NR_4$; wherein $R_4$ is selected from hydrogen and $C_{1-4}$alkyl.

In another embodiment, $R_1$ is selected from ethyl, t-butyl, t-butyl-methyl, isobutyl, propyl, isopropyl, neopentyl, sec-butyl, pentan-3-yl, 2-hydroxypropan-2-yl, 1-hydroxy-2-methylpropan-2-yl, 1-hydroxy-propan-2-yl, 1-hydroxy-2-methylpropyl, 1,1-difluoroethyl, 2-hydroxy-2-methylpropyl, 2-hydroxypropyl, ethoxy-methyl, 1-methoxyethyl, 1-phenoxyethyl, 1-(hydroxyimino)ethyl, pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl and cyclohexyl; wherein said pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl or cyclohexyl is optionally substituted with 1 to 3 radicals independently selected from chloro, fluoro, bromo, hydroxy, hydroxy-methyl, pyridinyl, cyano, methyl, methoxy, amino-methyl, methyl-carbonyl, trifluoromethyl, difluoroethyl and trifluoromethoxy.

In another embodiment, are compounds selected from: 1,7-dimethyl-3-(2-methyl-5-{[5-(4-methylphenyl)-1,3,4-oxadiazol-2-yl]amino}phenyl)-1,2-dihydro-1,6-naphthyridin-2-one; 3-(5-{[5-(4-methoxyphenyl)-1,3,4-oxadiazol-2-yl]amino}-2-methylphenyl)-1,7-dimethyl-1,2-dihydro-1,6-naphthyridin-2-one; 3-(5-{[5-(4-chlorophenyl)-1,3,4-oxadiazol-2-yl]amino}-2-methylphenyl)-1,7-dimethyl-1,2-dihydro-1,6-naphthyridin-2-one; 1,7-dimethyl-3-{2-methyl-5-[(5-phenyl-1,3,4-oxadiazol-2-yl)amino]phenyl}-1,2-dihydro-1,6-naphthyridin-2-one; 1,7-dimethyl-3-(2-methyl-5-{[5-(2-methylpropyl)-1,3,4-oxadiazol-2-yl]amino}phenyl)-1,2-dihydro-1,6-naphthyridin-2-one; 3-(5-{[5-(4-fluorophenyl)-1,3,4-oxadiazol-2-yl]amino}-2-methylphenyl)-1,7-dimethyl-1,2-dihydro-1,6-naphthyridin-2-one; 1,7-dimethyl-3-(2-methyl-5-{[5-(propan-2-yl)-1,3,4-oxadiazol-2-yl]amino}phenyl)-1,2-dihydro-1,6-naphthyridin-2-one; 3-{5-[(5-tert-butyl-1,3,4-oxadiazol-2-yl)amino]-2-methylphenyl}-1,7-dimethyl-1,2-dihydro-1,6-naphthyridin-2-one; 3-{5-[(5-cyclopropyl-1,3,4-oxadiazol-2-yl)amino]-2-methylphenyl}-1,7-dimethyl-1,2-dihydro-1,6-naphthyridin-2-one; 3-{5-[(5-cyclohexyl-1,3,4-oxadiazol-2-yl)amino]-2-methylphenyl}-1,7-dimethyl-1,2-dihydro-1,6-naphthyridin-2-one; 3-{5-[(5-cyclopentyl-4H-1,2,4-triazol-3-yl)amino]-2-methylphenyl}-1,7-dimethyl-1,2-dihydro-1,6-naphthyridin-2-one; 3-(5-{[5-(4-chlorophenyl)-4H-1,2,4-triazol-3-yl]amino}-2-methylphenyl)-1,7-dimethyl-1,2-dihydro-1,6-naphthyridin-2-one; 3-{5-[(5-cyclohexyl-4H-1,2,4-triazol-3-yl)amino]-2-methylphenyl}-1,7-dimethyl-1,2-dihydro-1,6-naphthyridin-2-one; 1,7-dimethyl-3-(2-methyl-5-{[5-(4-methylphenyl)-4H-1,2,4-triazol-3-yl]amino}phenyl)-1,2-dihydro-1,6-naphthyridin-2-one; 3-(5-{[5-(2,2-dimethylpropyl)-4H-1,2,4-triazol-3-yl]amino}-2-methylphenyl)-1,7-dimethyl-1,2-dihydro-1,6-naphthyridin-2-one; 1,7-dimethyl-3-{2-methyl-5-[(5-phenyl-4H-1,2,4-triazol-3-yl)amino]phenyl}-1,2-dihydro-1,6-naphthyridin-2-one; 3-(5-{[5-(3-chlorophenyl)-4H-1,2,4-triazol-3-yl]amino}-2-methylphenyl)-1,7-dimethyl-1,2-dihydro-1,6-naphthyridin-2-one; 3-{5-[(5-cyclobutyl-4H-1,2,4-triazol-3-yl)amino]-2-methylphenyl}-1,7-dimethyl-1,2-dihydro-1,6-naphthyridin-2-one; and 1,7-dimethyl-3-{2-methyl-5-[(5-phenyl-1,3,4-thiadiazol-2-yl)amino]phenyl}-1,2-dihydro-1,6-naphthyridin-2-one.

In another embodiment are compounds of Formula Ic:

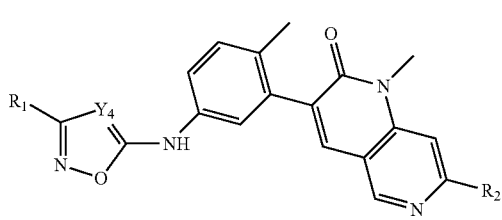

Ic in which: $R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1NR_{3a}R_{3b}$, —$X_1C(O)R_{3a}$, —$X_1C(O)OR_{3a}$, —$X_1OR_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein $R_{3a}$ and $R_{3b}$ are independently selected from hydrogen and $C_{1-6}$alkyl; $R_2$ is selected from methyl and ethyl; and $Y_4$ is selected from $CR_4$ and $NR_4$; wherein $R_4$ is selected from hydrogen and $C_{1-4}$alkyl.

In another embodiment, $R_1$ is selected from ethyl, t-butyl, t-butyl-methyl, isobutyl, propyl, isopropyl, neopentyl, sec-butyl, pentan-3-yl, 2-hydroxypropan-2-yl, 1-hydroxy-2-methylpropan-2-yl, 1-hydroxy-propan-2-yl, 1-hydroxy-2-methylpropyl, 1,1-difluoroethyl, 2-hydroxy-2-methylpropyl, 2-hydroxypropyl, ethoxy-methyl, 1-methoxyethyl, 1-phenoxyethyl, 1-(hydroxyimino)ethyl, pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl and cyclohexyl; wherein said pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl or cyclohexyl is optionally substituted with 1 to 3 radicals independently selected from chloro, fluoro, bromo, hydroxy, hydroxy-methyl, pyridinyl, cyano, methyl, methoxy, amino-methyl, methyl-carbonyl, trifluoromethyl, difluoroethyl and trifluoromethoxy.

In another embodiment are compounds selected from: 1,7-dimethyl-3-{2-methyl-5-[(3-phenyl-1,2,4-oxadiazol-5-yl)amino]phenyl}-1,2-dihydro-1,6-naphthyridin-2-one; 1,7-dimethyl-3-(2-methyl-5-{[3-(pyridin-2-yl)-1,2,4-oxadiazol-5-yl]amino}phenyl)-1,2-dihydro-1,6-naphthyridin-2-one; 1,7-dimethyl-3-(2-methyl-5-{[3-(propan-2-yl)-1,2,4-oxadiazol-5-yl]amino}phenyl)-1,2-dihydro-1,6-naphthyridin-2-one; and 1,7-dimethyl-3-(2-methyl-5-{[3-(1,3-thiazol-2-yl)-1,2-oxazol-5-yl]amino}phenyl)-1,2-dihydro-1,6-naphthyridin-2-one.

In another embodiment are compounds detailed in the examples and table, infra.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

In one embodiment, the invention provides methods for treating a disease or condition modulated by the c-kit and PDGFRα/β kinase receptors, comprising administering compounds of Formula I, or pharmaceutically acceptable salts or pharmaceutical compositions thereof.

Examples of c-kit and/or PDGFR mediated disease or conditions which may be mediated using the compounds and compositions of the invention include but are not limited to a neoplastic disorder, an allergy disorder, an inflammatory disorder, an autoimmune disorder, a graft-versus-host disease, a *Plasmodium* related disease, a mast cell associated disease, a metabolic syndrome, a CNS related disorder, a neurodegenerative disorder, a pain condition, a substance abuse disorder, a prion disease, a cancer, a heart disease, a fibrotic disease, pulmonary arterial hypertension (PAH), or primary pulmonary hypertension (PPH).

Examples of a mast cell associated disease which may be treated using compounds and compositions of the invention include but are not limited to acne and *Propionibacterium acnes*, Fibrodysplasia ossificans progressiva (FOP), inflammation and tissue destruction induced by exposure to chemical or biological weapons (such as anthrax and sulfur-mustard), Cystic fibrosis; renal disease, inflammatory muscle disorders, HIV, type II diabetes, cerebral ischemia, mastocytosis, drug dependence and withdrawal symptoms, CNS disorders, preventing and minimizing hair loss, bacterial infections, interstitial cystitis, inflammatory bowel syndrome (IBS), inflammatory bowel diseases (IBD), tumor angiogenesis, autoimmune diseases, inflammatory diseases, Multiple Sclerosis (MS), allergic disorders (including asthma), and bone loss.

Examples of neoplastic disorders which may be treated using the compounds and compositions of the invention include but are not limited to mastocytosis, gastrointestinal stromal tumor, small cell lung cancer, non-small cell lung cancer, acute myelocytic leukemia, acute lymphocytic leukemia, myelodysplastic syndrome, chronic myelogenous leukemia, colorectal carcinoma, gastric carcinoma, testicular cancer, glioblastoma or astrocytoma and melanoma.

Examples of allergy disorders which may be treated using the compounds and compositions of the invention include but are not limited to asthma, allergic rhinitis, allergic sinusitis, anaphylactic syndrome, urticaria, angioedema, atopic dermatitis, allergic contact dermatitis, dermatosis, erythema nodosum, erythema multiforme, cutaneous necrotizing venulitis, insect bite skin inflammation, or blood sucking parasite infestation.

Examples of inflammatory disorders which may be treated using the compounds and compositions of the invention include but are not limited to rheumatoid arthritis, IBS, IBD, conjunctivitis, rheumatoid spondylitis, osteoarthritis or gouty arthritis.

Examples of autoimmune disorders which may be treated using the compounds and compositions of the invention include but are not limited to multiple sclerosis, psoriasis, intestine inflammatory disease, ulcerative colitis, Crohn's disease, rheumatoid arthritis, polyarthritis, local or systemic scleroderma, systemic lupus erythematosus, discoid lupus erythematosis, cutaneous lupus, dermatomyositis, polymyositis, Sjogren's syndrome, nodular panarteritis, autoimmune enteropathy or proliferative glomerulonephritis.

Examples of graft-versus-host diseases which may be treated using the compounds and compositions of the invention include but are not limited to organ transplantation graft rejection, such as kidney transplantation, pancreas transplantation, liver transplantation, heart transplantation, lung transplantation, or bone marrow transplantation.

Examples of metabolic syndrome which may be treated using the compounds and compositions of the invention include but are not limited to type I diabetes, type II diabetes, or obesity.

Examples of CNS related disorders which may be treated using the compounds and compositions of the invention include but are not limited to depression, dysthymic disorder, cyclothymic disorder, anorexia, bulimia, premenstrual syndrome, post-menopause syndrome, mental slowing, loss of concentration, pessimistic worry, agitation, self-deprecation and decreased libido, an anxiety disorder, a psychiatric disorder or schizophrenia.

Examples of depression conditions which may be treated using the compounds and compositions of the invention include but are not limited to bipolar depression, severe or melancholic depression, atypical depression, refractory depression, or seasonal depression. Examples of anxiety disorders which may be treated using the compounds and compositions of the invention include but are not limited to anxiety associated with hyperventilation and cardiac arrhythmias, phobic disorders, obsessive-compulsive disorder, posttraumatic stress disorder, acute stress disorder, and generalized anxiety disorder. Examples of psychiatric disorders which may be treated using the compounds and compositions of the invention include but are not limited to panic attacks, including psychosis, delusional disorders, conversion disorders, phobias, mania, delirium, dissociative episodes including dissociative amnesia, dissociative fugue and dissociative suicidal behavior, self-neglect, violent or aggressive behavior, trauma, borderline personality, and acute psychosis such as schizophrenia, including paranoid schizophrenia, disorganized schizophrenia, catatonic schizophrenia, and undifferentiated schizophrenia.

Examples of neurodegenerative disorder which may be treated using the compounds and compositions of the invention include but are not limited to Alzheimer's disease, Parkinson's disease, Huntington's disease, the prion diseases, Motor Neuron Disease (MND), or Amyotrophic Lateral Sclerosis (ALS).

Examples of pain conditions which may be treated using the compounds and compositions of the invention include but are not limited to acute pain, postoperative pain, chronic pain, nociceptive pain, cancer pain, neuropathic pain or psychogenic pain syndrome.

Examples of substance use disorders which may be treated using the compounds and compositions of the invention include but are not limited to drug addiction, drug abuse, drug habituation, drug dependence, withdrawal syndrome or overdose.

Examples of cancers which may be treated using the compounds and compositions of the invention include but are not limited to melanoma, gastrointestinal stromal tumor (GIST), small cell lung cancer, or other solid tumors.

Examples of fibrotic diseases which may be treated using the compounds and compositions of the invention include but are not limited to hepatitis C(HCV), liver fibrosis, nonalcoholic steatohepatitis (NASH), cirrhosis in liver, pulmonary fibrosis, or bone marrow fibrosis.

In another embodiment, the invention provides methods for treating a disease or condition modulated by the c-kit kinase receptor, comprising administering compounds of Formula I, or pharmaceutically acceptable salts or pharmaceutical compositions thereof.

Pharmacology and Utility

Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to c-kit, Abl, Lyn, MAPK14 (p38delta), PDGFRα, PDGFRβ, ARG, BCR-Abl, BRK, EphB, Fms, Fyn, KDR, LCK, b-Raf, c-Raf, SAPK2, Src, Tie2 and TrkB kinase.

Mast cells (MC) are tissue elements derived from a particular subset of hematopoietic stem cells that produce a large variety of mediators most of which having strong pro-inflammatory activities. Since MCs are distributed in almost all the body sites, hypersecretion of mediators by activated elements can lead to multiple organ failures. Mast cells are, therefore, central players involved in many diseases. The present invention relates to a method for treating mast cell associated diseases comprising administering a compound capable of depleting mast cells or a compound inhibiting mast cell degranulation, to a human in need of such treatment. Such compounds can be chosen from c-kit inhibitors and more particularly non-toxic, selective and potent c-kit inhibitors. Preferably, said inhibitors are unable to promote death of IL-3 dependent cells cultured in presence of IL-3.

Mast cell associated diseases include, but are not limited to: acne and *Propionibacterium acnes* (acne encompasses all forms of chronic inflammation of the skin including those induced by *Propionibacterium acnes*); an extremely rare and disabling genetic disorder of connective tissue known as Fibrodysplasia ossificans progressiva (FOP); the detrimental effects of inflammation and tissue destruction induced by exposure to chemical or biological weapons (such as anthrax, sulfur-mustard, etc.); Cystic fibrosis (a lung, digestive and reproductive systems genetic disease); renal disease such as Acute nephritic syndrome, glomerulonephritis, renal amyloidosis, renal interstitial fibrosis (the final common pathway leading to end-stage renal disease in various nephropathies); inflammatory muscle disorders including myositis and muscular dystrophy; HIV (for example, depleting HIV infected mast cells can be a new route for treating HIV infection and related diseases); treating type II diabetes, obesity and related disorders (mast cells regulate a number of the processes that contribute to the development of atherosclerosis, including hyperglycemia, hypercholesterolemia, hypertension, endothelial dysfunction, insulin resistance, and vascular remodeling; cerebral ischemia; mastocytosis (a very heterogeneous group of disorders characterized by an abnormal accumulation of mast cells in different tissues, mainly in the skin and the bone marrow, but also in spleen, liver, lymph nodes, and the gastrointestinal tract); drug dependence and withdrawal symptoms (particularly drug addiction, drug abuse, drug habituation, drug dependence, withdrawal syndrome and overdose); CNS disorders (particularly depression, schizophrenia, anxiety, migraine, memory loss, pain and neurodegenerative diseases); promoting hair growth (including preventing and minimizing hair loss); bacterial infections (particularly infections caused by FimH expressing bacteria); interstitial cystitis (a chronic inflammation of the bladder wall resulting in tissue damage, especially at the interstices between the cells in the lining of the bladder); Inflammatory bowel diseases (generally applied to four diseases of the bowel, namely Crohn's disease, ulcerative colitis, indeterminate colitis, and infectious colitis); tumor angiogenesis; autoimmune diseases (particularly multiple sclerosis, ulcerative colitis, Crohn's disease, rheumatoid arthritis and polyarthritis, scleroderma, lupus erythematosus, dermatomyositis, pemphigus, polymyositis, vasculitis and graft-versus host diseases); inflammatory diseases such as rheumatoid arthritis (RA); Multiple Sclerosis (MS); allergic disorders (particularly allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation, bronchial asthma); and bone loss.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Some compounds of the present invention inhibit abl kinase, especially v-abl kinase. Some of the compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

The Ras-Raf-MEK-ERK signaling pathway mediates cellular response to growth signals. Ras is mutated to an oncogenic form in ~15% of human cancer. The Raf family belongs to the serine/threonine protein kinase and it includes three members, A-Raf, B-Raf and c-Raf (or Raf-1). The focus on Raf being a drug target has centered on the relationship of Raf as a downstream effector of Ras. However, recent data suggests that B-Raf may have a prominent role in the formation of certain tumors with no requirement for an activated Ras allele (Nature 417, 949-954 (1 Jul. 2002). In particular, B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

The compounds of the present invention also inhibit cellular processes involving c-Raf kinase. c-Raf is activated by the ras oncogene, which is mutated in a wide number of human cancers. Therefore inhibition of the kinase activity of c-Raf may provide a way to prevent ras mediated tumor growth [Campbell, S. L., Oncogene, 17, 1395 (1998)].

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of: tumor diseases, such as gliomas, sarcomas, prostate tumors, and tumors of the colon, breast, and ovary; hypereosinophilia; fibrosis; pulmonary hypertension; and cardiovascular diseases.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The trk family of neurotrophin receptors (trkA, trkB, trkC) promotes the survival, growth and differentiation of the neuronal and non-neuronal tissues. The TrkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. TkrB is, moreover, expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

The kinase, c-Src transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The Tec family kinase, Bmx, a non-receptor protein-tyrosine kinase, controls the proliferation of mammary epithelial cancer cells.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers Inhibitors of FGFR3 activity are useful in the treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis.

The activity of serum and glucocorticoid-regulated kinase (SGK), is correlated to perturbed ion-channel activities, in particular, those of sodium and/or potassium channels and compounds of the invention can be useful for treating hypertension.

Lin et al (1997) J. Clin. Invest. 100, 8: 2072-2078 and P. Lin (1998) PNAS 95, 8829-8834, have shown an inhibition of tumor growth and vascularization and also a decrease in lung metastases during adenoviral infections or during injections of the extracellular domain of Tie-2 (Tek) in breast tumor and melanoma xenograft models. Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemangioma and cancers).

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases. As a result of the importance of JNK activation associated with liver disease or episodes of hepatic ischemia, compounds of the invention may also be useful to treat various hepatic disorders. A role for JNK in cardiovascular disease such as myocardial infarction or congestive heart failure has also been reported as it has been shown JNK mediates hypertrophic responses to various forms of cardiac stress. It has been demonstrated that the JNK cascade also plays a role in T-cell activation, including activation of the IL-2 promoter. Thus, inhibitors of JNK may have therapeutic value in altering pathologic immune responses. A role for JNK activation in various cancers has also been established, suggesting the potential use of JNK inhibitors in cancer. For example, constitutively activated JNK is associated with HTLV-1 mediated tumorigenesis [Oncogene 13:135-42 (1996)]. JNK may play a role in Kaposi's sarcoma (KS). Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92:2450-60 (1998)].

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. For example, expression of the c-raf protein is believed to play a role in abnormal cell proliferation since it has been reported that 60% of all lung carcinoma cell lines express unusually high levels of c-raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

The stress activated protein kinases (SAPKs) are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Therefore, agents that inhibit SAPK activity in a cell prevent DNA repair and sensitize the cell to agents that induce DNA damage or inhibit DNA synthesis and induce apoptosis of a cell or that inhibit cell proliferation.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleiotropic functions, among them is a key role in the regulation of mRNA translation during protein biosynthesis (Eur. J. Biochem 2000 November; 267 (21): 6321-30, Exp Cell Res. Nov. 25, 1999; 253 (1):100-9, Mol Cell Endocrinol. May 25, 1999; 151(1-2):65-77). The phosphorylation of the S6 ribosomal protein by p70S6 has also been implicated in the regulation of cell motility (Immunol. Cell Biol. 2000 August; 78(4):447-51) and cell growth (Prog. Nucleic Acid Res. Mol. Biol., 2000; 65:101-27), and hence, may be important in tumor metastasis, the immune response and tissue repair as well as other disease conditions.

The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Agents that inhibit SAPK activity in a cell prevent DNA repair and sensitize the cell to those cancer therapeutic modalities that act by inducing DNA damage.

BTK plays a role in autoimmune and/or inflammatory disease such as systemic lupus erythematosus (SLE), rheumatoid arthritis, multiple vasculitides, idiopathic thrombocytopenic purpura (ITP), myasthenia gravis, and asthma. Because of BTK's role in B-cell activation, inhibitors of BTK are useful as inhibitors of B-cell mediated pathogenic activity, such as autoantibody production, and are useful for the treatment of B-cell lymphoma and leukemia.

CHK2 is a member of the checkpoint kinase family of serine/threonine protein kinases and is involved in a mechanism used for surveillance of DNA damage, such as damage caused by environmental mutagens and endogenous reactive oxygen species. As a result, it is implicated as a tumor suppressor and target for cancer therapy.

CSK influences the metastatic potential of cancer cells, particularly colon cancer.

Fes is a non-receptor protein tyrosine kinase that has been implicated in a variety of cytokine signal transduction pathways, as well as differentiation of myeloid cells. Fes is also a key component of the granulocyte differentiation machinery.

Flt3 receptor tyrosine kinase activity is implicated in leukemias and myelodysplastic syndrome. In approximately 25% of AML the leukemia cells express a constitutively active form of auto-phosphorylated (p) FLT3 tyrosine kinase on the cell surface. The activity of p-FLT3 confers growth and survival advantage on the leukemic cells. Patients with acute leukemia, whose leukemia cells express p-FLT3 kinase activity, have a poor overall clinical outcome Inhibition of p-FLT3 kinase activity induces apoptosis (programmed cell death) of the leukemic cells.

Inhibitors of IKKα and IKKβ (1 & 2) are therapeutics for diseases which include rheumatoid arthritis, transplant rejection, inflammatory bowel disease, osteoarthritis, asthma, chronic obstructive pulmonary disease, atherosclerosis, psoriasis, multiple sclerosis, stroke, systemic lupus erythematosus, Alzheimer's disease, brain ischemia, traumatic brain injury, Parkinson's disease, amyotrophic lateral sclerosis, subarachnoid hemorrhage or other diseases or disorders associated with excessive production of inflammatory mediators in the brain and central nervous system.

Met is associated with most types of the major human cancers and expression is often correlated with poor prognosis and metastasis Inhibitors of Met are therapeutics for diseases which include cancers such as lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem glioma or pituitary adenomas), cancers of the blood such as acute myeloid leukemia, chronic myeloid leukemia, etc, Barrett's esophagus (pre-malignant syndrome) neoplastic cutaneous disease, psoriasis, mycoses fungoides and benign prostatic hypertrophy, diabetes related diseases such as diabetic retinopathy, retinal ischemia and retinal neovascularization, hepatic cirrhosis, cardiovascular disease such as atherosclerosis, immunological disease such as autoimmune disease and renal disease. Preferably, the disease is cancer such as acute myeloid leukemia and colorectal cancer.

The Nima-related kinase 2 (Nek2) is a cell cycle-regulated protein kinase with maximal activity at the onset of mitosis that localizes to the centrosome. Functional studies have implicated Nek2 in regulation of centrosome separation and spindle formation. Nek2 protein is elevated 2- to 5-fold in cell lines derived from a range of human tumors including those of cervical, ovarian, prostate, and particularly breast.

p70S6K-mediated diseases or conditions include, but are not limited to, proliferative disorders, such as cancer and tuberous sclerosis.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 1000 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal, inhaled or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives. Suitable pharmaceutical excipients can be found in the art (see Handbook of Pharmaceutical Excipients, Fifth Edition—edited by Raymond Rowe, Paul Sheskey and Sian Owen).

Compounds of the invention can be administered in therapeutically effective amounts in combination with one or more therapeutic agents (pharmaceutical combinations). For example, synergistic effects can occur with other asthma therapies, for example, steroids and leukotriene antagonists.

For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Compounds of the invention can be used in combination with: antifibrotic agents such as pirfenidone and tacrolimus; agents used to treat PAH such as endothelin antagonists (for example, bosentan) and PDE5 inhibitors (for example, sildenafil); medication for treating asthma, for example, bronchodilators such as $\beta_2$-agonists, xanthines (e.g. methylxanthines) and anticholinerigcs; and an anti-inflammatory agent. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula Ia can be prepared by proceeding as in the following Reaction Schemes I:

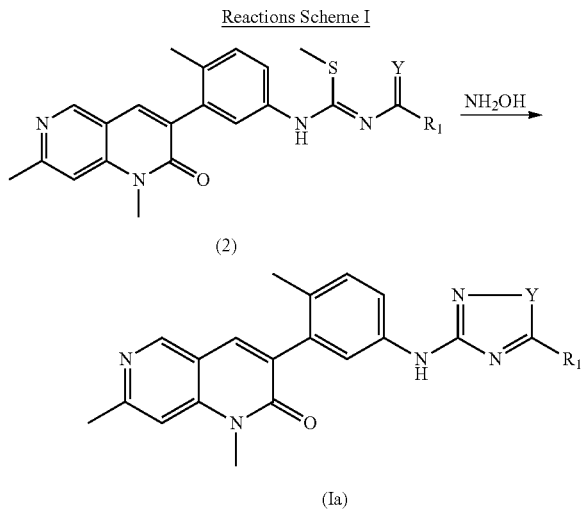

wherein $R_1$ and Y are as described in the Summary of the Invention. A compound of Formula Ia can be prepared by reacting of a compound of formula 2 with a suitable intermediate (for example, $NH_2OH$, and the like) and in the presence of a suitable solvent (for example, ethanol, and the like). The reaction is carried out in a temperature range of about 50° C. to about 180° C. and can take up to 24 hours to complete.

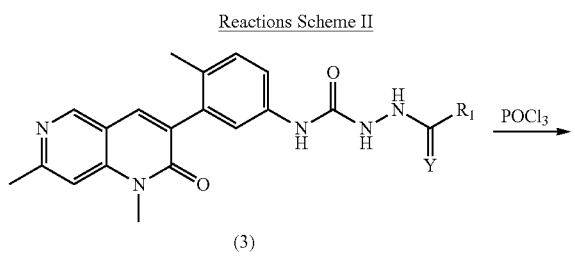

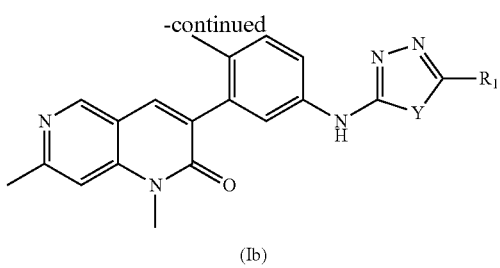

(Ib)

wherein $R_1$ and Y are as described in the Summary of the Invention. A compound of Formula Ib can be prepared by reacting of a compound of formula 3 with a suitable reagent (for example, $POCl_3$, and the like) and in the presence of a suitable solvent (for example, THF, and the like). The reaction is carried out in a temperature range of about 50° C. to about 180° C. and can take up to 24 hours to complete.

Detailed examples of the synthesis of compounds of formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I and II, and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Synthesis of Intermediates

Synthesis of 3-(5-amino-2-methylphenyl)-7-chloro-1-methyl-1,6-naphthyridin-2(1H)-one (8)

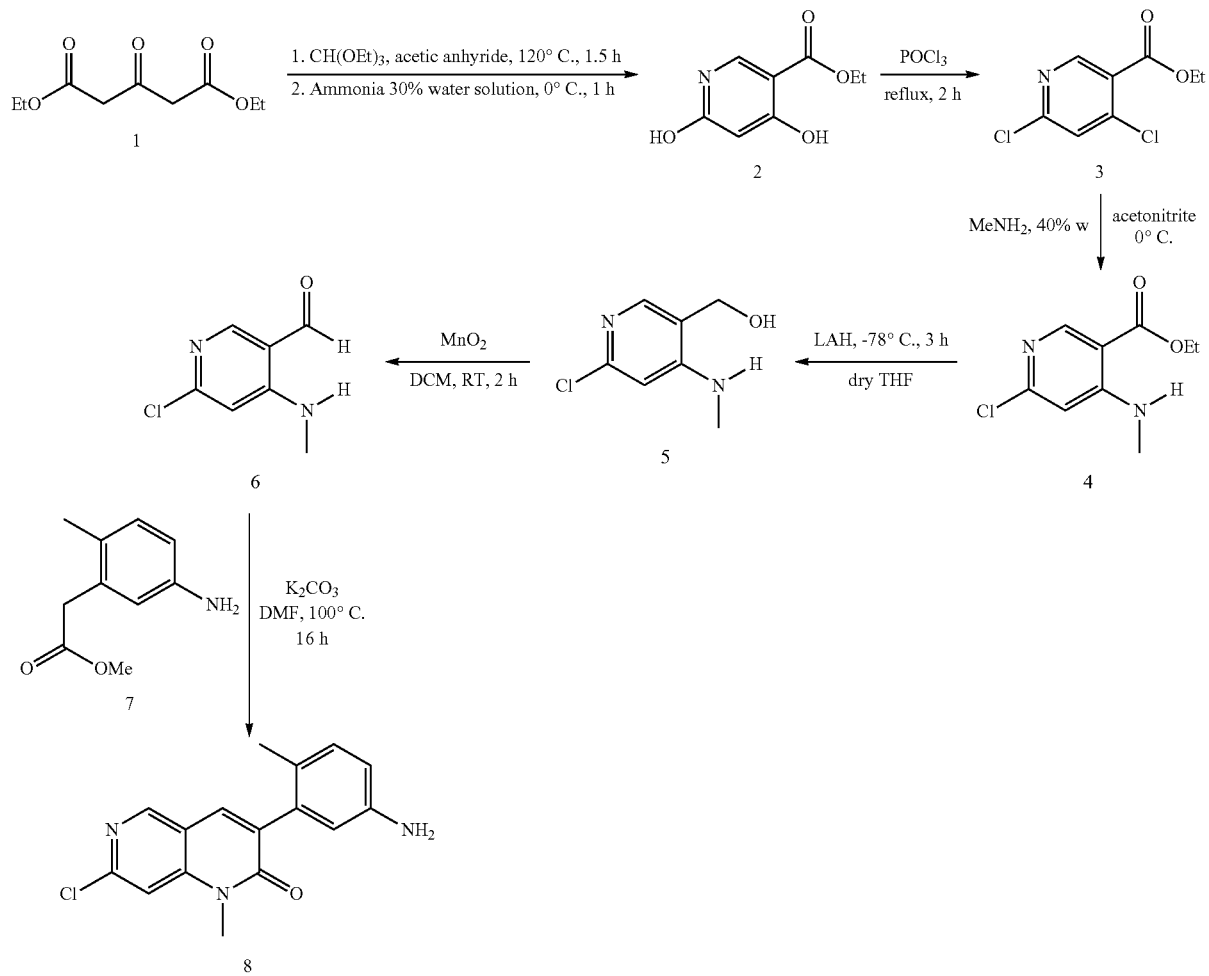

Into a 2 L flask were placed diethyl 1,3-acetonedicarboxylate 1 (160 g, 0.79 mol), triethyl orthoformate (129 g, 0.87 mol), and acetic anhydride (161 g, 1.58 mol). The resulting mixture was heated to 120° C. for 1.5 h. The mixture was cooled to rt and volatiles were removed by vacuum distillation (150-200 mm Hg) at 90-100° C. Light-yellow oil was collected in the condenser. The residue left in the flask was then cooled in an ice bath and mixed with 30% ammonia (65 mL). The reaction was allowed to stand in the ice bath for 1 h and was then acidified with 2N HCl to pH<5. The mixture was concentrated in vacuo and the crude product was purified using flash chromatography (ethyl acetate:petroleum ether=1:1). The product 2 was isolated as colorless oil.

4,6-Dihydroxynicotinic acid ethyl ester 2 (5 g, 0.3 mol) was mixed with $POCl_3$ (500 mL) in a 2 L flask and heated to 110° C. for 3 h. After cooling to rt most of the $POCl_3$ was removed in vacuo. The crude dark-colored product was poured into a small amount of ice-water mixture, and neutralized with saturated aqueous sodium carbonate. The product was extracted twice with ethyl acetate. The combined organic layer was washed with saturated aqueous sodium chloride and dried over $Na_2SO_4$. Purification using flash chromatography (ethyl acetate:petroleum ether=1:3) afforded the product, 4,6-dichloronicotinic acid ethyl ester 3, as a white solid. $^1$H NMR (300 MHz, $CDCl_3$) δ 8.85 (s, 1H), 7.47 (s, 1H), 4.43 (q, J=7.2 Hz, 2H), 1.41 (t, J=7.2 Hz, 3H).

4,6-Dichloronicotinic acid ethyl ester 3 (43 g, 195 mmol) was dissolved in acetonitrile (600 mL), cooled to 0° C. and methylamine (125 mL of a 40% water solution, 977 mmol) was slowly added. The reaction was stirred at 0° C. for 30 minutes and warmed to rt for another 3 h. Solvent was removed in vacuo and the crude product was purified using flash chromatography (ethyl acetate:petroleum ether=1:1). The product 4 was isolated as a white solid. $^1$H NMR (300 MHz, $CDCl_3$) δ 8.66 (s, 1H), 8.12 (bs, 1H), 6.53 (s, 1H), 4.34 (q, J=7.2 Hz, 2H), 2.92 (s, 3H), 1.37 (t, J=7.2 Hz, 3H).

6-Chloro-4-methylaminonicotinic acid ethyl ester 4 (33 g, 156 mmol) was dissolved in anhydrous THF (500 mL) and cooled to −78° C. To the solution was slowly added a solution of LAH (12.5 g, 329 mmol) in THF (500 mL). After the addition was complete, the reaction was kept at −78° C. for 1 h. The mixture was warmed to rt and a small amount of MeOH/ethyl acetate (1/1) was slowly added to destroy the excess LAH. The crude product was filtered through a celite plug and washed twice using ethyl acetate. After solvent removal in vacuo, the crude product was purified by flash chromatography (ethyl acetate:petroleum ether=1:1). The product 5 was obtained as a white solid. $^1$H NMR (300 MHz, CDCl$_3$) δ 7.36 (s, 1H), 6.48 (s, 1H), 5.55 (bs, 1H), 4.63 (s, 2H), 2.89 (d, J=5.1 Hz, 3H).

Compound 5 (20 g, 116 mmol) was dissolved in DCM (250 mL) and MnO$_2$ (100 g, 1.16 mol) was added. The reaction was stirred at rt overnight, then filtered through a celite plug and washed using ethyl acetate. After removal of the solvent in vacuo, 6 was obtained and used in the next step without further purification. $^1$H NMR (300 MHz, CDCl$_3$) δ 9.85 (s, 1H), 8.59 (bs, 1H), 8.31 (s, 1H), 6.59 (s, 1H), 2.96 (d, J=5.1 Hz, 3H).

6-Chloro-4-methylamino-pyridine-3-carbaldehyde 6 (19.8 g, 116 mmol) was mixed with 2-(5-amino-2-methylphenyl)acetic acid methyl ester 7 (27 g, 151 mmol) and potassium carbonate (48.1 g, 348 mmol) in DMF (1 L). The mixture was heated to 100° C. for 16 h. After cooling to rt and removing solvent in vacuo, the crude product was purified using flash chromatography (ethyl acetate:petroleum ether=1:1). The title compound 8 was obtained as a pale solid. $^1$H NMR (300 MHz, CDCl$_3$) δ 8.56 (s, 1H), 7.63 (s, 1H), 7.27 (s, 1H), 7.06 (d, J=8.1 Hz, 1H), 6.74 (dd, J=2.4, 8.1 Hz, 1H), 6.58 (d, J=2.4 Hz, 1H), 3.71 (s, 2H), 2.10 (s, 3H).

Synthesis of methyl 2-(5-amino-2-methylphenyl)acetate (7)

treated with methanesulfonyl chloride (72 g, 632 mmol) and diisopropylethylamine (89 g, 689 mmol) for 30 minutes. The reaction was warmed to rt and stirred for another 30 minutes. It was quenched by adding water (600 mL). The organic layer was washed with brine, dried over sodium sulfate and filtered. After removing the solvent in vacuo, the product 11 was isolated as yellow oil and was used in the next step without further purification.

To a solution of crude 11 (141 g, 0.575 mol) in acetonitrile (4 L) was added sodium cyanide (84.4 g, 1.7 mol) and the resulting mixture was heated at reflux for 8 h. The reaction was cooled to rt and solvent was removed in vacuo. The crude product was dissolved in DCM and filtered. The filtrate was washed with brine and dried over sodium sulfate. After removing solvent in vacuo, the crude product was purified using flash chromatography (ethyl acetate:petroleum ether=1:1). The product 12 was obtained as a yellow solid. $^1$H NMR (300 MHz, CDCl$_3$) δ 8.25 (d, J=2.4 Hz, 1H), 8.13 (dd, J=2.4, 8.1 Hz, 1H), 7.41 (d, J=8.1 Hz, 1H), 3.78 (s, 2H), 2.48 (s, 3H).

2-(2-Methyl-5-nitrophenyl)ethanenitrile 12 (87 g, 494 mmol) was dissolved in methanol:water=1:1 (1.2 L). Potassium hydroxide (277 g, 4.94 mol) in water (1 L) was added and the reaction was heated at reflux for 14 h. After cooling to rt and removing the methanol in vacuo, the aqueous layer was washed with DCM and ether. The combined organic layer was washed with brine, dried over sodium sulfate, and filtered. After removing the solvent in vacuo, the product 13 was obtained as an orange solid. $^1$H NMR (300 MHz, CDCl$_3$) δ 8.07 (m, 2H), 7.35 (d, J=8.1 Hz, 1H), 3.78 (s, 2H), 2.43 (s, 3H).

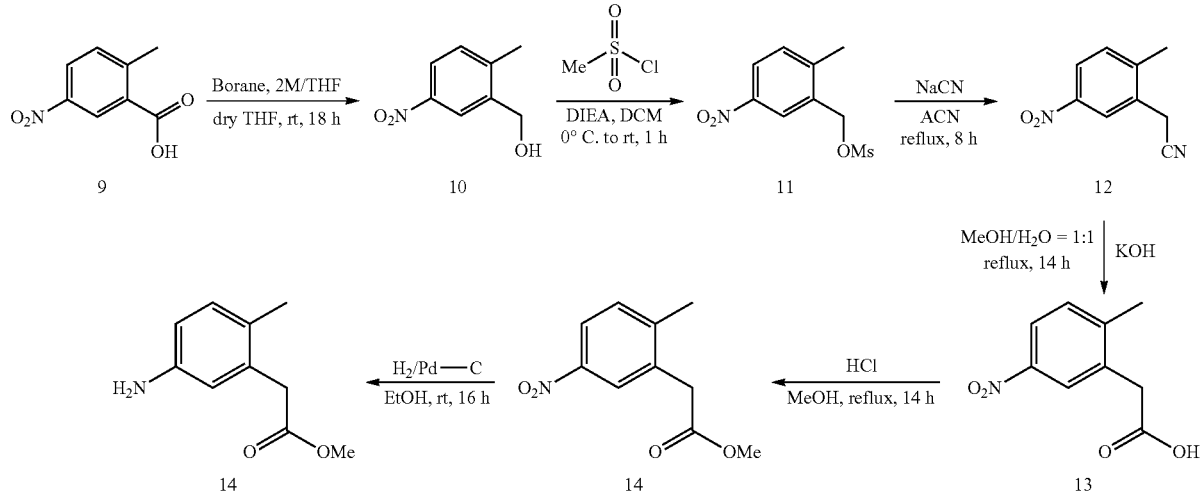

2-Methyl-5-nitrobenzoic acid 9 (125 g, 690 mmol) was dissolved in anhydrous THF (1.25 L). After adding borane (517 mL of a 2 M solution in THF, 1.04 mol), the reaction was stirred at rt for 18 h. The reaction was quenched using an aqueous solution of potassium carbonate (112.5 g in 2.5 L). After removing THF in vacuo, the aqueous solution was extracted with DCM and the combined organic layer was washed with brine and dried over sodium sulfate. After filtering and removing the solvent in vacuo, the product 10 was obtained as a pale yellow solid. $^1$H NMR (300 MHz, CDCl$_3$) δ 8.29 (d, J=3 Hz, 1H), 8.50 (m, 1H), 7.29 (m, 1H), 4.78 (s, 2H), 2.41 (s, 3H).

(2-Methyl-5-nitrophenyl)methanol 10 (96 g, 574 mmol) was dissolved in anhydrous DCM (2.5 L), cooled to 0° C., 2-(2-Methyl-5-nitrophenyl)acetic acid 13 (30 g, 154 mmol) was dissolved in methanol (700 mL) and HCl (79 mL of a 4 M solution in 1,4-dioxane, 316 mmol) was added. The reaction was heated to reflux for 14 h. After cooling to rt and removing solvent in vacuo, the crude product was dissolved in of water (500 mL) and basified to pH>12 using 2N sodium hydroxide. The solution was extracted using ethyl acetate and the combined organic layer was washed with brine, dried over sodium sulfate and filtered. After removing the solvent in vacuo, the product 14 was obtained as a dark yellow solid. $^1$H NMR (300 MHz, CDCl$_3$) δ 8.06 (m, 2H), 7.33 (d, J=8.4 Hz, 1H), 3.73 (s, 3H), 3.72 (s, 2H), 2.41 (s, 3H).

2-(2-Methyl-5-nitrophenyl)acetic acid methyl ester 14 (32 g, 153 mmol) was dissolved in ethanol (750 mL). To this solution was added 10% palladium on carbon (3.2 g). After the mixture was degassed, a balloon filled with hydrogen was fitted. The reaction was stirred at rt for 16 h. After removing the catalyst by filtering through a celite plug and removing the solvent in vacuo, the crude product was purified using flash chromatography (ethyl acetate:petroleum ether=5:1). The product 7 was isolated as a yellow oil. ¹H NMR (300 MHz, CDCl₃) δ 6.9 (d, J=7.8 Hz), 6.59 (m, 1H), 6.56 (m, 1H), 3.69 (s, 3H).

Synthesis of 3-(5-amino-2-methylphenyl)-1,7-dimethyl-1,6-naphthyridin-2(1H)-one (15)

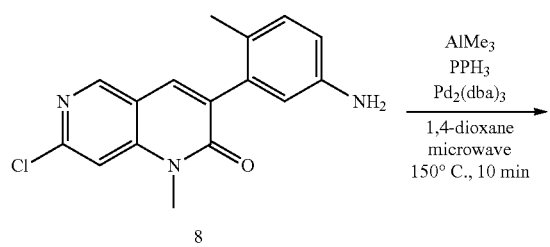

To a solution of 3-(5-amino-2-methylphenyl)-7-chloro-1-methyl-1,6-naphthyridin-2-one 8 (0.53 mmol) in dioxane (3 mL) was added triphenylphosphine (0.08 mmol), Pd₂(dba)₃ (16 umol) and trimethylaluminum (0.8 mL of a 2.0 M solution in toluene). The mixture was degassed for 10 minutes. The reaction vial was sealed and heated via microwave for 10 minutes at 150° C. The reaction was cooled to rt and poured into 1M HCl (30 mL) and washed with EtOAc. The aqueous layer was made basic with 3M NaOH and extracted with EtOAc (3×20 mL). The combined organic layers were dried over magnesium sulfate, filtered and reduced to dryness by evaporation. The crude yellow oil was purified by flash chromatography on silica with DCM containing 3-5% MeOH as eluant to yield a yellow glassy solid 15. ¹H NMR (400 MHz, CDCl₃) δ 8.67 (s, 1H), 7.63 (s, 1H), 7.08 (s, 1H), 7.05 (d, J=8.4 Hz, 1H), 6.65 (dd, J=8.4, 2.4 Hz, 1H), 6.57 (d, J=2.4 Hz, 1H), 3.72 (s, 3H), 2.70 (s, 3H), 2.11 (s, 3H). MS m/z (M+1)⁺: 280.1.

Synthesis of 3-(5-amino-2-methylphenyl)-7-ethyl-1-methyl-1,6-naphthyridin-2(1H)-one (15a)

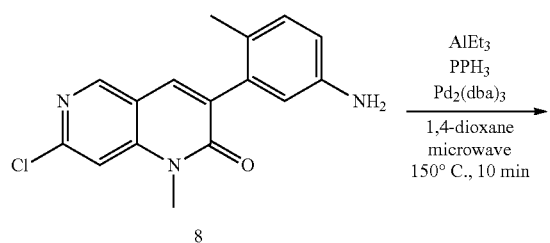

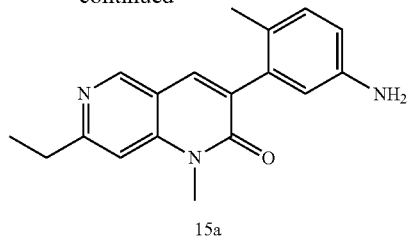

Starting from 8 (1.0 mmol), 3-(5-amino-2-methylphenyl)-7-ethyl-1-methyl-1,6-naphthyridin-2(1H)-one (15a) was prepared and purified in an identical fashion as (15) to give a yellow solid. MS m/z (M+1)⁺: 294.1.

Synthesis of (E)-1-(3-(1,7-dimethyl-2-oxo-1,2-dihydro-1,6-naphthyridin-3-yl)-4-methylphenyl)-2-hydroxyguanidine (17)

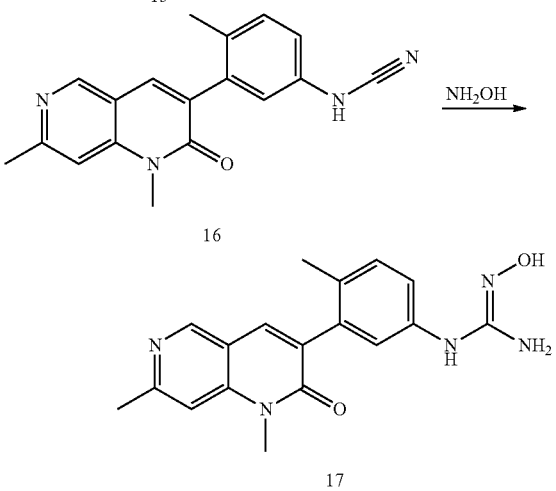

To a solution of cyanogen bromide (0.08 g, 0.7 mmol, 1.0 eq.) in anhydrous methanol (3 mL) was added potassium acetate (0.21 g, 2.1 mmol, 3.0 eq.) and cooled to 0° C. Subsequently a solution of aniline 15 (0.2 g, 0.7 mmol, 1.0 eq.) in anhydrous methanol (2 mL) was added. After addition, the reaction was warmed to rt and stirred for an additional 3 h. Complete consumption of the aniline 15 was monitored by LC/MS, at which time the reaction was diluted with DCM (30 mL) and washed with water and brine. The organic layer was dried over magnesium sulfate, filtered and solvent removed. The crude cyanamide 16 was used in the following step without further purification.

To a solution of the crude cyanamide 16 (0.22 g, 0.7 mmol) in absolute ethanol (10 mL) was added hydroxylamine (0.07 mL, 1.5 eq of a 50% aqueous solution). The reaction was stirred at rt for 12 h. The solvent was evaporated to dryness and the crude residue dissolved in DCM (10-15 mL) and cooled to 0° C. The resulting precipitate was filtered, washed with cold DCM and dried to yield 17 as a yellow precipitate. ¹H NMR (400 MHz, d₆-DMSO) δ 8.78 (s, 1H), 8.31 (s, 1H), 7.87 (s, 1H), 7.55 (s, 1H), 7.41 (s, 2H), 7.28 (dd, J=8, 2 Hz, 1H), 7.15 (d, J=2 Hz, 1H), 7.03 (d, J=8 Hz, 1H), 5.02 (s, 2H), 3.64 (s, 3H), 2.61 (s, 3H), 2.01 (s, 3H). MS m/z 338.3 (M+1).

Synthesis of (E)-1-(3-(7-ethyl-1-methyl-2-oxo-1,2-dihydro-1,6-naphthyridin-3-yl)-4-methylphenyl)-2-hydroxyguanidine (17a)

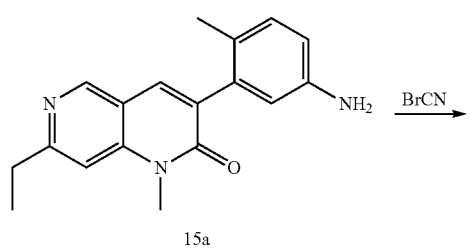

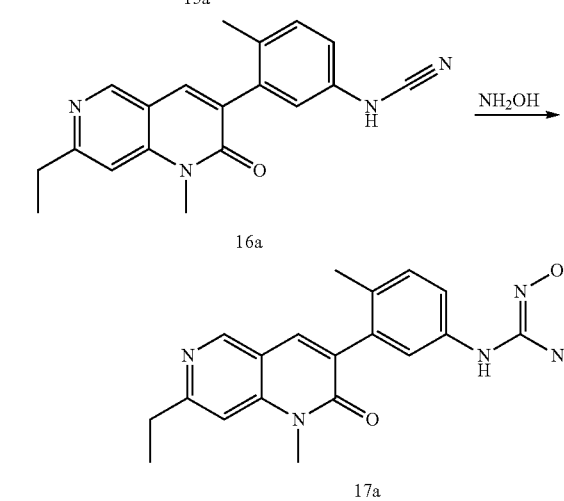

Intermediate 17a was prepared in an identical manner as compound 17 starting from 15a on a 0.3 mmol scale.

Synthesis of N-(3-(1,7-dimethyl-2-oxo-1,2-dihydro-1,6-naphthyridin-3-yl)-4-methylphenyl)-1H-imidazole-1-carboxamide (18)

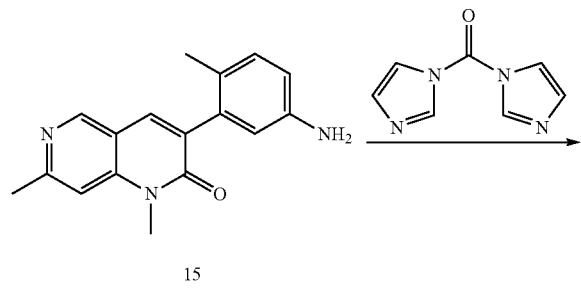

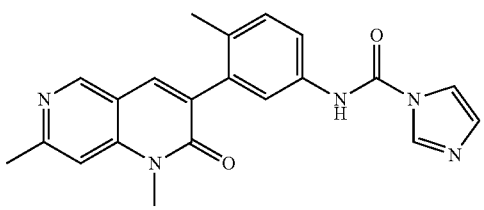

To a solution of 3-(5-amino-2-methylphenyl)-1,7-dimethyl-1,6-naphthyridin-2(1H)-one 15 (22 mg, 0.08 mmol) in ACN (0.5 mL) was added CDI (16 mg, 0.09 mmol). After stirring at rt for 2 h, solvent was removed and the crude N-(3-(1,7-dimethyl-2-oxo-1,2-dihydro-1,6-naphthyridin-3-yl)-4-methylphenyl)-1H-imidazole-1-carboxamide 18 was used without further purification. MS m/z 374.3 (M+1).

Synthesis of 3-(5-isothiocyanato-2-methylphenyl)-1,7-dimethyl-1,6-naphthyridin-2(1H)-one (19)

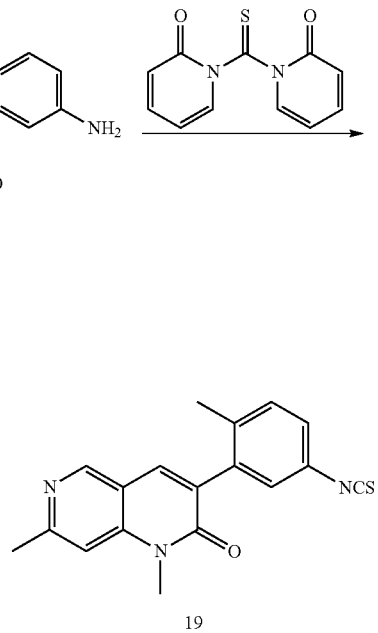

To a solution of 3-(5-amino-2-methylphenyl)-1,7-dimethyl-1,6-naphthyridin-2(1H)-one 15 (280 mg, 1 mmol) in DCM (5 mL) was added 1,1'-thiocarbonyldipyridin-2(1H)-one (233 mg, 1 mmol) at rt. The solvent was removed in vacuo after 1 h. The crude white solid of 3-(5-isothiocyanato-2-methylphenyl)-1,7-dimethyl-1,6-naphthyridin-2(1H)-one 19 was used without further purification. ¹H NMR (400 MHz, CDCl₃) δ 8.64 (s, 1H), 7.18 (d, J=8.0 Hz, 1H), 7.09 (dd, J=2.4, 8.0 Hz, 1H), 7.05 (d, J=2 Hz, 1H), 7.04 (s, 1H), 3.66 (s, 3H), 2.64 (s, 3H), 2.16 (s, 3H). MS m/z 322.2 (M+1).

Synthesis of Compounds of the Invention

Method 1

Example A5

Synthesis of 3-(5-(5-ethyl-1,2,4-oxadiazol-3-ylamino)-2-methylphenyl)-1,7-dimethyl-1,6-naphthyridin-2(1H)-one

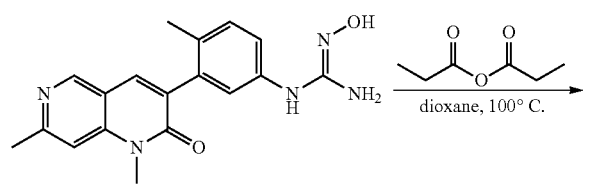

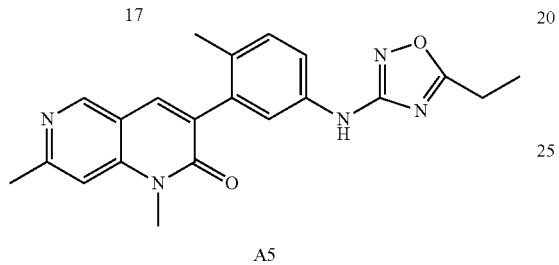

Propionyl anhydride (46 uL, 0.35 mmol) was added to hydroxyguanidine 17 (0.1 g, 0.30 mmol) in dry dioxane (3 mL). The resulting mixture was stirred at 100° C. for 3 h. After cooling and filtration, the mixture was purified by preparative LC/MS to give 3-(5-(5-ethyl-1,2,4-oxadiazol-3-ylamino)-2-methylphenyl)-1,7-dimethyl-1,6-naphthyridin-2(1H)-one (A5). The white solid was suspended in anhydrous DCM and treated with a 2M HCl solution to afford the corresponding HCl salt in quantitative yields. $^1$H NMR (400 MHz, $d_4$-$CH_3OH$) δ 9.08 (s, 1H), 8.04 (s, 1H), 7.45 (s, 1H), 7.34 (dd, J=8.0 and 4.0 Hz, 1H), 7.25 (d, J=8.0 Hz, 1H), 3.82 (s, 3H), 2.85 (s, 3H), 2.85 (q, J=8.0 Hz, 2H), 2.16 (s, 3H), 1.35 (t, J=8.0 Hz, 3H). MS m/z (M+1)$^+$: 376.1.

Method 2

Example A7

Synthesis of 1,7-dimethyl-3-(2-methyl-5-(5-phenyl-1,2,4-oxadiazol-3-ylamino)phenyl)-1,6-naphthyridin-2(1H)-one

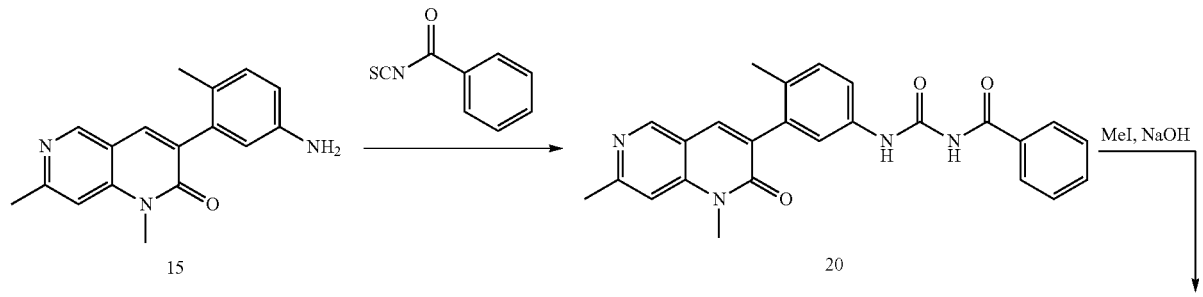

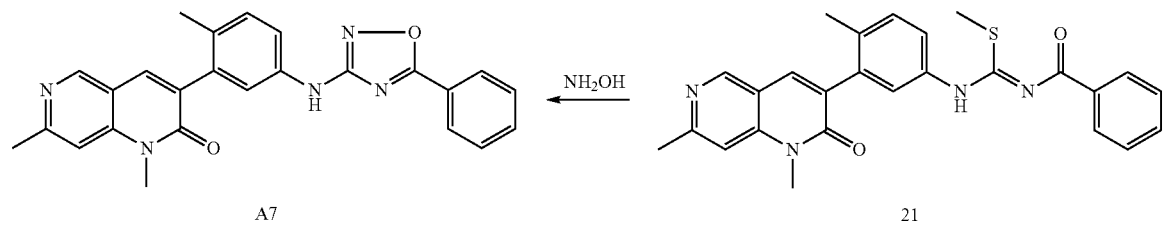

To a solution of 3-(5-amino-2-methylphenyl)-1,7-dimethyl-1,6-naphthyridin-2(1H)-one 15 (280 mg, 1 mmol) in DCM (5 mL) was added benzoyl isothiocyanate (180 mg, 1.1 mmol) at rt. The solvent was removed in vacuo after 10 min. The residue was washed with EtOH to give the desired product N-(3-(1,7-dimethyl-2-oxo-1,2-dihydro-1,6-naphthyridin-3-yl)-4-methylphenylcarbamothioyl)benzamide 20 as a white solid. MS m/z 443.1 (M+1).

To a solution of N-(3-(1,7-dimethyl-2-oxo-1,2-dihydro-1,6-naphthyridin-3-yl)-4-methylphenylcarbamothioyl)benzamide 20 (22 mg, 0.05 mmol) in DCM (0.5 mL) was added solid powder of NaOH (20 mg, 0.5 mmol) and MeI (7 mg, 0.05 mmol). The mixture was stirred at rt for 1 h to yield (Z)-methyl N'-benzoyl-N-(3-(1,7-dimethyl-2-oxo-1,2-dihydro-1,6-naphthyridin-3-yl)-4-methylphenyl)carbamimidothioate 21 after removal of DCM. The crude 21 was used without further purification. MS m/z 457.2 (M+1).

Hydroxylamine hydrochloride (35 mg, 0.5 mmol) and EtOH (1 mL) were added to the crude 21 (0.05 mmol). The mixture was heated at 80° C. for 2 h. After filtration, the mixture was purified by preparative LC/MS to give 1,7-dimethyl-3-(2-methyl-5-(5-phenyl-1,2,4-oxadiazol-3-ylamino)phenyl)-1,6-naphthyridin-2(1H)-one A7. $^1$H NMR (400 MHz, d$_4$-MeOH) δ 9.03 (s, 1H), 8.12 (s, 1H), 8.1 (d, J=1.5 Hz, 1H), 8.05 (s, 1H), 7.83 (s, 1H), 7.65 (d, J=6.2 Hz, 1H), 7.59 (d, J=6.3 Hz, 1H), 7.57 (d, J=7.2 Hz, 1H), 7.5 (d, J=2.4 Hz, 1H), 7.43 (dd, J=8.3, 2.5 Hz, 1H), 7.27 (d, J=8.4 Hz, 1H), 3.84 (s, 3H), 2.83 (s, 3H), 2.18 (s, 3H). MS m/z 424.1 (M+1).

Example A6

Synthesis of 3-(5-(5-isopropyl-1,2,4-oxadiazol-3-ylamino)-2-methylphenyl)-1,7-dimethyl-1,6-naphthyridin-2(1H)-one

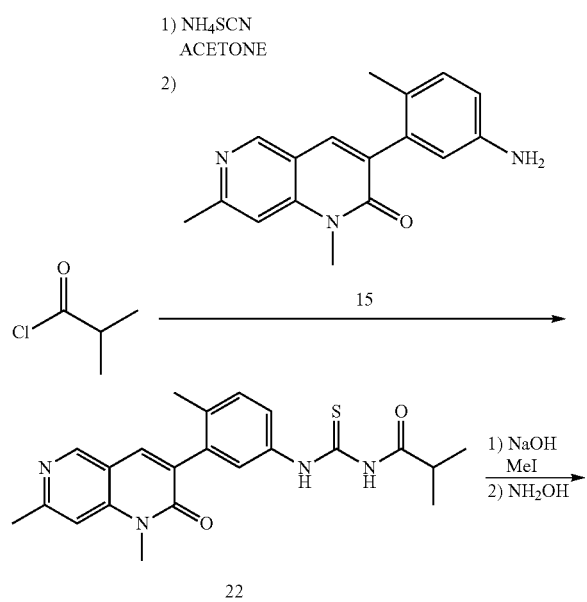

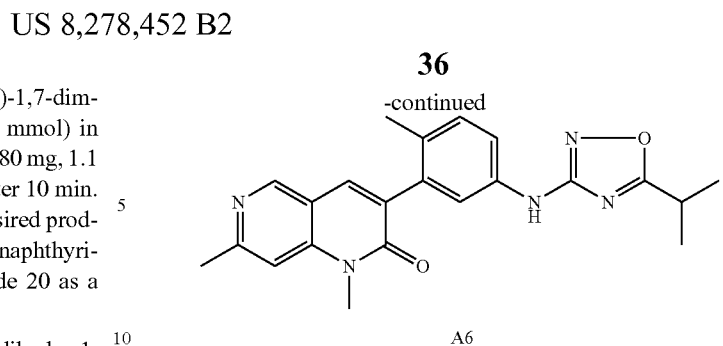

A6

The mixture of isobutyryl chloride (160 mg, 1.5 mmol) and ammonium isothiocyanate (114.2 mg, 1.5 mmol) in acetone (2.0 mL) was heated at 40° C. for 3 h. To the above reaction mixture, 3-(5-amino-2-methylphenyl)-1,7-dimethyl-1,6-naphthyridin-2(1H)-one (15) (419 mg, 1.5 mmol) was added at rt and stirred for 30 min. The solvent was removed under vacuum to yield N-(3-(1,7-dimethyl-2-oxo-1,2-dihydro-1,6-naphthyridin-3-yl)-4-methylphenylcarbamothioyl)isobutyramide 22, which was used without purification. MS m/z 409.2 (M+1).

To the crude N-(3-(1,7-dimethyl-2-oxo-1,2-dihydro-1,6-naphthyridin-3-yl)-4-methylphenylcarbamothioyl)isobutyramide 22 obtained above in EtOH (2.0 mL), NaOH (180 mg, 4.5 mmol) and MeI (213 mg, 1.5 mmol) were added and the resulting mixture was stirred at rt for 1 h. Then hydroxylamine hydrochloride (313 mg, 4.5 mmol) was added and the reaction mixture was heated at 80° C. for 30 min. HPLC and Prep-TLC purifications gave 3-(5-(5-isopropyl-1,2,4-oxadiazol-3-ylamino)-2-methylphenyl)-1,7-dimethyl-1,6-naphthyridin-2(1H)-one (A6). $^1$H NMR (400 MHz, CDCl$_3$) δ 8.62 (s, 1H), 7.62 (s, 1H), 7.22-7.26 (m, 2H), 7.14-7.18 (m, 1H), 7.02 (s, 1H), 3.66 (s, 3H), 3.05 (s, 3H), 2.12 (s, 3H), 1.31 (d, J=7.2 Hz, 6H). MS m/z 390.1 (M+1).

Method 3

Example A7

Synthesis of 1,7-dimethyl-3-(2-methyl-5-(5-phenyl-1,2,4-oxadiazol-3-ylamino)phenyl)-1,6-naphthyridin-2(1H)-one

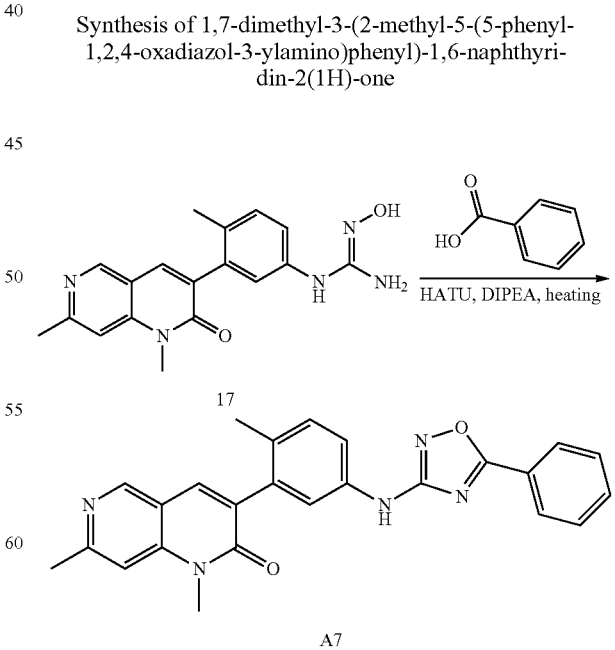

A7

To a solution of benzoic acid (0.67 g, 5.5 mmol), HATU (2.09 g, 11 mmol) and DIPEA (1.05 mL, 6 mmol) in dry DMF (10 mL) at rt in the presence of anhydrous Na$_2$SO$_4$ (7 g, 50 mmol) was added 17 (1.69 g, 5 mmol) slowly. The consumption of 17 was determined to be completed by LC/MS. Additional anhydrous DMF (40 mL) was added and the mixture was heated at 100° C. for 1 h. Solid was filtered off and most of DMF was removed under vacuum. The residue was partitioned between a mixture of water (150 mL), aqueous Na$_2$CO$_3$ (2 M, 10 mL), EtOAc (200 mL) and MeOH (20 mL). The organic phase was washed further with water (2×50 mL). After drying and removal of EtOAc, the solid residue was suspended and stirred in ACN (40 mL) for 16 h. Filtration and washing with copies amounts of ACN yielded A7 as a solid. $^1$H NMR (400 MHz, d$_4$-MeOH) δ 9.03 (s, 1H), 8.12 (s, 1H), 8.1 (d, J=1.5 Hz, 1H), 8.05 (s, 1H), 7.83 (s, 1H), 7.65 (d, J=6.2 Hz, 1H), 7.59 (d, J=6.3 Hz, 1H), 7.57 (d, J=7.2 Hz, 1H), 7.5 (d, J=2.4 Hz, 1H), 7.43 (dd, J=8.3, 2.5 Hz, 1H), 7.27 (d, J=8.4 Hz, 1H), 3.84 (s, 3H), 2.83 (s, 3H), 2.18 (s, 3H). MS m/z 424.1 (M+1).

Example A32

Synthesis of 3-(5-(5-(2-hydroxypropan-2-yl)-1,2,4-oxadiazol-3-ylamino)-2-methylphenyl)-1,7-dimethyl-1,6-naphthyridin-2(1H)-one

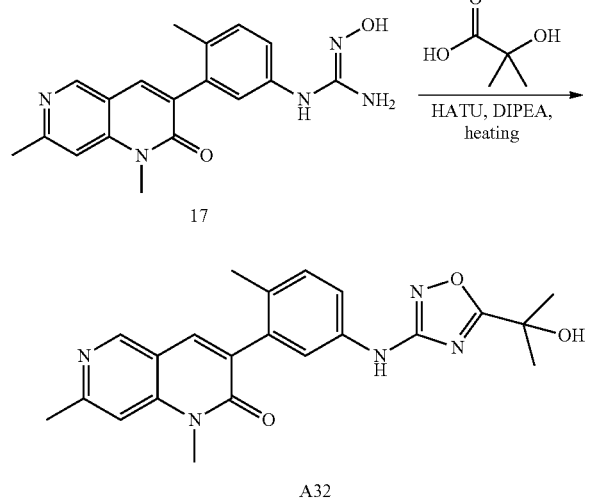

2-Hydroxy-2-methylpropanoic acid (16.1 mg, 0.15 mmol), HATU (59 mg, 0.15 mmol), and DIPEA (0.027 mL, 0.15 mmol) were stirred in dry DMF (3 mL) for 1 h before 17 (50 mg, 0.14 mmol) was added at rt. The stirring was continued for 1 h before it was heated at 100° C. for 5 h. After cooling and filtration, the mixture was purified by preparative LC/MS to give 3-(5-(5-(2-hydroxypropan-2-yl)-1,2,4-oxadiazol-3-ylamino)-2-methylphenyl)-1,7-dimethyl-1,6-naphthyridin-2(1H)-one (A32) as a solid. $^1$H NMR (400 MHz, d$_4$-MeOH) δ 8.90 (s, 1H), 7.94 (s, 1H), 7.81 (s, 1H), 7.62 (dd, J=8, 4 Hz, 1H), 7.52 (d, J=8, 4 Hz, 1H), 7.35 (d, J=4 Hz, 1H), 7.26 (dd, J=8, 4 Hz, 1H), 7.14 (d, J=8 Hz, 1H), 3.79 (s, 3H), 2.75 (s, 3H), 2.06 (s, 3H), 1.35 (m, 6H). MS m/z 406.2 (M+1).

Example A34

Synthesis of 1,7-dimethyl-3-(2-methyl-5-(5-(1-methylcyclopropyl)-1,2,4-oxadiazol-3-ylamino)phenyl)-1,6-naphthyridin-2(1H)-one

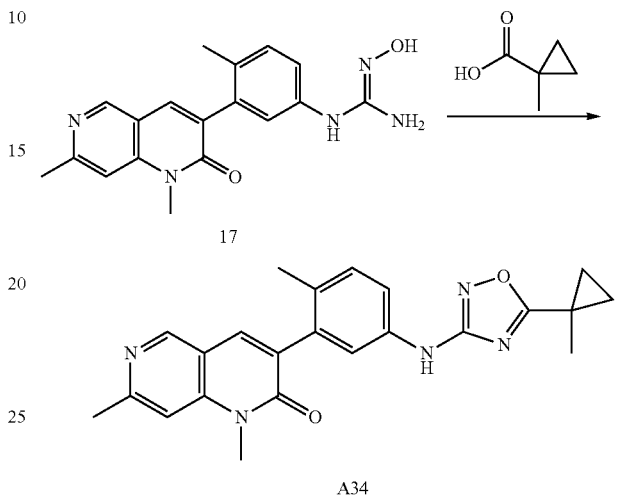

To a solution of 1-methylcyclopropanecarboxylic acid (6 mg, 0.06 mmol) in DMF (1 mL) were added DIPEA (31 μL, 0.18 mmol) and HATU (23 mg, 0.06 mmol). After stirring at rt for 15 min, 17 (20 mg, 0.06 mmol) was added as a solution in DMF (0.5 mL). The reaction was stirred at rt until complete consumption of 17 was determined by LC/MS and then heated at 100° C. for 1 h. Subsequently the reaction was cooled to rt, filtered and purified by preparative LC/MS to give 1,7-dimethyl-3-(2-methyl-5-(5-(1-methylcyclopropyl)-1,2,4-oxadiazol-3-ylamino)phenyl)-1,6-naphthyridin-2(1H)-one (A34) as an off white solid. $^1$H NMR (400 MHz, d$_6$-DMSO) δ 9.87 (s, 1H), 9.13 (s, 1H), 8.05 (s, 1H), 7.87 (s, 1H), 7.37 (dd, J=8, 2 Hz, 1H), 7.30 (d, J=2 Hz, 1H), 7.22 (d, J=8 Hz, 2H), 3.70 (s, 3H), 2.75 (s, 3H), 2.07 (s, 3H), 1.47 (s, 3H), 1.27 (m, 2H), 1.08 (m, 2H). MS m/z 402.4 (M+1).

Example A35

Synthesis of 3-(5-(5-(1-hydroxy-2-methylpropan-2-yl)-1,2,4-oxadiazol-3-ylamino)-2-methylphenyl)-1,7-dimethyl-1,6-naphthyridin-2(1H)-one

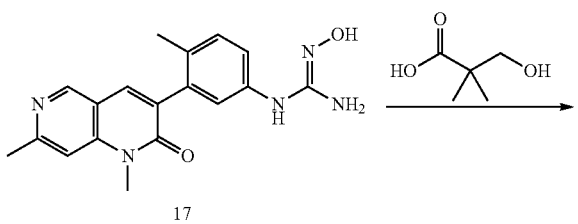

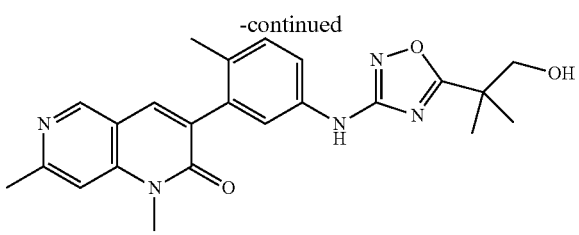

A35

To a solution of 3-hydroxy-2,2-dimethylpropanoic acid (88 mg, 0.7 mmol) in DMF (5 mL) were added DIPEA (0.26 mL, 1.5 mmol) and HATU (0.21 g, 0.7 mmol). After stirring at rt for 15 min, 17 (0.25 g, 0.7 mmol) was added as a solution in DMF (2 mL). The reaction was stirred at rt until complete consumption of 17 was determined by LC/MS and then was heated at 100° C. for 2 h. Subsequently the reaction was cooled to rt, partitioned with EtOAc (30 mL) and 5% aq NaHCO₃ (20 mL). The aqueous layer was extracted with fresh EtOAc (2×20 mL). The combined organic layers were dried over magnesium sulfate, filtered and reduced to dryness. The crude material was purified by flash column chromatography on silica with DCM/4% MeOH as eluant to give 3-(5-(5-(1-hydroxy-2-methylpropan-2-yl)-1,2,4-oxadiazol-3-ylamino)-2-methylphenyl)-1,7-dimethyl-1,6-naphthyridin-2(1H)-one (A35) as a clear glassy solid. ¹H NMR (400 MHz, d₆-DMSO) δ 9.86 (s, 1H), 8.81 (s, 1H), 7.93 (s, 1H), 7.43 (s, 1H), 7.37 (dd, J=8, 2 Hz, 1H), 7.28 (d, J=2 Hz, 1H), 7.21 (d, J=8 Hz, 2H), 5.10 (t, J=5.5 Hz, 1H), 3.65 (s, 3H), 3.55, (d, J=5.5 Hz, 1H) 2.61 (s, 3H), 2.07 (s, 3H), 1.31 (s, 6H). MS m/z 420.4 (M+1).

Example A51

Synthesis of 1,7-dimethyl-3-(2-methyl-5-(5-(6-methylpyridin-3-yl)-1,2,4-oxadiazol-3-ylamino)phenyl)-1,6-naphthyridin-2(1H)-one

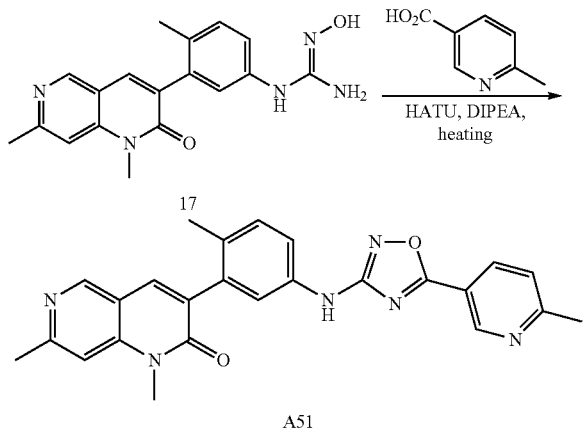

6-Methylnicotinic acid (0.67 g, 4.89 mmol), HATU (1.86 g, 4.89 mmol), and DIPEA (0.85 mL, 4.89 mmol) were stirred in dry DMF (20 mL) for 1 h before 17 (1.5 g, 4.44 mmol) was added at rt. The stirring was continued for 1 h before it was heated at 100° C. for 5 h. After cooling and filtration, the mixture was purified by preparative LC/MS to give 1,7-dimethyl-3-(2-methyl-5-(5-(6-methylpyridin-3-yl)-1,2,4-oxadiazol-3-ylamino)phenyl)-1,6-naphthyridin-2(1H)-one (A51) as a solid. ¹H NMR (400 MHz, d6-DMSO) δ 9.27 (d, J=2.0 Hz, 1H), 9.10 (s, 1H), 8.73 (dd, J=2.0, 8.4 Hz, 1H), 8.07 (s, 1H), 7.94 (s, 1H), 7.85 (d, J=8.4 Hz, 1H), 7.50 (d, J=2.4 Hz, 1H), 7.46 (dd, J=2.4, 8.4 Hz, 1H), 7.29 (d, J=8.4 Hz, 1H), 3.85 (s, 3H), 2.87 (s, 3H), 2.79 (s, 3H), 2.19 (s, 3H). MS m/z 439.2 (M+1).

Example A52

Synthesis of 1,7-dimethyl-3-(2-methyl-5-(5-(pyridin-2-yl)-1,2,4-oxadiazol-3-ylamino)phenyl)-1,6-naphthyridin-2(1H)-one

A52

To a solution of picolinic acid (1.35 g, 11 mmol), HATU (4.18 g, 11 mmol) and DIPEA (2.09 mL, 12 mmol) in dry DMF (50 mL) at rt in the presence of anhydrous Na₂SO₄ (7 g, 50 mmol) was added 17 (3.37 g, 10 mmol) slowly. The consumption of 17 was determined to be completed by LC/MS. Additional anhydrous DMF (50 mL) was added and the mixture was heated at 100° C. for 16 h. Solid was filtered off and most of DMF was removed under vacuum. The residue was partitioned between a mixture of water (200 mL), aqueous Na₂CO₃ (2 M, 20 mL), EtOAc (300 mL) and MeOH (30 mL). The organic phase was washed further with water (2×50 mL). After drying and removal of EtOAc, the residue was treated with mixtures of DCM/MeOH (30 mL/3 mL) and washed with DCM to yield A52 as a solid precipitate (1.4 g). The mother liquor was purified by silica gel chromatography (8% MeOH in DCM) to remove most impurities. Most fractions containing product were combined to obtain solid product which was further triturated in ACN (60 mL) and washed several time with ACN to give 0.9 g of product A52. Fractions containing some product but more impurities were combined to get a crude residue which was purified with preparative HPLC to recover an additional 0.3 g A52. All three batches of 1,7-dimethyl-3-(2-methyl-5-(5-(pyridin-2-yl)-1,2,4-oxadiazol-3-ylamino)phenyl)-1,6-naphthyridin-2(1H)-one (A52) had identical NMR and LC/MS. ¹H NMR (400 MHz, d₆-DMSO) δ 10.1 (s, 1H), 8.83 (m, 2H), 8.18 (dt, J=8.8, 1 Hz, 1H), 8.1 (td, J=7.7, 1.7 Hz, 1H), 7.97 (s, 1H), 7.71 (ddd, J=7.6, 4.8, 1.2 Hz, 1H), 7.47 (dd, J=8.3, 2.4 Hz, 1H), 7.44 (s, 1H), 7.37 (d, J=2.4 Hz, 1H), 7.25 (d, J=8.5 Hz, 1H), 3.66 (s, 3H), 3.34 (s, 3H), 2.01 (s, 3H). MS m/z 425.1 (M+1).

Example A54

Synthesis of 3-(5-(5-(1,1-difluoroethyl)-1,2,4-oxadiazol-3-ylamino)-2-methylphenyl)-1,7-dimethyl-1,6-naphthyridin-2(1H)-one

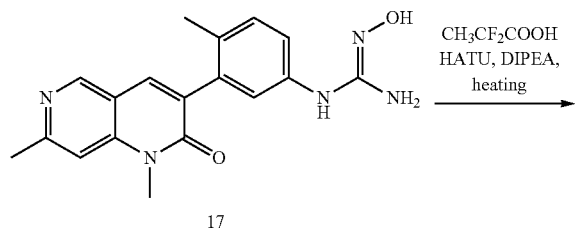

17

CH₃CF₂COOH
HATU, DIPEA,
heating

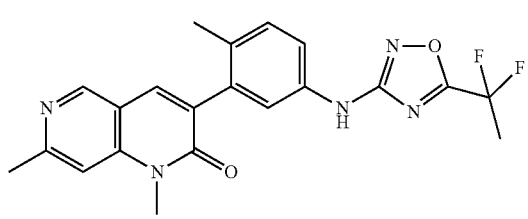

A54

To a solution of 2,2-difluoropropanoic acid (11 mg, 0.1 mmol), HATU (42 mg, 0.11 mmol) and DIPEA (15 mg, 0.12 mmol) in dry DMF (0.5 mL) at rt in the presence of anhydrous Na₂SO₄ (71 mg, 0.5 mmol) were added 17 (33.7 mg, 0.10 mmol) slowly. The consumption of 17 was determined to be completed by LC/MS. The mixture was heated at 100° C. for 2 h. Solid was filtered off and the residue was purified with preparative HPLC to yield 3-(5-(5-(1,1-difluoroethyl)-1,2,4-oxadiazol-3-ylamino)-2-methylphenyl)-1,7-dimethyl-1,6-naphthyridin-2(1H)-one (A54). $^1$H NMR (400 MHz, DMSO-d₆) δ 10.27 (s, 1H), 9.00 (s, 1H), 8.03 (s, 1H), 7.70 (s, 1H), 7.42 (d, J=8.4 Hz, 1H), 7.33 (s, 1H), 7.27 (d, J=8.0 Hz, 1H), 2.70 (s, 3H), 2.51 (s, 3H), 2.16 (t, J=19.6 Hz, 3H), 2.10 (s, 3H). MS m/z 412.2 (M+1).

Example A56

Synthesis of 3-(5-(5-(2-hydroxy-2-methylpropyl)-1,2,4-oxadiazol-3-ylamino)-2-methylphenyl)-1,7-dimethyl-1,6-naphthyridin-2(1H)-one

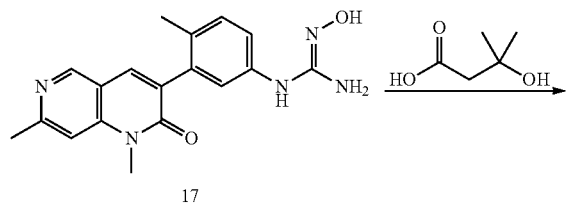

17

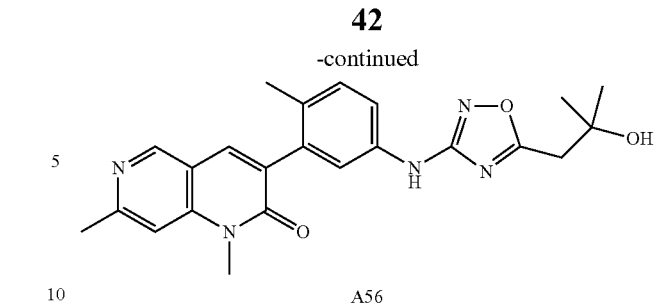

A56

To a solution of 3-hydroxy-3-methylbutanoic acid (6 mg, 0.06 mmol) in DMF (1 mL) were added DIPEA (31 μL, 0.18 mmol) and HATU (23 mg, 0.06 mmol). After stirring at rt for 15 min, 17 (20 mg, 0.06 mmol) was added as a solution in DMF (0.5 mL). The reaction was stirred at rt until complete consumption of 17 was determined by LC/MS and then heated at 100° C. for 1 h. Subsequently the reaction was cooled to rt, filtered and purified by preparative LC/MS to give 3-(5-(5-(2-hydroxy-2-methylpropyl)-1,2,4-oxadiazol-3-ylamino)-2-methylphenyl)-1,7-dimethyl-1,6-naphthyridin-2(1H)-one (A56). MS m/z 420.4 (M+1).

Example A57

Synthesis of 3-(5-(5-(1-hydroxycyclopropyl)-1,2,4-oxadiazol-3-ylamino)-2-methylphenyl)-1,7-dimethyl-1,6-naphthyridin-2(1H)-one

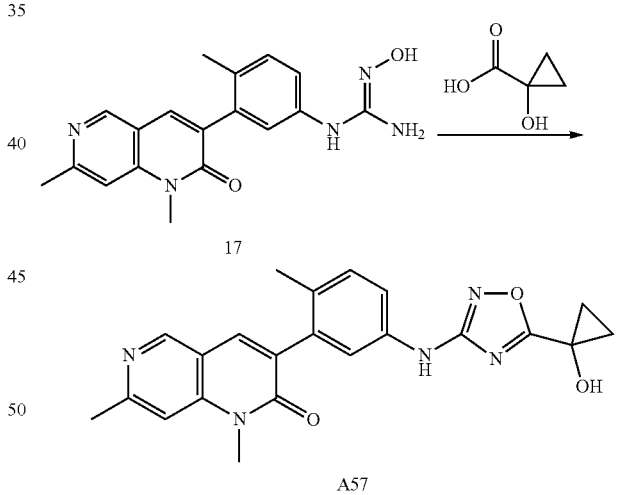

A57

To a solution of 1-hydroxycyclopropanecarboxylic acid (6 mg, 0.06 mmol) in DMF (1 mL) were added DIPEA (31 μL, 0.18 mmol) and HATU (23 mg, 0.06 mmol). After stirring at rt for 15 min, 17 (20 mg, 0.06 mmol) was added as a solution in DMF (0.5 mL). The reaction was stirred at rt until complete consumption of 17 was determined by LC/MS and then heated at 100° C. for 1 h. Subsequently the reaction was cooled to rt, filtered and purified by preparative LC/MS to give 3-(5-(5-(1-hydroxycyclopropyl)-1,2,4-oxadiazol-3-ylamino)-2-methylphenyl)-1,7-dimethyl-1,6-naphthyridin-2(1H)-one (A57). MS m/z 404.4 (M+1).

Example A58

Synthesis of 1,7-dimethyl-3-(2-methyl-5-(5-(1-(trifluoromethyl)cyclopropyl)-1,2,4-oxadiazol-3-ylamino)phenyl)-1,6-naphthyridin-2(1H)-one

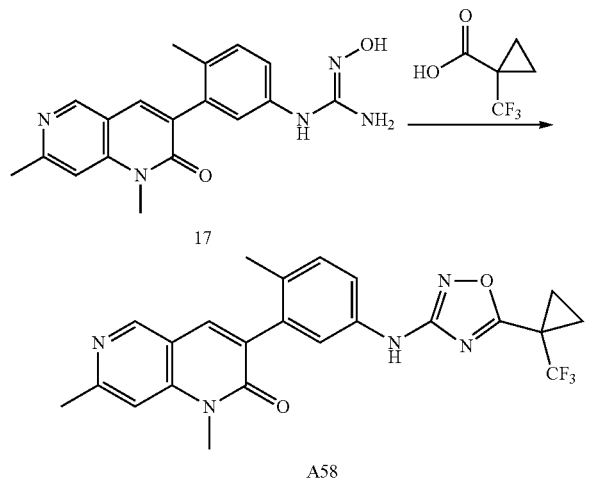

To a solution of 1-(trifluoromethyl)cyclopropanecarboxylic acid (9 mg, 0.06 mmol) in DMF (1 mL) were added DIPEA (31 μL, 0.18 mmol) and HATU (23 mg, 0.06 mmol). After stirring at rt for 15 min 17 (20 mg, 0.06 mmol) was added as a solution in DMF (0.5 mL). The reaction was stirred at rt until complete consumption of 17 was determined by LC/MS and then heated at 100° C. for 1 h. Subsequently the reaction was cooled to rt, filtered and purified by preparative LC/MS to give 1,7-dimethyl-3-(2-methyl-5-(5-(1-(trifluoromethyl)cyclopropyl)-1,2,4-oxadiazol-3-ylamino)phenyl)-1,6-naphthyridin-2(1H)-one (A58). MS m/z 456.6 (M+1).

Example A64

Synthesis of 3-(5-(5-(1-hydroxy-2-methylpropyl)-1,2,4-oxadiazol-3-ylamino)-2-methylphenyl)-1,7-dimethyl-1,6-naphthyridin-2(1H)-one

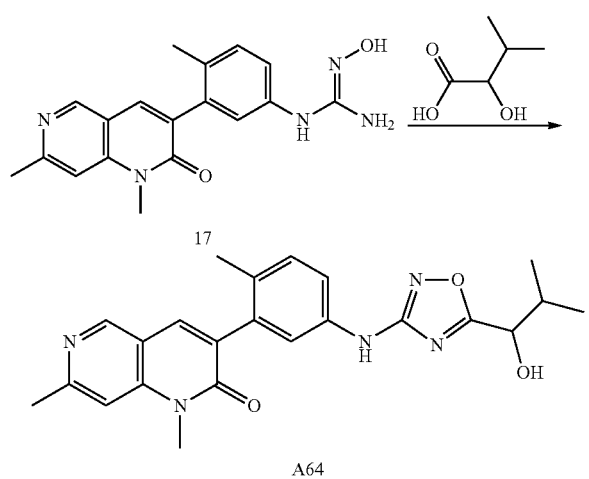

To a solution of 2-hydroxy-3-methylbutanoic acid (70 mg, 0.6 mmol) in DMF (6 mL) were added DIPEA (0.125 mL, 0.7 mmol) and HATU (0.23 g, 0.6 mmol). After stirring at rt for 15 min 17 (0.2 g, 0.6 mmol) was added as a solution in DMF (2 mL). The reaction was stirred at rt until complete consumption of 17 was determined by LC/MS and then was heated at 100° C. for 1 h. The reaction was cooled to rt, purified by preparative LCMS to afford crude material, which was further purified by flash column chromatography on silica with DCM/2% MeOH as eluant to give 3-(5-(5-(1-hydroxy-2-methylpropyl)-1,2,4-oxadiazol-3-ylamino)-2-methylphenyl)-1,7-dimethyl-1,6-naphthyridin-2(1H)-one (A64) as an off white solid. $^1$H NMR (400 MHz, CD$_4$OD) δ 8.76 (s, 1H), 7.93 (s, 1H), 7.47 (s, 1H), 7.39 (dd, J=8, 2 Hz, 1H), 7.36 (d, J=2 Hz, 1H), 7.22 (d, J=8 Hz, 1H), 4.51 (d, J=6 Hz, 1H), 3.76 (s, 3H), 2.69 (s, 3H), 2.16 (m, 1H), 2.14 (s, 3H), 1.02 (d, J=6 Hz, 3H), 0.94 (d, J=6 Hz, 3H). MS m/z 420.4 (M+1).

Example A67

Synthesis of 3-(5-(5-(1-hydroxypropan-2-yl)-1,2,4-oxadiazol-3-ylamino)-2-methylphenyl)-1,7-dimethyl-1,6-naphthyridin-2(1H)-one

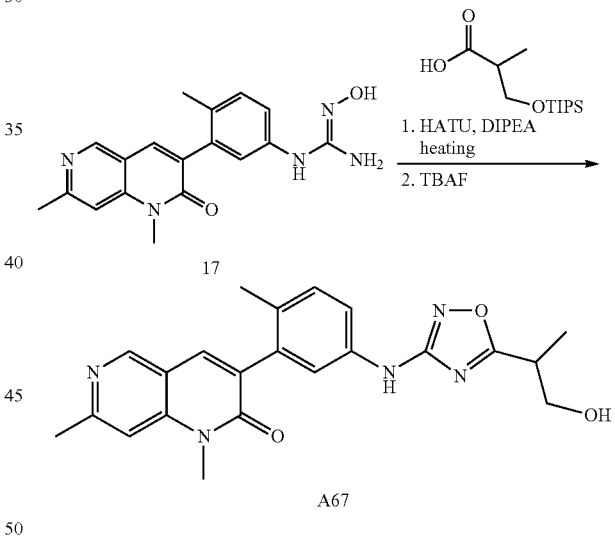

2-Methyl-3-(triisopropylsilyloxy)propanoic acid (34 mg, 0.12 mmol), HATU (50 mg, 0.12 mmol), and DIPEA (0.023 mL, 0.12 mmol) were stirred in dry DMF (3 mL) for 1 h before 17 (40 mg, 0.118 mmol) was added at rt. The stirring was continued for 1 h before it was heated at 100° C. for 5 h. After cooling, TBAF (1 ml, 1 M in THF) was added and stirred for 5 h at rt. After filtration, the mixture was purified by preparative LC/MS to give 3-(5-(5-(1-hydroxypropan-2-yl)-1,2,4-oxadiazol-3-ylamino)-2-methylphenyl)-1,7-dimethyl-1,6-naphthyridin-2(1H)-one (A67) as a solid. $^1$H NMR (400 MHz, d6-DMSO) δ 9.06 (s, 1H), 8.03 (s, 1H), 7.91 (s, 1H), 7.42 (d, J=2.4 Hz, 1H), 7.35 (dd, J=2.4, 8.0 Hz, 1H), 7.23 (d, J=8.4 Hz, 1H), 3.82 (m, 2H), 3.35 (s, 3H), 3.18 (m, 1H), 2.86 (s, 3H), 2.16 (s, 3H), 1.35 (d, J=7.2 Hz, 3H). MS m/z 406.2 (M+1).

Example A68

Synthesis of 3-(5-(5-isobutyl-1,2,4-oxadiazol-3-ylamino)-2-methylphenyl)-1,7-dimethyl-1,6-naphthyridin-2(1H)-one

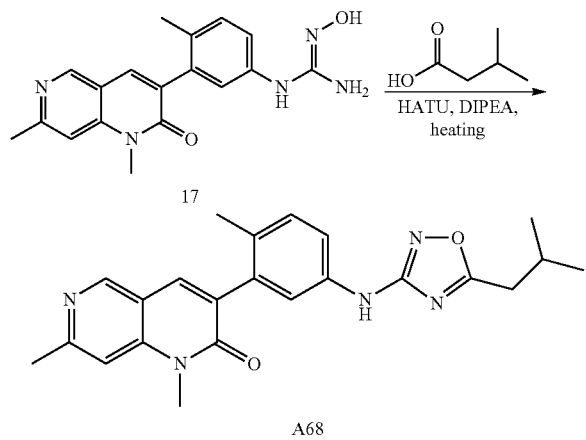

3-Methylbutanoic acid (13 mg, 0.12 mmol), HATU (50 mg, 0.12 mmol), and DIPEA (0.023 mL, 0.12 mmol) were stirred in dry DMF (3 mL) for 1 h before 17 (40 mg, 0.118 mmol) was added at rt. The stirring was continued for 1 h before it was heated at 100° C. for 5 h. After cooling and filtration, the mixture was purified by preparative LC/MS to give 3-(5-(5-isobutyl-1,2,4-oxadiazol-3-ylamino)-2-methylphenyl)-1,7-dimethyl-1,6-naphthyridin-2(1H)-one (A68) as a solid. $^1$H NMR (400 MHz, $d_4$-MeOH) δ 8.92 (s, 1H), 7.92 (s, 1H), 7.73 (s, 1H), 7.33 (d, J=1 Hz, 1H), 7.24 (dd, J=8, 4 Hz, 1H), 7.14 (d, J=4 Hz, 1H), 3.72 (s, 3H), 2.72 (s, 3H), 2.60 (d, J=8 Hz, 2H), 2.10-2.01 (m, 1H), 2.06 (s, 3H), 0.92 (d, J=8 Hz, 6H). MS m/z 403.4, 404.5 (M+1).

Example A69

Synthesis of 3-(5-(5-(1-(hydroxymethyl)cyclopropyl)-1,2,4-oxadiazol-3-ylamino)-2-methylphenyl)-1,7-dimethyl-1,6-naphthyridin-2(1H)-one

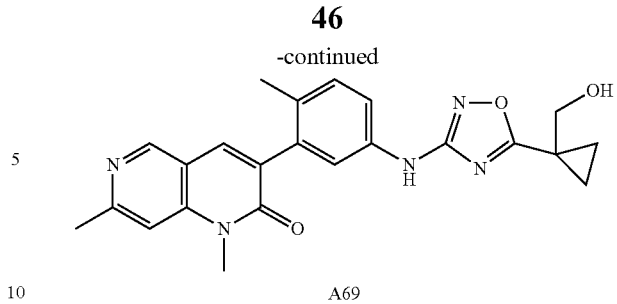

To a solution of 1-(methoxycarbonyl)cyclopropanecarboxylic acid (56 mg, 0.39 mmol), HATU (180 mg, 0.47 mmol) and DIPEA (0.082 mL, 0.47 mmol) in dry DMF (2 mL) at rt in the presence of anhydrous $Na_2SO_4$ (284 mg, 2.0 mmol) was added 17 (130 mg, 0.39 mmol) slowly. The consumption of 17 was determined to be completed by LC/MS. The mixture was heated at 100° C. for 2 h. Solid was filtered off and the residue was dissolved in EtOAc (50 mL). The organic layer was washed with water twice, dried over $Na_2SO_4$, filtered and evaporated to yield a residue which was purified by flash chromatography on silica with 3-5% MeOH in DCM as eluant to yield methyl 1-(3-(3-(1,7-dimethyl-2-oxo-1,2-dihydro-1,6-naphthyridin-3-yl)-4-methylphenylamino)-1,2,4-oxadiazol-5-yl)cyclopropanecarboxylate 23. MS m/z 446.2 (M+1).

To a solution of 1-(3-(3-(1,7-dimethyl-2-oxo-1,2-dihydro-1,6-naphthyridin-3-yl)-4-methylphenylamino)-1,2,4-oxadiazol-5-yl)cyclopropanecarboxylate 23 (100 mg, 0.22 mmol) in MeOH (10 mL), three batches of $NaBH_4$ (66.5 mg, 1.76 mmol) were added during a period of 30 min. After the reaction was determined to be completed by LC/MS, ammonium chloride solution was added to quench the reaction. The resulting mixture was extracted with DCM (50 mL). The organic layer was dried over $Na_2SO_4$, filtered and evaporated to yield a reside which was purified by preparative HPLC to yield 3-(5-(5-(1-(hydroxymethyl)cyclopropyl)-1,2,4-oxadiazol-3-ylamino)-2-methylphenyl)-1,7-dimethyl-1,6-naphthyridin-2(1H)-one (A69). $^1$H NMR (400 MHz, d6-DMSO) δ 9.07 (s, 1H), 8.03 (s, 1H), 7.91 (s, 1H), 7.41 (d, J=2.4 Hz, 1H), 7.33 (dd, J=2.4, 8.4 Hz, 1H), 7.23 (d, J=8.4 Hz, 1H), 3.87 (s, 2H), 3.83 (s, 3H), 2.86 (s, 3H), 2.16 (s, 3H), 1.35 (m, 2H), 1.21 (m, 2H). MS m/z 418.2 (M+1).

Example A73

Synthesis of 3-(5-(5-(3-hydroxycyclopentyl)-1,2,4-oxadiazol-3-ylamino)-2-methylphenyl)-1,7-dimethyl-1,6-naphthyridin-2(1H)-one

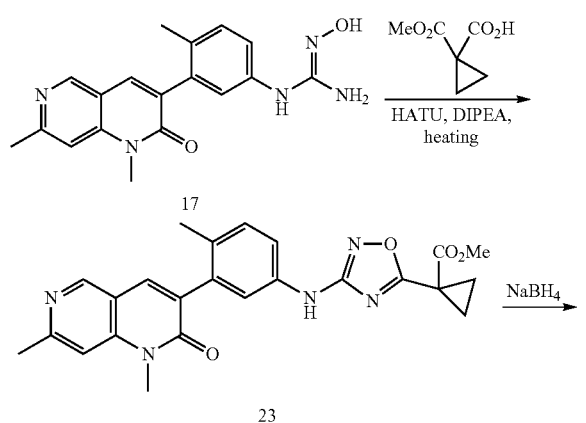

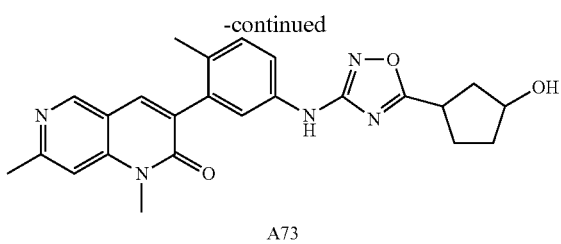

A73

3-Oxocyclopentanecarboxylic acid (16.6 mg, 0.12 mmol), HATU (50 mg, 0.12 mmol), and DIPEA (0.023 mL, 0.12 mmol) were stirred in dry DMF (3 mL) for 1 h before 17 (40 mg, 0.118 mmol) was added at rt. The stirring was continued for 1 h before it was heated at 100° C. for 5 h. After cooling NaBH₄ (20 mg) was added and stirred for 5 h at rt. After filtration, the mixture was purified by preparative LC/MS to give 3-(5-(5-(3-hydroxycyclopentyl)-1,2,4-oxadiazol-3-ylamino)-2-methylphenyl)-1,7-di methyl-1,6-naphthyridin-2(1H)-one (A73) as a solid. MS m/z 431.5, 432.6 (M+1).

Example A76

Synthesis of (S)-3-(5-(5-(1-methoxyethyl)-1,2,4-oxadiazol-3-ylamino)-2-methylphenyl)-1,7-dimethyl-1,6-naphthyridin-2(1H)-one

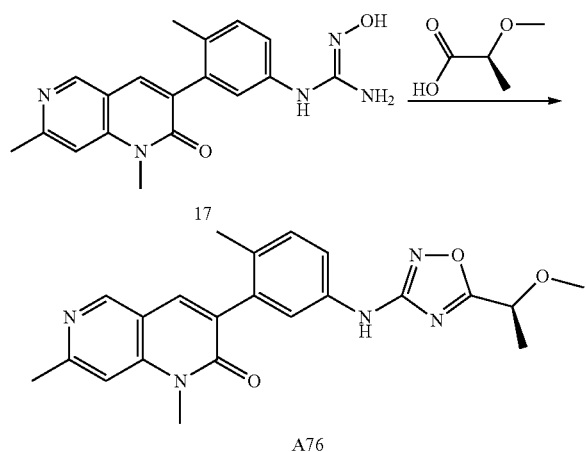

A76

To a solution of (S)-2-methoxypropanoic acid (40 mg, 0.4 mmol) in DMF (4 mL) were added DIPEA (65 µL, 0.4 mmol) and HATU (0.14 g, 0.4 mmol). After stirring at rt for 15 min, 17 (0.13 g, 0.4 mmol) was added as a solution in DMF (1 mL). The reaction was stirred at rt until complete consumption of 17 was determined by LC/MS and then was heated at 100° C. for 3 h. Subsequently, the reaction was cooled to rt, partitioned with EtOAc (30 mL) and 5% aq NaHCO₃ (20 mL). The aqueous layer was extracted with fresh EtOAc (2×20 mL). The combined organic layers were dried over magnesium sulfate, filtered and reduced to dryness. The crude material was purified by flash column chromatography on silica with DCM/2% MeOH as eluant to give (S)-3-(5-(5-(1-methoxyethyl)-1,2,4-oxadiazol-3-ylamino)-2-methylphenyl)-1,7-dimethyl-1,6-naphthyridin-2(1H)-one (A76) as a clear white glassy solid. ¹H NMR (400 MHz, d₆-DMSO) δ 9.94 (s, 1H), 8.81 (s, 1H), 7.94 (s, 1H), 7.43 (s, 1H), 7.40 (dd, J=8, 2 Hz, 1H), 7.30 (d, J=2 Hz, 1H), 7.22 (d, J=8 Hz, 1H), 4.68 (d, J=6 Hz, 1H), 3.65 (s, 3H), 3.45 (s, 3H), 2.61 (s, 3H), 2.07 (s, 3H), 1.49 (d, J=6 Hz, 3H). MS m/z 406.4 (M+1).

Example A77

Synthesis of (S)-1,7-dimethyl-3-(2-methyl-5-(5-(tetrahydrofuran-2-yl)-1,2,4-oxadiazol-3-ylamino)phenyl)-1,6-naphthyridin-2(1H)-one

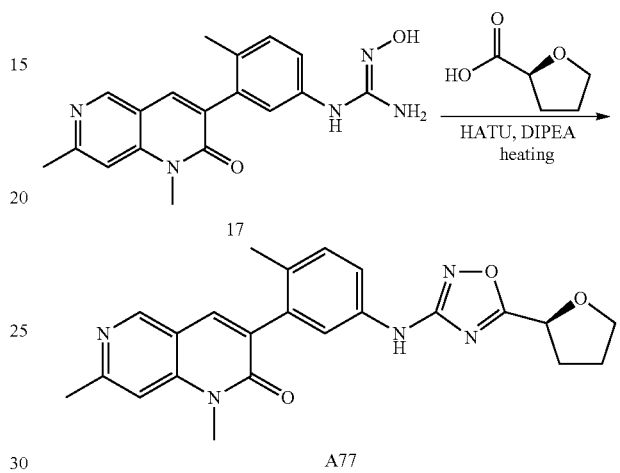

A77

(S)-Tetrahydrofuran-2-carboxylic acid (75.7 mg, 0.65 mmol), HATU (247 mg, 0.65 mmol), and DIPEA (0.11 mL, 0.65 mmol) were stirred in dry DMF (6 mL) for 1 h before 17 (200 mg, 0.59 mmol) was added at rt. The stirring was continued for 1 h before it was heated at 100° C. for 5 h. After cooling and filtration, the mixture was purified by preparative LC/MS to give (S)-1,7-dimethyl-3-(2-methyl-5-(5-(tetrahydrofuran-2-yl)-1,2,4-oxadiazol-3-ylamino)phenyl)-1,6-naphthyridin-2(1H)-one (A77) as a solid. ¹H NMR (400 MHz, d₄-MeOH) δ 9.07 (s, 1H), 8.04 (s, 1H), 7.91 (s, 1H), 7.45 (d, J=4 Hz, 1H), 7.36 (dd, J=8, 4 Hz, 1H), 7.25 (d, J=4 Hz, 1H), 5.10 (dd, J=8, 4 Hz, 1H), 4.03 (dd, J=12, 8 Hz, 1H), 3.96 (dd, J=12, 8 Hz, 1H), 3.83 (s, 3H), 2.85 (s, 3H), 2.41-2.34 (m, 1H), 2.28-2.20 (m, 1H), 2.16 (s, 3H), 2.12-2.03 (m, 2H). MS m/z 417.5, 418.5 (M+1).

Example A92

Synthesis of (R)-3-(5-(5-(1-hydroxy-2-methylpropyl)-1,2,4-oxadiazol-3-ylamino)-2-methylphenyl)-1,7-dimethyl-1,6-naphthyridin-2(1H)-one

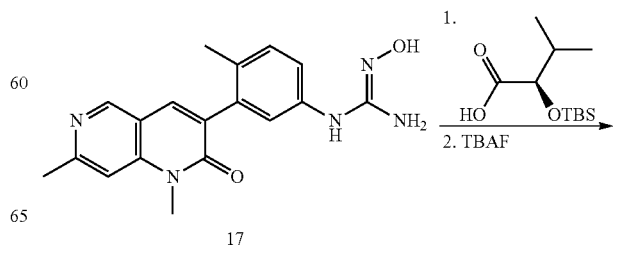

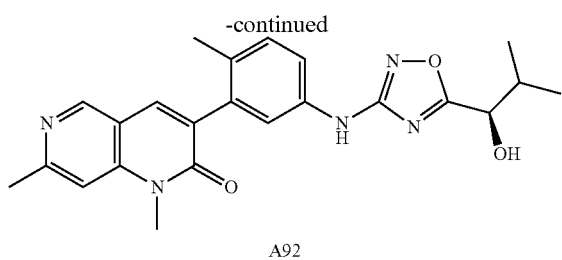

A92

To a solution of (R)-2-(tert-butyldimethylsilyloxy)-3-methylbutanoic acid (83 mg, 0.35 mmol) in DMF (2 mL) were added DIPEA (52 µL, 0.3 mmol) and HATU (0.11 g, 0.3 mmol). After stirring at rt for 15 min, 17 (0.10 g, 0.3 mmol) was added as a solution in DMF (1 mL). The reaction was stirred at rt until complete consumption of 17 was determined by LC/MS and then was heated at 100° C. for 1 h. Subsequently, the reaction was cooled to rt, partitioned with EtOAc (30 mL) and 5% aq NaHCO$_3$ (20 mL). The aqueous layer was extracted with fresh EtOAc (2×20 mL). The combined organic layers were dried over magnesium sulfate, filtered and reduced to dryness. The crude material was dissolved in THF and was added TBAF (2.7 mL of a 1.0 M solution in THF). The mixture was stirred at rt for 2 h. Subsequently the reaction was diluted with EtOAc (20 mL) and washed with water and brine. The organic layer was dried over magnesium sulfate, filtered and reduced to dryness. The crude product was purified by preparative LCMS to give (R)-3-(5-(5-(1-hydroxy-2-methylpropyl)-1,2,4-oxadiazol-3-ylamino)-2-methylphenyl)-1,7-dimethyl-1,6-naphthyridin-2(1H)-one (A92). $^1$H NMR (400 MHz, d$_6$-DMSO) δ 9.87 (s, 1H), 8.81 (s, 1H), 7.94 (s, 1H), 7.43 (s, 1H), 7.39 (dd, J=8, 2 Hz, 1H), 7.30 (d, J=2 Hz, 1H), 7.21 (d, J=8 Hz, 1H), 6.02 (d, J=6 Hz, 1H), 4.48 (bt, J=6 Hz, 1H), 3.67 (s, 3H), 2.61 (s, 3H), 2.07 (s, 3H) 0.94 (d, J=6 Hz, 3H), 0.87 (d, J=6 Hz, 3H). MS m/z 420.4 (M+1).

Example A104

Synthesis of 7-ethyl-3-(5-(5-isopropyl-1,2,4-oxadiazol-3-ylamino)-2-methylphenyl)-1-methyl-1,6-naphthyridin-2(1H)-one

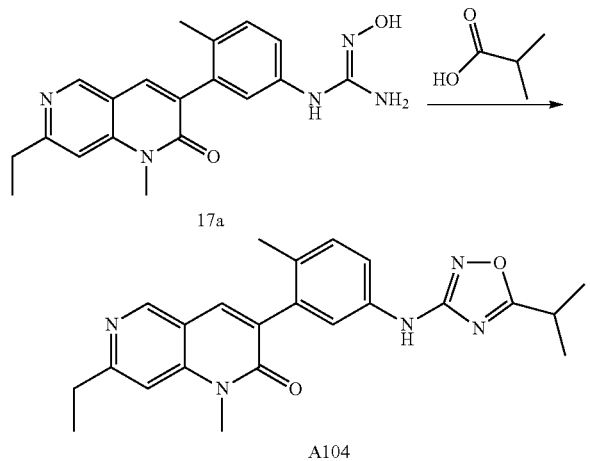

A104

To a solution of isobutyric acid (8 µL, 0.09 mmol) in DMF (1 mL) were added DIPEA (16 µL, 0.09 mmol) and HATU (33 mg, 0.09 mmol). After stirring at rt for 15 min 17a (30 mg, 0.09 mmol) was added as a solution in DMF (0.5 mL). The reaction was stirred at rt until complete consumption of 17a was determined by LC/MS and then heated at 100° C. for 1 h. Subsequently the reaction was cooled to rt, filtered and purified by preparative LC/MS to give 7-ethyl-3-(5-(5-isopropyl-1,2,4-oxadiazol-3-ylamino)-2-methylphenyl)-1-methyl-1,6-naphthyridin-2(1H)-one (A104). $^1$H NMR (400 MHz, d$_6$-DMSO) δ 9.91 (s, 1H), 9.10 (s, 1H), 8.05 (s, 1H), 7.78 (s, 1H), 7.41 (dd, J=8, 2 Hz, 1H), 7.33 (d, J=2 Hz, 1H), 7.23 (d, J=8 Hz, 1H), 3.72 (s, 3H), 3.19 (m, 1H), 3.01 (q, J=7.6 Hz, 2H), 2.08 (s, 3H), 1.36 (t, J=7.6 Hz, 3H), 1.31, (d, J=6.8 Hz, 6H). MS m/z 404.1 (M+1).

Example A105

Synthesis of 7-ethyl-1-methyl-3-(2-methyl-5-(5-(pyridin-2-yl)-1,2,4-oxadiazol-3-ylamino)phenyl)-1,6-naphthyridin-2(1H)-one

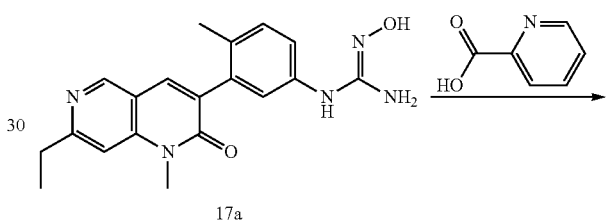

17a

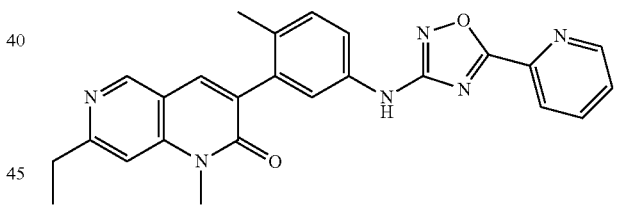

A105

To a solution of picolinic acid (10 mg, 0.09 mmol) in DMF (1 mL) were added DIPEA (16 µL, 0.09 mmol) and HATU (33 mg, 0.09 mmol). After stirring at rt for 15 min, 17a (30 mg, 0.09 mmol) was added as a solution in DMF (0.5 mL). The reaction was stirred at rt until complete consumption of 17a was determined by LC/MS and then heated at 100° C. for 1 h. Subsequently the reaction was cooled to rt, filtered and purified by preparative LC/MS to give 7-ethyl-1-methyl-3-(2-methyl-5-(5-(pyridin-2-yl)-1,2,4-oxadiazol-3-ylamino)phenyl)-1,6-naphthyridin-2(1H)-one (A105). $^1$H NMR (400 MHz, d$_6$-DMSO) δ 10.13 (s, 1H), 9.09 (s, 1H), 8.81 (s, 1H), 8.18 (d. J=8 Hz, 1H), 8.10 (m, 2H), 7.75 (s, 1H), 7.71 (m, 1H), 7.47 (d, J=8 Hz, 1H), 7.41 (s, 1H), 7.28 (d, J=8 Hz, 1H), 3.72 (s, 3H), 3.01 (q, J=7.6 Hz, 2H), 2.10 (s, 3H), 1.36 (t, J=7.6 Hz, 3H). MS m/z 439.3 (M+1).

Method 4

Example A9

Synthesis of 1,7-dimethyl-3-(2-methyl-5-(5-(thiazol-2-yl)-1,2,4-oxadiazol-3-ylamino)phenyl)-1,6-naphthyridin-2(1H)-one

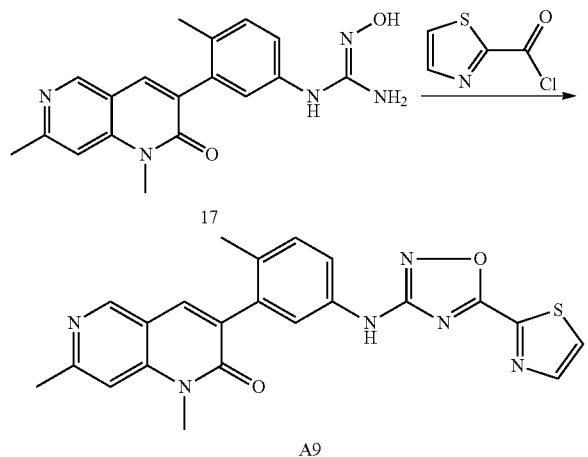

To a solution of 17 (0.1 mmol) in THF (1 mL) was added thiazole-2-carbonyl chloride (0.1 mmol). The reaction mixture was stirred at rt for 30 min. Then ethanol (1 mL) was added and heated at reflux for 3 h. After filtration, the mixture was purified by preparative LC/MS to give 3-(5-(5-(thiazol-2-yl)-1,2,4-oxadiazol-3-ylamino)-2-methylphenyl)-1,7-dimethyl-1,6-naphthyridin-2(1H)-one (A9) MS m/z 431.1 (M+1).

Method 5

Example A3

Synthesis of 3-(5-(5-cyclopropyl-1,2,4-oxadiazol-3-ylamino)-2-methylphenyl)-1,7-dimethyl-1,6-naphthyridin-2(1H)-one

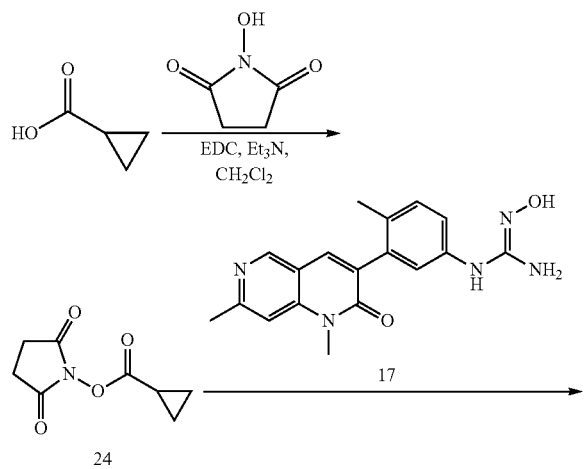

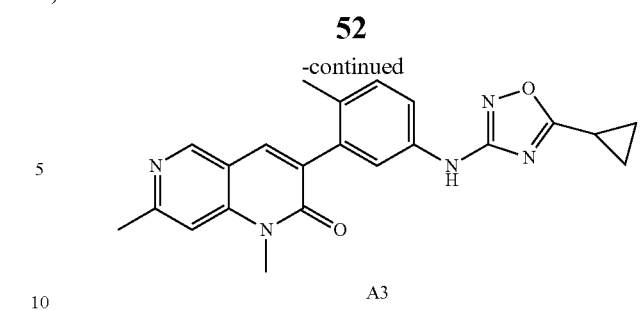

1-Hydroxypyrrolidine-2,5-dione (1.18 g, 10.3 mmol), cyclopropanecarboxylic acid (1.01 ml, 10 mmol), EDC (2.01 g, 10.5 mmol) and Et$_3$N (2.8 mmol, 20 mmol) in DCM were stirred at rt for 5 h before it was partitioned with saturated NH$_4$Cl solution. The organic layer was washed with brine and dried over Na$_2$SO$_4$. After filtration and concentration, 2,5-dioxopyrrolidin-1-yl cyclopropanecarboxylate 24 was isolated and used without further purification.

2,5-Dioxopyrrolidin-1-yl cyclopropanecarboxylate 24 (0.62 g, 3.38 mmol) and hydroxyguanidine 17 (1.0 g, 2.96 mmol) in dry dioxane (10 mL) were stirred at 100° C. for 4 h. After cooling and filtration, the mixture was purified by preparative LC/MS to give A3 as a solid. MS m/z 388.4 (M+1).

Method 6

Example B4

Synthesis of 1,7-dimethyl-3-(2-methyl-5-(5-phenyl-1,3,4-oxadiazol-2-ylamino)phenyl)-1,6-naphthyridin-2(1H)-one

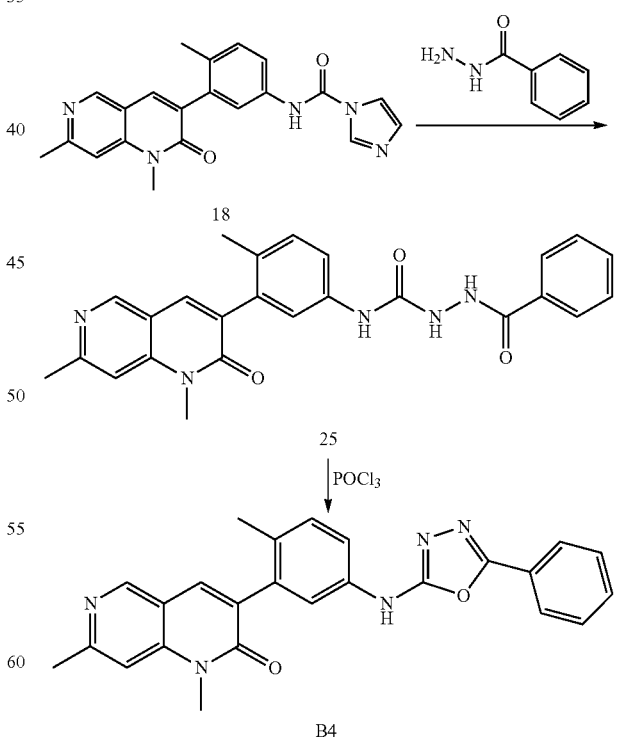

The crude 18 (0.08 mmol) was dissolved in THF (0.5 mL) and benzoylhydrazide (14 mg, 0.1 mmol) was added at rt. The reaction mixture was stirred at rt for 1 h to yield the crude 2-benzoyl-N-(3-(1,7-dimethyl-2-oxo-1,2-dihydro-1,6-naphthyridin-3-yl)-4-methylphenyl)hydrazinecarboxamide 25, which was used without purification after removal of THF. MS m/z 442.2 (M+1).

The crude 25 (0.08 mmol) was heated in POCl₃ (0.1 mL) at reflux for 2 h. After evaporation, the residue was purified by preparative LCMS to afford the title compound B4 as a TFA salt. ¹H NMR (400 MHz, d₄-MeOH) δ 9.07 (s, 1H), 8.09 (s, 1H), 7.96 (m, 2H), 7.89 (s, 1H), 7.64 (d, J=2.4 Hz, 1H), 7.55 (m, 3H), 7.43 (dd, J=8.3, 2.4 Hz, 1H), 7.32 (d, J=8.3 Hz, 1H), 3.84 (s, 3H), 2.85 (s, 3H), 2.2 (s, 3H). MS m/z 424.3 (M+1).

Example B5

Synthesis of 3-(5-(5-isobutyl-1,3,4-oxadiazol-2-ylamino)-2-methylphenyl)-1,7-dimethyl-1,6-naphthyridin-2(1H)-one

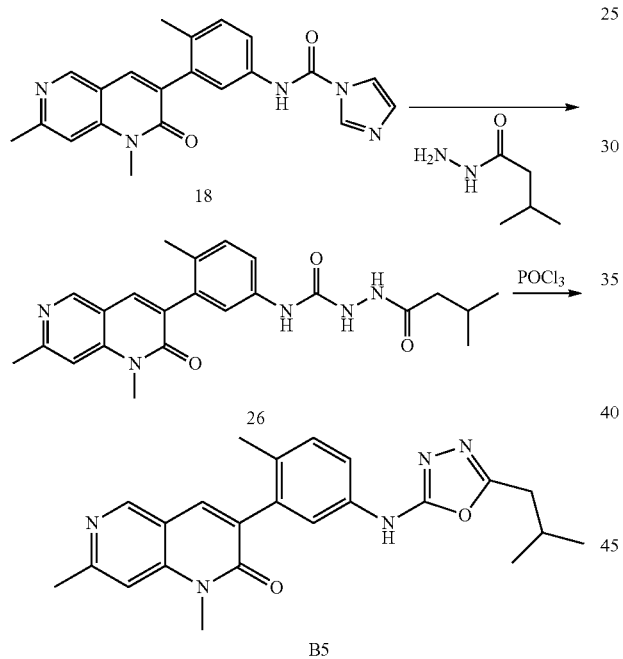

The crude 18 (0.08 mmol) was dissolved in THF (0.5 mL) and 3-methylbutanehydrazide (12 mg, 0.1 mmol) was added at rt. The reaction mixture was stirred at rt for 1 h to yield the crude N-(3-(1,7-dimethyl-2-oxo-1,2-dihydro-1,6-naphthyridin-3-yl)-4-methylphenyl)-2-(3-methylbutanoyl)hydrazinecarboxamide 26, which was used without purification after removal of THF. MS m/z 422.2 (M+1).

The above crude N-(3-(1,7-dimethyl-2-oxo-1,2-dihydro-1,6-naphthyridin-3-yl)-4-methylphenyl)-2-(3-methylbutanoyl)hydrazinecarboxamide 26 (0.08 mmol) was heated in POCl₃ (0.1 mL) at reflux for 2 h. After evaporation, the residue was purified by preparative LCMS to afford the title compound B5 as a TFA salt. MS m/z 404.2 (M+1).

Method 7

Example C1

Synthesis of 3-(5-(5-cyclopentyl-4H-1,2,4-triazol-3-ylamino)-2-methylphenyl)-1,7-dimethyl-1,6-naphthyridin-2(1H)-one

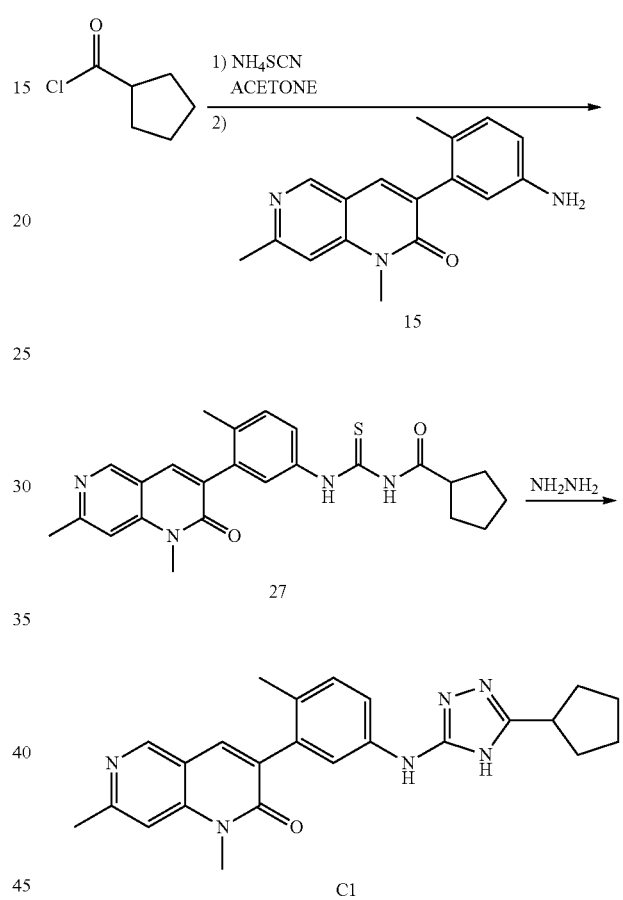

The mixture of cyclopentanecarbonyl chloride (13 mg, 0.1 mmol) and ammonium isothiocyanate (7.6 mg, 0.1 mmol) in acetone (1.0 mL) was heated at 40° C. for 3 h. To the above reaction mixture, 3-(5-amino-2-methylphenyl)-1,7-dimethyl-1,6-naphthyridin-2(1H)-one (15) (27.5 mg, 0.1 mmol) was added at rt and stirred for 30 min. The solvent was removed under vacuum to yield N-(3-(1,7-dimethyl-2-oxo-1,2-dihydro-1,6-naphthyridin-3-yl)-4-methylphenylcarbamothioyl)cyclopentanecarboxamide 27, which was used without purification. MS m/z 435.2 (M+1).

To the crude N-(3-(1,7-dimethyl-2-oxo-1,2-dihydro-1,6-naphthyridin-3-yl)-4-methylphenylcarbamothioyl)cyclopentanecarboxamide 27 obtained above in EtOH (1.0 mL), hydrazine (4 mg, 0.12 mmol) was added and the resulting mixture was heated at 80° C. for 2 h. The residue was purified by preparative LC/MS to give C1. MS m/z 415.2 (M+1).

Example C6

Synthesis of 1,7-dimethyl-3-(2-methyl-5-(5-phenyl-4H-1,2,4-triazol-3-ylamino)phenyl)-1,6-naphthyridin-2(1H)-one

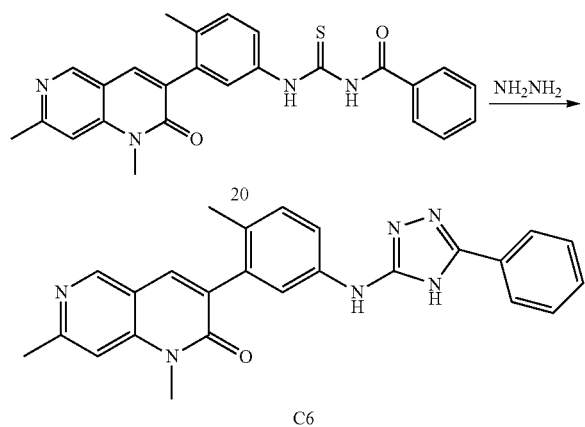

To a solution of 20 (44 mg, 0.1 mmol) in EtOH (1 mL) was added hydrazine (16 μL, 0.5 mmol). The mixture was heated at reflux for 2 h. Solvent was removed in vacuo and the crude product was purified by preparative LC/MS to give C6. $^1$H NMR (400 MHz, d$_4$-MeOH) δ 9.04 (s, 1H), 8.05 (s, 1H), 7.95 (m, 1H), 7.93 (d, J=2 Hz, 1H), 7.86 (s, 1H), 7.47 (m, 5H), 7.25 (d, J=7.9 Hz, 1H), 7.29 (d, J=8.4 Hz, 1H), 3.83 (s, 3H), 2.84 (s, 3H), 2.17 (s, 3H). MS m/z 423.2 (M+1).

Method 8

Example D1

Synthesis of 1,7-dimethyl-3-(2-methyl-5-(5-phenyl-isoxazol-3-ylamino)phenyl)-1,6-naphthyridin-2(1H)-one To a solution of acetophenone (24.0 mg, 0.2 mmol) and NaH (16.0 mg, 0.4 mmol, 60% in mineral oil) in DMF (1 mL) was added 3-(5-isothiocyanato-2-methylphenyl)-1,7-dimethyl-1,6-naphthyridin-2(1H)-one 19 (64.5 mg, 0.2 mmol) at rt. The reaction was quenched with water after 1 h. The reaction mixture was extracted with EtOAc. The organic layer was washed with brine, dried over Na$_2$SO$_4$, filtered and concentrated to yield crude 3-(5-isothiocyanato-2-methylphenyl)-1,7-dimethyl-1,6-naphthyridin-2(1H)-one 28, which was used without purification. MS m/z 442.2 (M+1).

To a solution of 3-(5-isothiocyanato-2-methylphenyl)-1,7-dimethyl-1,6-naphthyridin-2(1H)-one 28 (22 mg, 0.05 mmol) in EtOH (0.5 mL) was added solid NaOH (20 mg, 0.5 mmol) and MeI (7 mg, 0.05 mmol). The mixture was stirred at rt for 1 h to yield 3-(5-((Z)-1-(methylthio)-3-oxo-3-phenylprop-1-enylamino)-2-methylphenyl)-1,7-dimethyl-1,6-naphthyridin-2(1H)-one 29. Hydroxylamine hydrochloride (35 mg, 0.5 mmol) was added to the above reaction mixture and the reaction was heated at 80° C. for 1 h. After filtration, the mixture was purified by preparative LC/MS to give 3-(5-(5-phenylisoxazol-3-ylamino)-2-methylphenyl)-1,7-dimethyl-1,6-naphthyridin-2(1H)-one D1. MS m/z 423.1 (M+1).

Method 9

Example D9

Synthesis of 1,7-dimethyl-3-(2-methyl-5-(5-(thiazol-2-yl)isoxazol-3-ylamino)phenyl)-1,6-naphthyridin-2(1H)-one

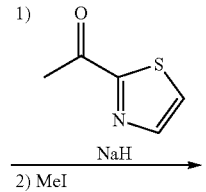

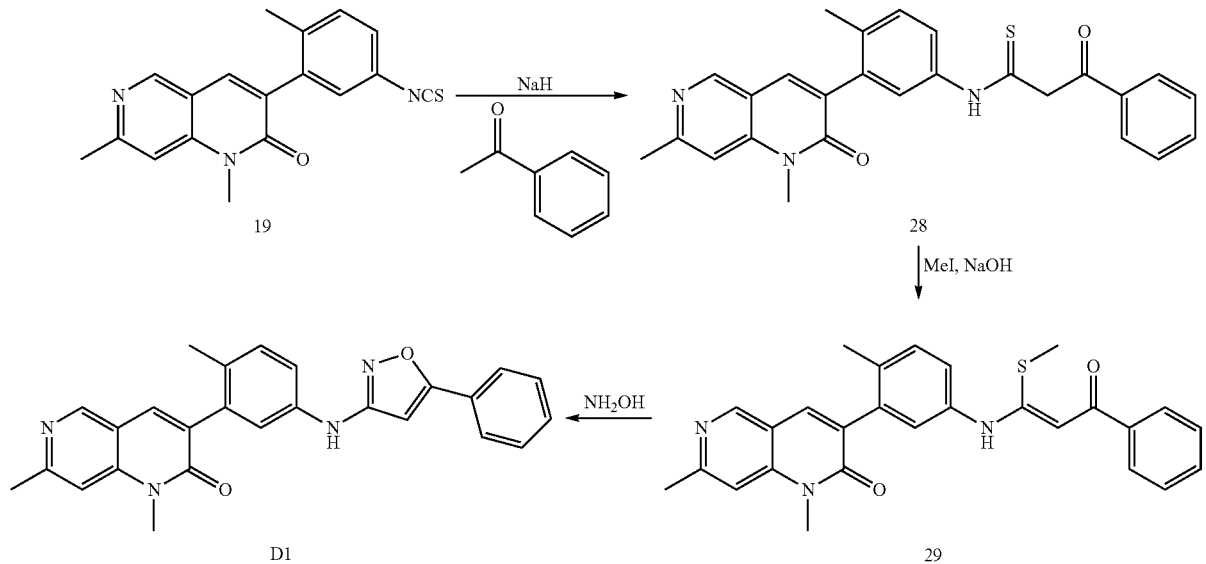

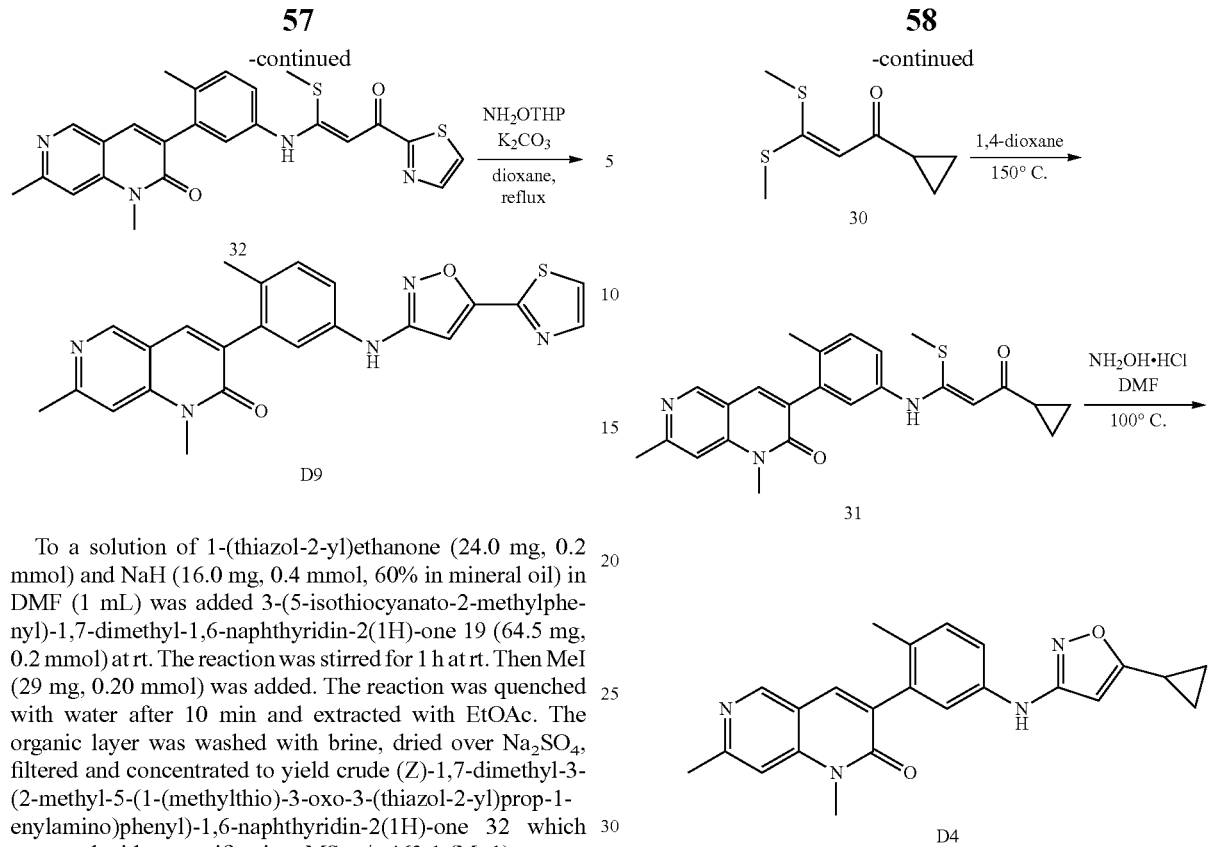

To a solution of 1-(thiazol-2-yl)ethanone (24.0 mg, 0.2 mmol) and NaH (16.0 mg, 0.4 mmol, 60% in mineral oil) in DMF (1 mL) was added 3-(5-isothiocyanato-2-methylphenyl)-1,7-dimethyl-1,6-naphthyridin-2(1H)-one 19 (64.5 mg, 0.2 mmol) at rt. The reaction was stirred for 1 h at rt. Then MeI (29 mg, 0.20 mmol) was added. The reaction was quenched with water after 10 min and extracted with EtOAc. The organic layer was washed with brine, dried over $Na_2SO_4$, filtered and concentrated to yield crude (Z)-1,7-dimethyl-3-(2-methyl-5-(1-(methylthio)-3-oxo-3-(thiazol-2-yl)prop-1-enylamino)phenyl)-1,6-naphthyridin-2(1H)-one 32 which was used without purification. MS m/z 463.1 (M+1).

The mixture of (Z)-1,7-dimethyl-3-(2-methyl-5-(1-(methylthio)-3-oxo-3-(thiazol-2-yl)prop-1-enylamino)phenyl)-1,6-naphthyridin-2(1H)-one 32 (462 mg, 1.0 mmol), O-(tetrahydro-2H-pyran-2-yl)hydroxylamine (293 mg, 2.5 mmol) and $K_2CO_3$ (415 mg, 3.0 mmol) in 1,4-dioxane (5 mL) in a sealed vial was heated at 150° C. for 30 h. The mixture was purified by preparative LC/MS to give 1,7-dimethyl-3-(2-methyl-5-(5-(thiazol-2-yl)isoxazol-3-ylamino)phenyl)-1,6-naphthyridin-2(1H)-one (D9). $^1$H NMR (400 MHz, d6-DMSO) δ 10.73 (s, 1H), 9.19 (s, 1H), 8.11 (s, 1H), 7.93 (s, 1H), 7.87 (d, J=3.2 Hz, 1H), 7.74 (d, J=3.2 Hz, 1H), 7.65 (d, J=2.4 Hz, 1H), 7.61 (s, 1H), 7.53 (dd, J=2.4, 8.0 Hz, 1H), 7.27 (d, J=8.0 Hz, 1H), 3.72 (s, 3H), 2.78 (s, 3H), 2.10 (s, 3H). MS m/z 430.2 (M+1).

Method 10

Example D4

Synthesis of 3-(5-(5-cyclopropylisoxazol-3-ylamino)-2-methylphenyl)-1,7-dimethyl-1,6-naphthyridin-2(1H)-one

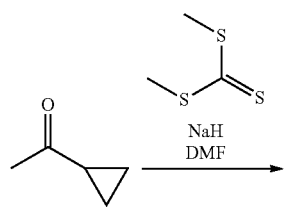

To a mixture of NaH (240 mg, 6.0 mmol, 60% in mineral oil) and 1-cyclopropylethanone (168.2 mg, 2.0 mmol) in DMF (1 mL) was added dimethyl carbonotrithioate (304.3 mg, 2.2 mmol) at rt. The reaction was quenched with water after 3 h and extracted with EtOAc. The organic layer was washed with brine, dried over $Na_2SO_4$, filtered and concentrated to yield crude 1-cyclopropyl-3,3-bis(methylthio)prop-2-en-1-one 30 which was purified by flash chromatography on silica with 15% EtOAc in hexanes as eluant. $^1$H NMR (400 MHz, $CDCl_3$) δ 6.14 (s, 1H), 2.41 (s, 3H), 2.40 (s, 3H), 1.81 (m, 1H), 1.00 (m, 2H), 0.77 (m, 2H). MS m/z 189.0 (M+1).

The mixture of 3-(5-amino-2-methylphenyl)-1,7-dimethyl-1,6-naphthyridin-2(1H)-one 15 (165 mg, 0.589 mmol) and 1-cyclopropyl-3,3-bis(methylthio)prop-2-en-1-one 30 (111 mg, 0.589 mmol) in 1,4-dioxane (2 mL) was heated in a sealed vial at 150° C. overnight. The solvent was removed to yield crude (Z)-3-(5-(3-cyclopropyl-1-(methylthio)-3-oxoprop-1-enylamino)-2-methylphenyl)-1,7-dimethyl-1,6-naphthyridin-2(1H)-one 31 which was used without further purification. MS m/z 420.1 (M+1).

To the above crude mixture of (Z)-3-(5-(3-cyclopropyl-1-(methylthio)-3-oxoprop-1-enylamino)-2-methylphenyl)-1,7-dimethyl-1,6-naphthyridin-2(1H)-one 31 were added hydroxylamine hydrochloride (174 mg, 2.4 mmol) and DMF (2 mL). The resulting mixture was heated at 100° C. for 30 min. The mixture was purified by preparative LC/MS to give 3-(5-(5-cyclopropylisoxazol-3-ylamino)-2-methylphenyl)-1,7-dimethyl-1,6-naphthyridin-2(1H)-one (D4). $^1$H NMR (400 MHz, d6-DMSO) δ 9.21 (s, 1H), 9.13 (s, 1H), 8.10 (s, 1H), 7.96 (s, 1H), 7.39 (d, J=2.4 Hz, 1H), 7.29 (dd, J=2.4, 8.4 Hz, 1H), 7.19 (d, J=8.4 Hz, 1H), 5.83 (s, 1H), 3.72 (s, 3H), 2.79 (s, 3H), 2.07 (s, 3H), 2.05 (m, 1H), 1.01 (m, 2H), 0.84 (m, 2H). MS m/z 387.2 (M+1).

Method 11

Example E2

Synthesis of 1,7-dimethyl-3-(2-methyl-5-(3-(pyridin-2-yl)-1,2,4-oxadiazol-5-ylamino)phenyl)-1,6-naphthyridin-2(1H)-one

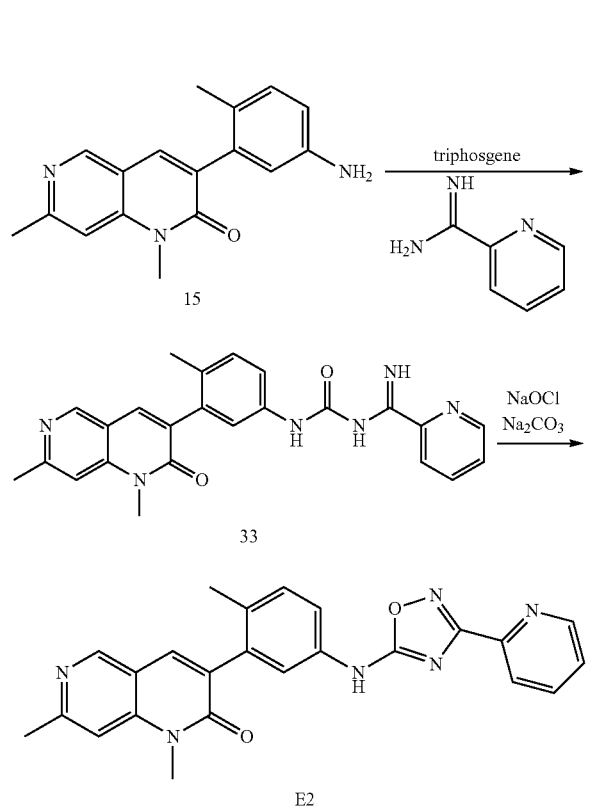

Example E3

Synthesis of 3-(5-(3-isopropyl-1,2,4-oxadiazol-5-ylamino)-2-methylphenyl)-1,7-dimethyl-1,6-naphthyridin-2(1H)-one

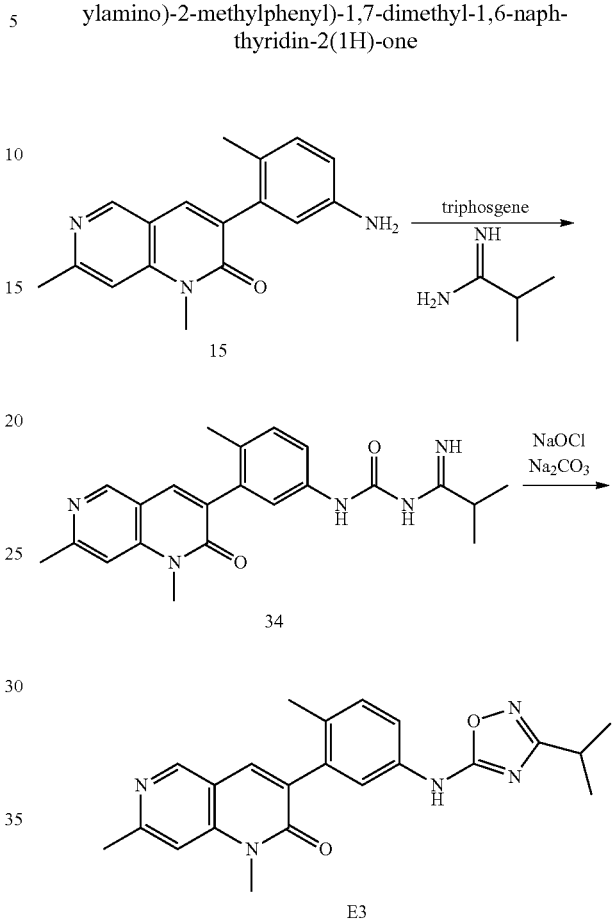

To a solution of 15 (40 mg, 0.14 mmol) in DCM (2 mL) was added DIPEA (75 μL) and triphosgene (14 mg, 0.05 mmol) and stirred at rt for 30 min. Then picolinimidamide (23 mg, 014 mmol) was added and stirred at rt for 4 h. The reaction was subsequently partitioned with water, washed with brine, dried over magnesium sulfate, filtered and reduced to dryness. The crude intermediate 33 was used in the next reaction without purification.

To a solution of 33 (60 mg, 0.14 mmol) in MeOH/Water (1:1, 2 mL) was added HCl (0.14 mL, 1M solution) and NaOCl (95 μL, 10-13% aq solution). The reaction was stirred at rt until homogenous and then Na$_2$CO$_3$ (15 mg, 0.14 mmol) was added and the reaction was heated to 65° C. for 12 h. Subsequently the reaction was diluted with DMF (~1 mL) and purified by preparative LC/MS to give 1,7-dimethyl-3-(2-methyl-5-(3-(pyridin-2-yl)-1,2,4-oxadiazol-5-ylamino)phenyl)-1,6-naphthyridin-2(1H)-one E2. $^1$H NMR (400 MHz, d$_6$-DMSO) δ 11.17 (s, 1H), 9.05 (s, 1H), 8.72 (s, 1H), 8.08 (s, 1H), 8.01 (m, 2H), 7.75 (s, 1H), 7.66 (dd, J=8, 2 Hz, 1H), 7.57 (s, 1H), 7.44 (d, J=2 Hz, 1H), 7.35 (d, J=8 Hz, 1H), 3.70 (s, 3H), 2.72 (s, 3H), 2.13 (s, 1H). MS m/z 425.3 (M+1).

To a solution of 15 (40 mg, 0.14 mmol) in DCM (2 mL) were added DIPEA (75 μL) and triphosgene (14 mg, 0.05 mmol) and stirred at rt for 30 min. Then isobutyrimidamide (18 mg, 014 mmol) was added and stirred at rt for 4 h. The reaction was subsequently partitioned with water, washed with brine, dried over magnesium sulfate, filtered and reduced to dryness. The crude intermediate 34 is used in the next reaction without purification.

To a solution of intermediate 34 (55 mg, 0.14 mmol) in MeOH:Water=1:1 (2 mL) were added HCl (0.14 mL, 1M solution) and NaOCl (95 μL, 10-13% aq solution). The reaction was stirred at rt until homogenous and then Na$_2$CO$_3$ (15 mg, 0.14 mmol) was added and the reaction was heated to 65° C. for 12 h. Subsequently the reaction was diluted with DMF (~1 mL), filtered and purified by preparative LC/MS to give 3-(5-(3-isopropyl-1,2,4-oxadiazol-5-ylamino)-2-methylphenyl)-1,7-dimethyl-1,6-naphthyridin-2(1H)-one (E3). $^1$H NMR (400 MHz, d$_6$-DMSO) δ 10.84 (s, 1H), 9.05 (s, 1H), 8.05 (s, 1H), 7.77 (s, 1H), 7.55 (dd, J=8, 2 Hz, 1H), 7.33 (d, J=2 Hz, 1H), 7.30 (d, J=8 Hz, 1H), 3.69 (s, 3H), 2.91 (m, 1H), 2.72 (s, 3H), 2.11 (s, 1H), 1.23, (d, J=6.8 Hz, 6H). MS m/z 390.4 (M+1).

Method 12

Example F1

Synthesis of 1,7-dimethyl-3-(2-methyl-5-(3-(thiazol-2-yl)isoxazol-5-ylamino)phenyl)-1,6-naphthyridin-2(1H)-one

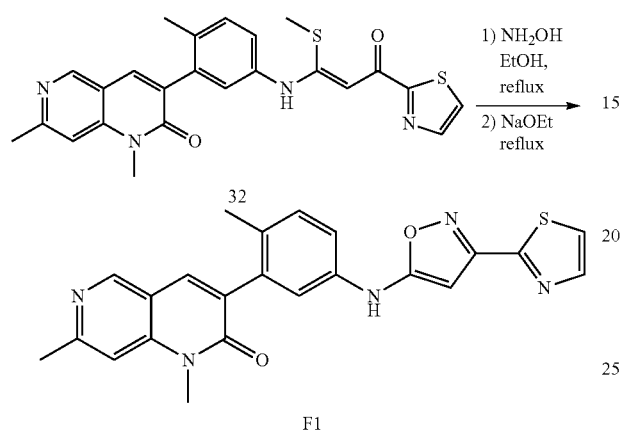

F1

To the mixture of hydroxylamine hydrochloride (42 mg, 0.6 mmol) and KOH (34 mg, 0.6 mmol) in EtOH (2 mL) was added the crude (Z)-1,7-dimethyl-3-(2-methyl-5-(1-(methylthio)-3-oxo-3-(thiazol-2-yl)prop-1-enyl amino)phenyl)-1,6-naphthyridin-2(1H)-one 32. The resulting mixture was heated at 80° C. for 30 min. Then NaOEt (40.8 mg, 0.6 mmol) was added and the reaction mixture was refluxed for 1 h. The mixture was purified by preparative LC/MS to give 1,7-dimethyl-3-(2-methyl-5-(3-(thiazol-2-yl)isoxazol-5-ylamino) phenyl)-1,6-naphthyridin-2(1H)-one (F1). $^1$H NMR (400 MHz, d6-DMSO) δ 9.50 (s, 1H), 9.13 (s, 1H), 7.95-8.10 (m, 3H), 7.88 (s, 1H), 7.38 (s, 1H), 7.30 (d, J=8.0 Hz, 1H), 7.18 (d, J=8.0 Hz, 1H), 6.94 (s, 1H), 3.65 (s, 1H), 2.72 (s, 3H), 2.03 (s, 3H). MS m/z 430.1 (M+1).

Method 13

Example G1

Synthesis of 1,7-dimethyl-3-(2-methyl-5-(3-(thiazol-2-yl)isoxazol-5-ylamino)phenyl)-1,6-naphthyridin-2(1H)-one (G1)

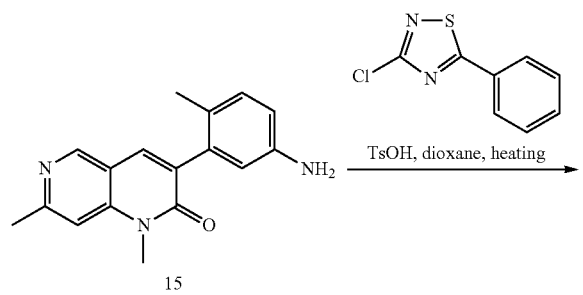

G1

3-(5-Amino-2-methylphenyl)-1,7-dimethyl-1,6-naphthyridin-2(1H)-one 15 (30 mg, 0.107 mmol), 3-chloro-5-phenyl-1,2,4-thiadiazole (41 mg, 0.21 mmol) and TsOH (10 mg) were heated at 100° C. in dioxane (2 ml). After 10 h, the solution was cooled and filtered. The mixture was purified by preparative LC/MS to give 1,7-dimethyl-3-(2-methyl-5-(5-phenyl-1,2,4-thiadiazol-3-ylamino)phenyl)-1,6-naphthyridin-2(1H)-one (G1). MS m/z 440.5 (M+1).

Method 14

Example H1

Synthesis of 1,7-dimethyl-3-(2-methyl-5-(5-phenyl-1,3,4-thiadiazol-2-ylamino)phenyl)-1,6-naphthyridin-2(1H)-one (H1)

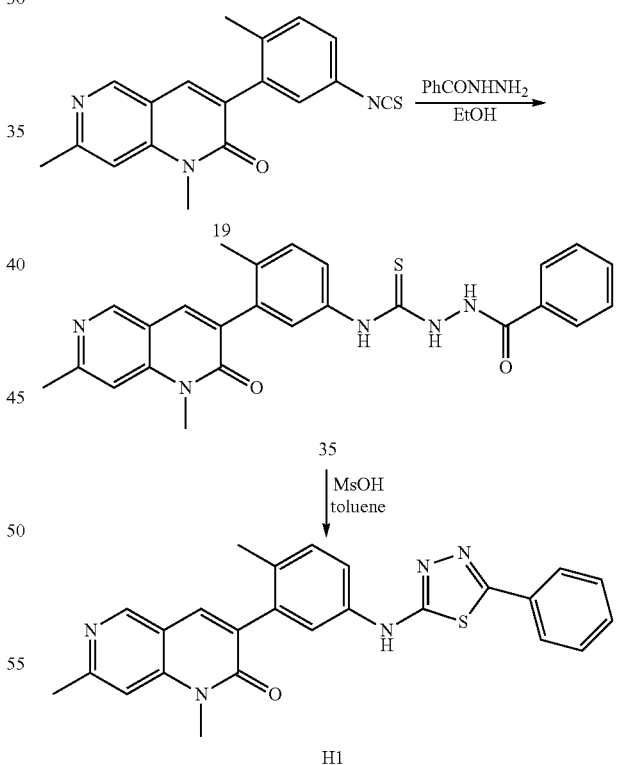

H1

To a solution of 19 (50 mg, 0.16 mmol) in EtOH (1.0 mL), benzohydrazide (26 mg, 0.19 mmol) was added and stirred at rt for 2 h. The solvent was removed under vacuum to yield crude 2-benzoyl-N-(3-(1,7-dimethyl-2-oxo-1,2-dihydro-1,6-naphthyridin-3-yl)-4-methylphenyl)hydrazinecarbothioamide, which was used without purification. MS m/z 458.2 (M+1).

The mixture of crude 2-benzoyl-N-(3-(1,7-dimethyl-2-oxo-1,2-dihydro-1,6-naphthyridin-3-yl)-4-methylphenyl) hydrazinecarbothioamide 35 and methanesulfonic acid (2 drops) in toluene (1 mL) was heated at 130° C. overnight in a sealed vial. The reaction was evaporated to dryness and the crude residue was purified by preparative LC/MS to give 1,7-dimethyl-3-(2-methyl-5-(5-phenyl-1,3,4-thiadiazol-2-ylamino)phenyl)-1,6-naphthyridin-2(1H)-one (H1). MS m/z 440.1 (M+1).

By repeating the procedures described in the above examples (intermediates and final compounds), using appropriate starting materials, the following compounds of Formula I, as identified in Table 1, are obtained.

TABLE 1

| Compound Number | Structure | $^1$H NMR 400 MHz and/or MS m/z | IC$_{50}$ Mo7e (μM) | Synthesis Method |
|---|---|---|---|---|
| A1 | 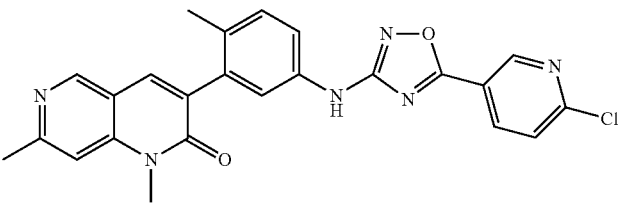 | MS m/z 459.1, 461.1 (M + 1) | 0.1 | 2 |
| A2 | 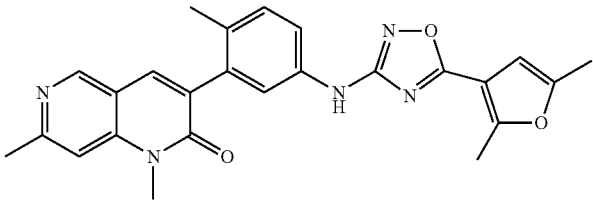 | MS m/z 442.2 (M + 1) | 0.126 | 2 |
| A3 | 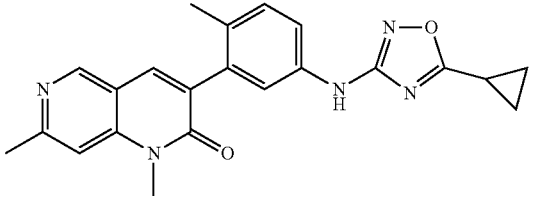 | MS m/z 388.2 (M + 1) | 0.016 | 2, 5 |
| A4 | 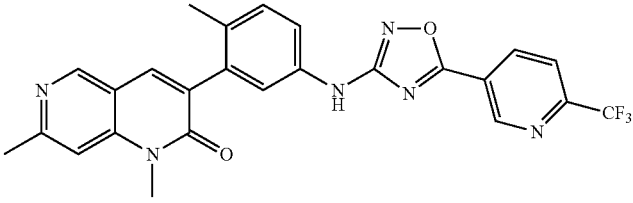 | MS m/z 493.1 (M + 1) | 0.472 | 2 |
| A5 | 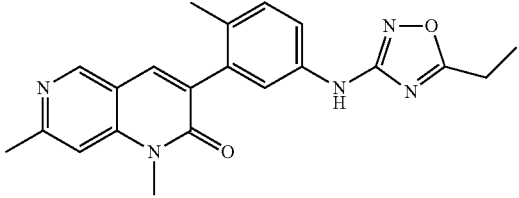 | $^1$HNMR (400 MHz, d$_4$-CH$_3$OH) δ 9.08 (s, 1H), 8.04 (s, 1H), 7.45 (s, 1H), 7.34 (dd, J = 8.0 and 4.0 Hz, 1H), 7.25 (d, J = 8.0 Hz, 1H), 3.82 (s, 3H), 2.85 (s, 3H), 2.85 (q, J = 8.0 Hz, 2H), 2.16 (s, 3H). 1.35 (t, J = 8.0 Hz, 3H) MS m/z 376.1 (M + 1) | 0.049 | 1 |
| A6 | 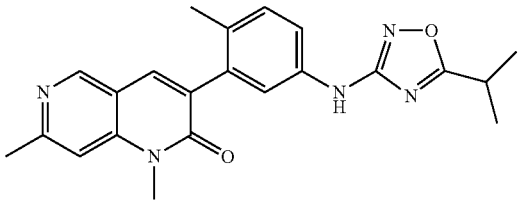 | MS m/z 390.1 (M + 1) | 0.034 | 2 |

TABLE 1-continued

| Compound Number | Structure | $^1$H NMR 400 MHz and/or MS m/z | IC$_{50}$ Mo7e (μM) | Synthesis Method |
|---|---|---|---|---|
| A7 | 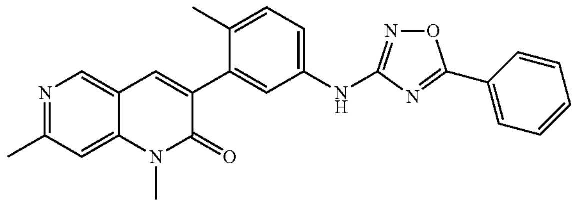 | $^1$H NMR (400 MHz, d$_4$-MeOH) δ 9.03 (s, 1H), 8.12 (s, 1H), 8.1 (d, J = 1.5 Hz, 1H), 8.05 (s, 1H), 7.83 (s, 1H), 7.65 (d, J = 6.2 Hz, 1H), 7.59 (d, J = 6.3 Hz, 1H), 7.57 (d, J = 7.2 Hz, 1H), 7.5 (d, J = 2.4 Hz, 1H), 7.43 (dd, J = 8.3, 2.5 Hz, 1H), 7.27 (d, J = 8.4 Hz, 1H), 3.84 (s, 3H), 2.83 (s, 3H), 2.18 (s, 3H) MS m/z 424.1 (M + 1) | 0.076 | 2, 3 |
| A8 | 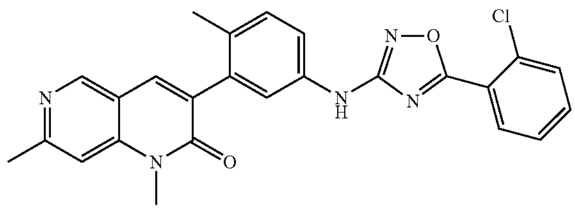 | $^1$H NMR (400 MHz, CDCl$_3$) δ 8.65 (s, 1H), 7.97 (dd, J = 7.8, 1.7 Hz, 1H), 7.65 (s, 1H), 7.5 (dd, J = 8.1, 1.3 Hz, 1H), 7.44 (dt, J = 7.3, 1.8 Hz, 1H), 7.35 (dt, J = 7.8, 1.4 Hz, 1H), 7.33 (d, J = 2.5 Hz, 1H), 7.3 (dd, J = 8.2, 2.4 Hz, 1H), 7..04 (s, 1H), 6.78 (s, 1H), 3.67 (s, 3H), 2.65 (s, 3H), 2.14 (s, 3H) MS m/z 458.1, 460.1 (M + 1) | 0.158 | 2 |
| A9 | 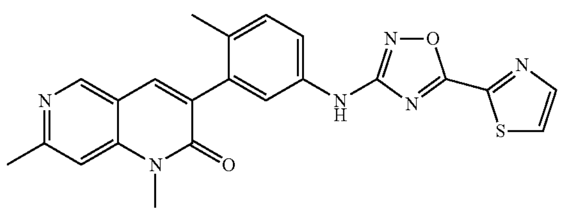 | MS m/z 431.1 (M + 1) | 0.204 | 4 |
| A10 | 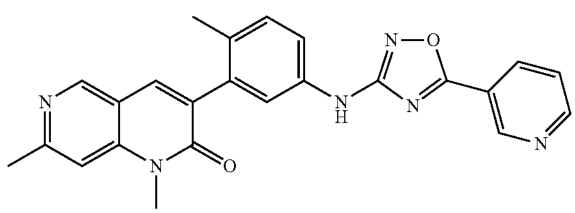 | MS m/z 425.1 (M + 1) | 0.145 | 4 |
| A11 | 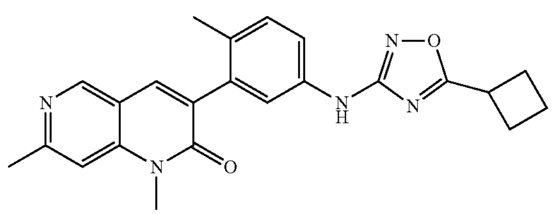 | MS m/z 402.2 (M + 1) | 0.012 | 2 |
| A12 | 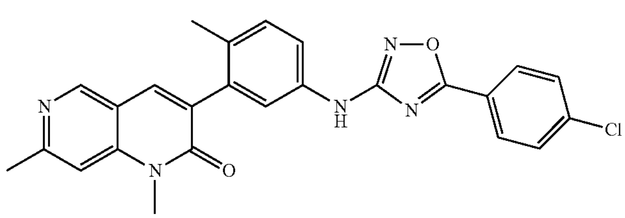 | $^1$H NMR (400 MHz, d$_4$-MeOH) δ 9.06 (s, 1H), 8.09 (dt, J = 8.7, 2.0 Hz, 2H), 8.05 (s, 1H), 7.89 (s, 1H), 7.62 (t, J = 2 Hz, 1H), 7.6 (t, J = 2 Hz, 1H), 7.5 (d, J = 2.5 Hz, 1H), 7.4 (dd, J = 8.3, 2.5 Hz, 1H), 7.27 (d, J = 8.4 Hz, 1H), 3.83 (s, 3H), 2.85 (s, 3H), 2.18 (s, 3H) MS m/z 458.1, 460.1 (M + 1) | 0.013 | 2 |

TABLE 1-continued

| Compound Number | Structure | ¹H NMR 400 MHz and/or MS m/z | IC$_{50}$ Mo7e (μM) | Synthesis Method |
| --- | --- | --- | --- | --- |
| A13 | 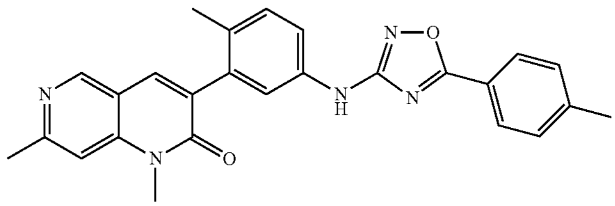 | ¹H NMR (400 MHz, CDCl$_3$) δ 8.64 (s, 1H), 7.9 (d, J = 8.2 Hz, 2H), 7.65 (s, 1H), 7.29 (m, 2H), 7.25 (d, J = 8 Hz, 2H), 7.2 (m, 1H), 7.04 (s, 1H), 6.68 (s, 1H), 3.67 (s, 3H), 2.65 (s, 3H), 2.37 (s, 3H), 2.13 (s, 3H) MS m/z 438.3 (M + 1) | 0.013 | 2 |
| A14 | 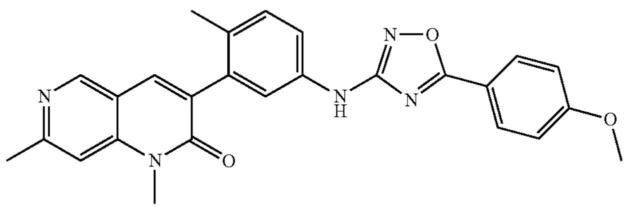 | ¹H NMR (400 MHz, CDCl$_3$) δ 8.64 (s, 1H), 7.95 (d, J = 9 Hz, 2H), 7.65 (s, 1H), 7.3 (m, 2H), 7.18 (m, 1H), 7.05 (s, 1H), 6.94 (d, J = 9 Hz, 2H), 6.75 (s, 1H), 3.82 (s, 3H), 3.68 (s, 3H), 2.65 (s, 3H), 2.13 (s, 3H) MS m/z 454.2 (M + 1) | 0.014 | 2 |
| A15 | 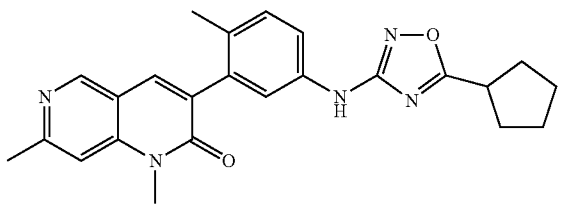 | MS m/z 416.2 (M + 1) | 0.028 | 2 |
| A16 | 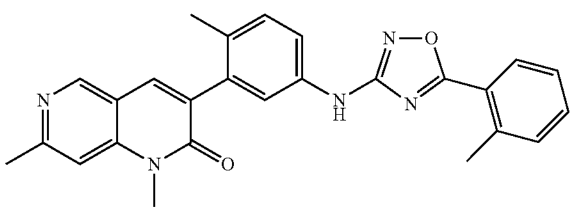 | MS m/z 438.2 (M + 1) | 0.114 | 2 |
| A17 | 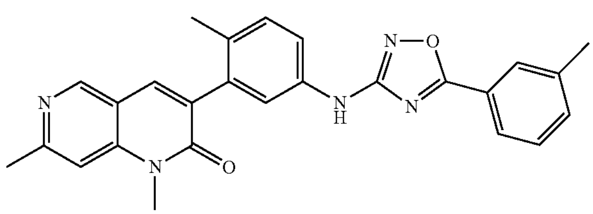 | MS m/z 438.2 (M + 1) | 0.241 | 2 |
| A18 | 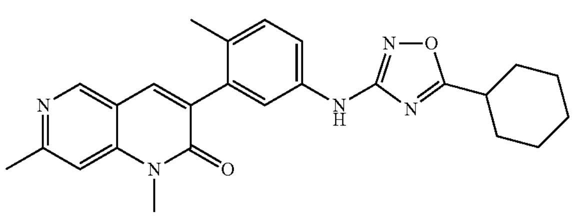 | MS m/z 430.2 (M + 1) | 0.179 | 2 |
| A19 | 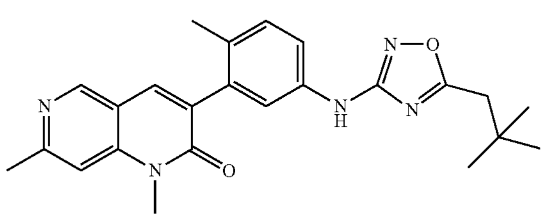 | MS m/z 418.2 (M + 1) | 0.216 | 2 |

TABLE 1-continued

| Compound Number | Structure | ¹H NMR 400 MHz and/or MS m/z | IC$_{50}$ Mo7e (μM) | Synthesis Method |
|---|---|---|---|---|
| A20 | 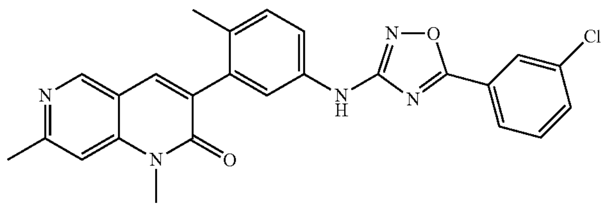 | ¹H NMR (400 MHz, CDCl$_3$) δ 8.65 (s, 1H), 8.0 (t, 1.8 Hz, 1H), 7.9 (dt, J = 7.8, 1.3 Hz, 1H), 7.65 (s, 1H), 7.5 (dq, J = 8.1, 1.1 Hz, 1H), 7.4 (t, J = 7.9, Hz, 1H), 7.3 (m, 2H), 7.2 (m, 1H), 7.04 (s, 1H), 6.68 (s, 1H), 3.67 (s, 3H), 2.65 (s, 3H), 2.14 (s, 3H) MS m/z 458.1, 460.1 (M + 1) | 0.33 | 2 |
| A21 | 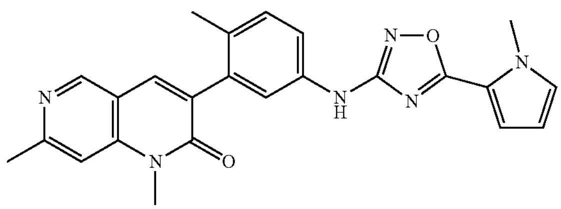 | MS m/z 427.2 (M + 1) | 0.129 | 3 |
| A22 | 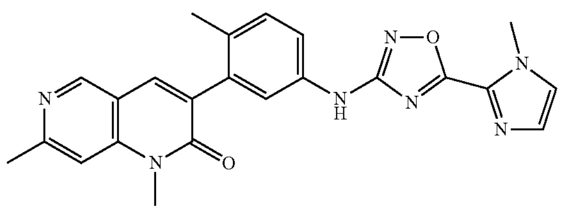 | ¹H NMR (400 MHz, DMSO) δ 10.07 (s, 1H), 9.05 (s, 1H), 8.05 (s, 1H), 7.75 (s, 1H), 7.61 (s, 1H), 7.40-7.50 (m, 2H), 7.22-7.28 (m, 2H), 4.06 (s, 3H), 2.72 (s, 3H), 2.51 (s, 3H), 2.10 (s, 3H) MS m/z 428.2 (M + 1) | 0.36 | 2 |
| A23 | 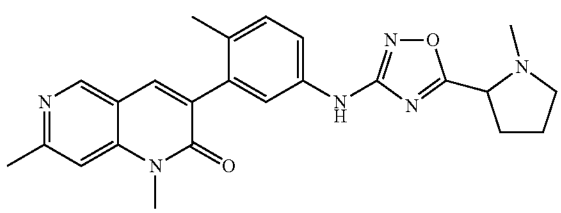 | MS m/z 431.1 (M + 1) | 0.208 | 3 |
| A24 | 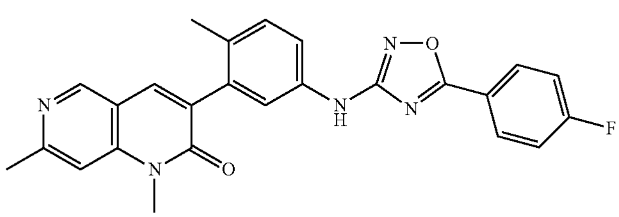 | ¹H NMR (400 MHz, DMSO) δ 10.05 (s, 1H), 8.99 (s, 1H), 8.09-8.15 (m, 2H), 8.03 (s, 1H), 7.68 (s, 1H), 7.40-7.52 (m, 3H), 7.39 (s, 1H), 7.26 (d, J = 8.0 Hz, 1H), 2.69 (s, 3H), 2.51 (s, 3H), 2.10 (s, 3H) MS m/z 442.1 (M + 1) | 0.036 | 3 |
| A25 | 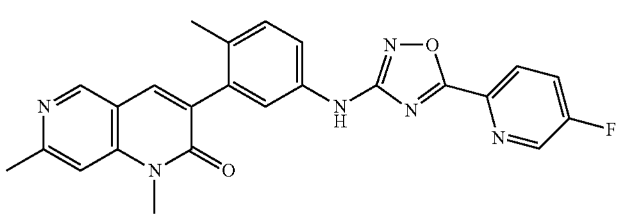 | ¹H NMR (400 MHz, DMSO) δ 10.12 (s, 1H), 9.03 (s, 1H), 8.83 (s, 1H), 8.26 (m, 1H), 7.98-8.07 (m, 2H), 7.73 (s, 1H), 7.43-7.48 (m, 1H), 7.40 (s, 1H), 7.27 (d, J = 8.8 Hz, 1H), 2.71 (s, 3H), 2.51 (s, 3H), 2.10 (s, 3H) MS m/z 443.1 (M + 1) | 0.082 | 3 |

TABLE 1-continued

| Compound Number | Structure | $^1$H NMR 400 MHz and/or MS m/z | IC$_{50}$ Mo7e (μM) | Synthesis Method |
|---|---|---|---|---|
| A26 | 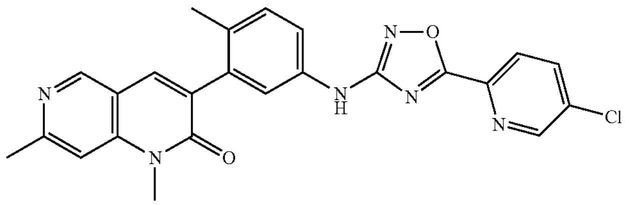 | $^1$H NMR (400 MHz, DMSO) δ 10.13 (s, 1H), 9.03 (s, 1H), 8.88 (s, 1H), 8.15-8.26 (m, 2H), 8.05 (s, 1H), 7.73 (s, 1H), 7.46 (d, J = 8.4 Hz, 1H), 7.40 (s, 1H), 7.27 (d, J = 8.4 Hz, 1H), 2.71 (s, 3H), 2.51 (s, 3H), 2.10 (s, 3H) MS m/z 459.3, 461.3 (M + 1) | 0.027 | 3 |
| A27 | 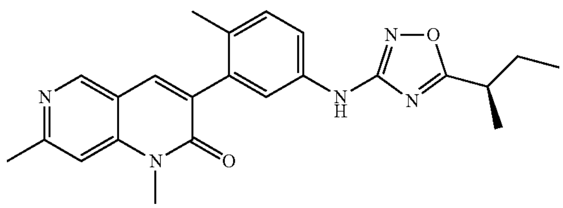 | $^1$H NMR (400 MHz, DMSO) δ 9.87 (s, 1H), 9.01 (s, 1H), 8.02 (s, 1H), 7.72 (s, 1H), 7.36-7.42 (m, 1H), 7.33 (s, 1H), 7.20-7.25 (m, 1H), 2.97-3.04 (m, 1H), 2.70 (s, 3H), 2.51 (s, 3H), 2.08 (s, 3H), 1.71 (m, 2H), 1.29 (d, J = 6.8 Hz, 3H), 0.89 (t, J = 7.6 Hz, 3H) MS m/z 404.2 (M + 1) | 0.054 | 3 |
| A28 | 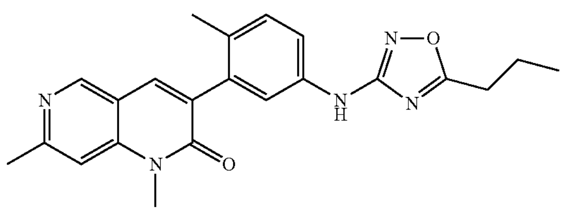 | $^1$H NMR (400 MHz, DMSO) δ 9.83 (s, 1H), 9.02 (s, 1H), 8.02 (s, 1H), 7.73 (s, 1H), 7.39 (d, J = 8.4 Hz, 1H), 7.33 (s, 1H), 7.22 (d, J = 8.4 Hz, 1H), 2.81 (t, J = 7.6 Hz, 2H), 2.71 (s, 3H), 2.51 (s, 3H), 2.08 (s, 3H), 1.75 (m, 2H), 0.97 (t, J = 7.6 Hz, 3H) MS m/z 390.2 (M + 1) | 0.05 | 3 |
| A29 | 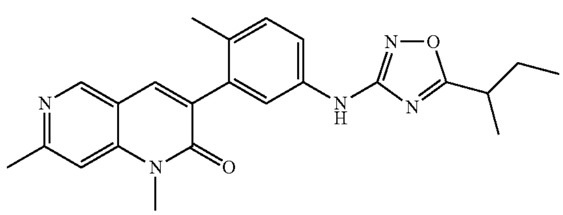 | $^1$H NMR (400 MHz, DMSO) δ 9.87 (s, 1H), 9.01 (s, 1H), 8.02 (s, 1H), 7.72 (s, 1H), 7.36-7.42 (m, 1H), 7.33 (s, 1H), 7.20-7.25 (m, 1H), 2.97-3.04 (m, 1H), 2.70 (s, 3H), 2.51 (s, 3H), 2.08 (s, 3H), 1.71 (m, 2H), 1.29 (d, J = 6.8 Hz, 3H), 0.89 (t, J = 7.6 Hz, 3H) MS m/z 404.2 (M + 1) | 0.058 | 3 |
| A30 | 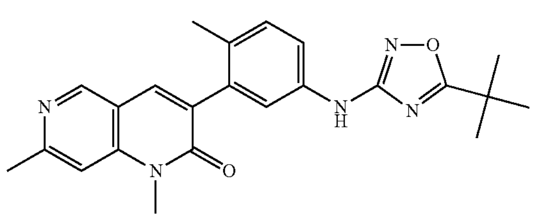 | $^1$H NMR (400 MHz, DMSO) δ 9.90 (s, 1H), 9.01 (s, 1H), 8.01 (s, 1H), 7.71 (s, 1H), 7.39-7.41 (m, 1H), 7.32 (s, 1H), 7.20-7.25 (d, J = 8.4 Hz, 1H), 2.70 (s, 3H), 2.51 (s, 3H), 2.08 (s, 3H), 1.38 (s, 9H) MS m/z 404.2 (M + 1) | 0.245 | 3 |
| A31 | 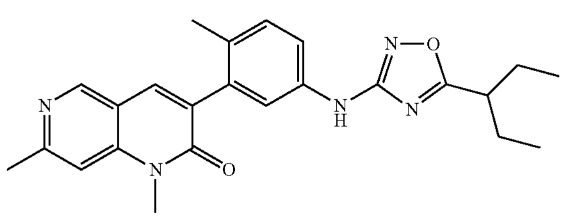 | $^1$H NMR (400 MHz, DMSO) δ 9.89 (s, 1H), 9.02 (s, 1H), 8.02 (s, 1H), 7.73 (s, 1H), 7.36-7.41 (m, 1H), 7.34 (s, 1H), 7.23 (d, J = 8.4 Hz, 1H), 2.83 (m, 1H), 2.71 (s, 3H), 2.51 (s, 3H), 2.08 (s, 3H), 1.72 (m, 4H), 0.85 (t, J = 8.8 Hz, 6H) MS m/z 418.2 (M + 1) | 0.105 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A32 | 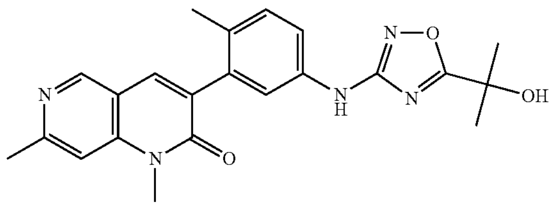 | ¹H NMR (400 MHz, d$_4$-MeOH) δ 8.90 (s, 1H), 7.94 (s, 1H), 7.81 (s, 1H), 7.62 (dd, J = 8.4 Hz, 1H), 7.52 (d, J = 8, 4 Hz, 1H), 7.35 (d, J = 4 Hz, 1H), 7.26 (dd, J = 8, 4 Hz, 1H), 7.14 (d, J = 8 Hz, 1H), 3.79 (s, 3H), 2.75 (s, 3H), 2.06 (s, 3H), 1.35 (m, 6H) MS m/z 406.2 (M + 1) | 0.172 | 3 |
| A33 | 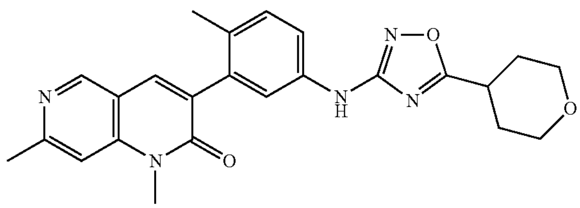 | ¹H NMR (400 MHz, d$_4$-MeOH) δ 9.05 (s, 1H), 8.03 (s, 1H), 7.88 (s, 1H), 7.43 (d, J = 1 Hz, 1H), 7.37 (dd, J = 8, 4 Hz, 1H), 7.25 (d, J = 4 Hz, 1H), 3.99 (dt, J = 12, 4 Hz, 2H), 3.85 (s, 3H), 3.57 (dd, J = 12, 4 Hz, 2H), 3.21 (m, 1H), 2.84 (s, 3H), 2.05-1.86 (m, 4H) MS m/z 432.4 (M + 1) | 0.444 | 3 |
| A34 | 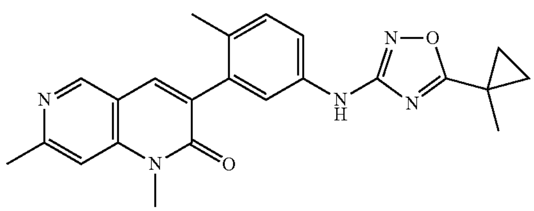 | ¹H NMR (400 MHz, d$_6$-DMSO) δ 9.87 (s, 1H), 9.13 (s, 1H), 8.05 (s, 1H), 7.87 (s, 1H), 7.37 (dd, J = 8, 2 Hz, 1H), 7.30 (d, J = 2 Hz, 1H), 7.22 (d, J = 8 Hz, 2H), 3.70 (s, 3H), 2.75 (s, 3H), 2.07 (s, 3H), 1.47 (s, 3H), 1.27 (m, 2H), 1.08 (m, 2H) MS m/z 402.4 (M + 1) | 0.083 | 3 |
| A35 | 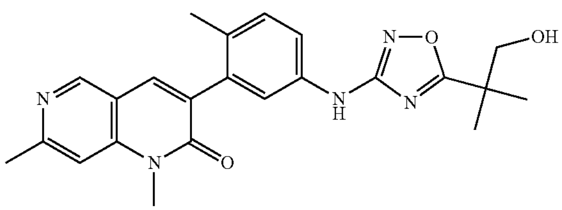 | ¹H NMR (400 MHz, d$_6$-DMSO) δ 9.86 (s, 1H), 8.81 (s, 1H), 7.93 (s, 1H), 7.43 (s, 1H), 7.37 (dd, J = 8, 2 Hz, 1H), 7.28 (d, J = 2 Hz, 1H), 7.21 (d, J = 8 Hz, 2H), 5.10 (t, J = 5.5 Hz, 1H), 3.65 (s, 3H), 3.55, (d J = 5.5 Hz, 1H) 2.61 (s, 3H), 2.07 (s, 3H), 1.31 (s, 6H) MS m/z 420.4 (M + 1) | 0.181 | 3 |
| A36 | 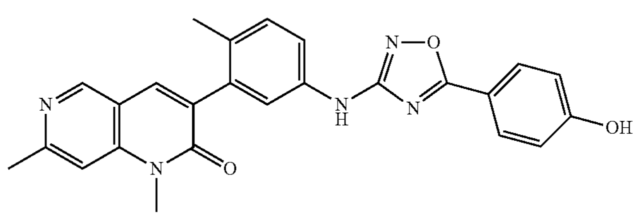 | MS m/z 440.2 (M + 1) | 0.375 | 3 |
| A37 | 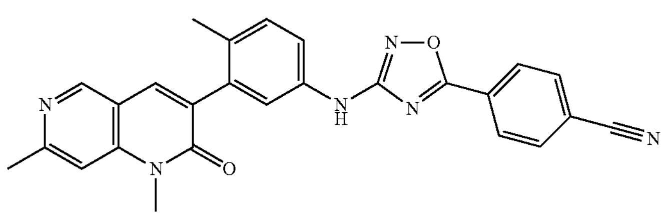 | ¹H NMR (400 MHz, DMSO) δ 10.15 (s, 1H), 8.99 (s, 1H), 8.21 (d, J = 8.0 Hz, 2H), 8.12 (d, J = 8.4 Hz, 2H), 8.03 (s, 1H), 7.68 (s, 1H), 7.43-7.49 (m, 1H), 7.40 (s, 1H), 7.27 (d, J = 8.4 Hz, 1H), 2.69 (s, 3H), 2.51 (s, 3H), 2.10 (s, 3H) MS m/z 449.2 (M + 1) | 0.057 | 3 |

TABLE 1-continued
| Compound Number | Structure | ¹H NMR 400 MHz and/or MS m/z | IC$_{50}$ Mo7e (µM) | Synthesis Method |
|---|---|---|---|---|
| A38 | 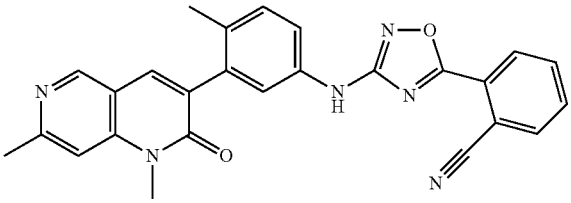 | MS m/z 449.2 (M + 1) | 0.325 | 3 |
| A39 | 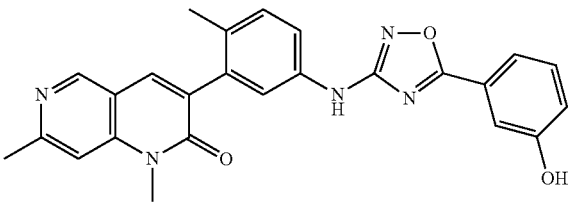 | MS m/z 440.2 (M + 1) | 0.48 | 3 |
| A40 | 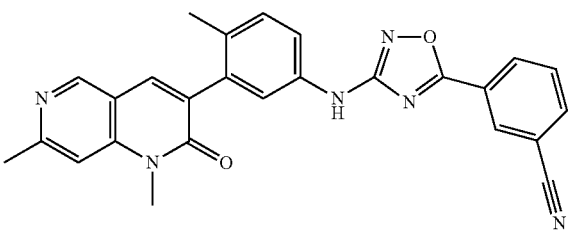 | MS m/z 449.2 (M + 1) | 0.299 | 3 |
| A41 | 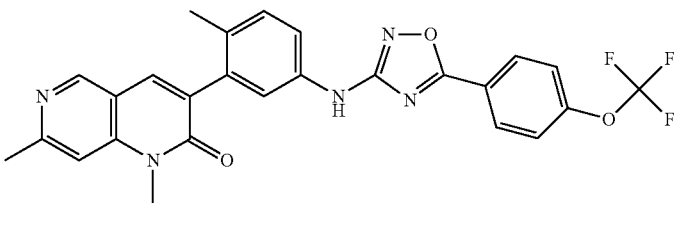 | ¹H NMR (400 MHz, DMSO) δ 10.10 (s, 1H), 9.00 (s, 1H), 8.19 (d, J = 8.8 Hz, 2H), 8.04 (s, 1H), 7.69 (s, 1H), 7.64 (d, J = 8.4 Hz, 2H), 7.46 (d, J = 8.4 Hz, 1H), 7.40 (s, 1H) 7.26 (d, J = 9.2 Hz, 1H), 2.70 (s, 3H), 2.51 (s, 3H), 2.10 (s, 3H) MS m/z 508.2 (M + 1) | 0.053 | 3 |
| A42 | 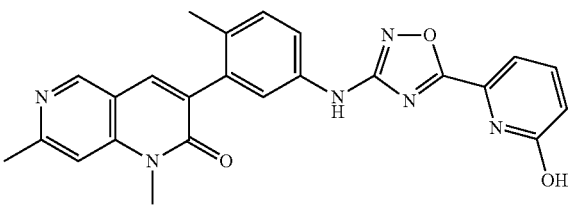 | MS m/z 441.2 (M + 1) | 0.265 | 3 |
| A43 | 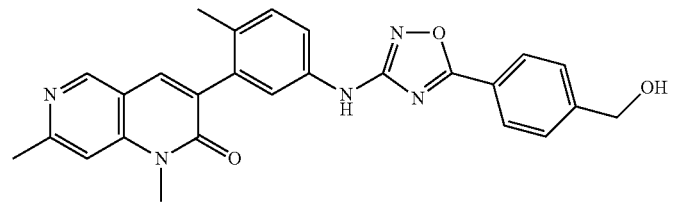 | MS m/z 454.2 (M + 1) | 0.386 | 3 |
| A44 | 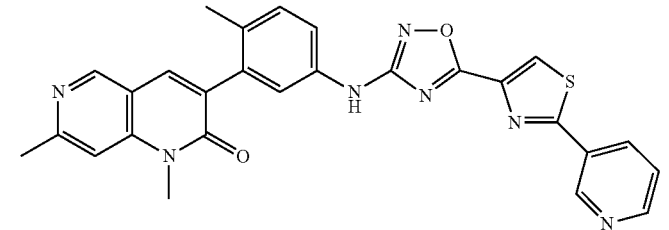 | MS m/z 508.2 (M + 1) | 0.456 | 3 |

TABLE 1-continued
| Compound Number | Structure | ¹H NMR 400 MHz and/or MS m/z | IC₅₀ Mo7e (μM) | Synthesis Method |
|---|---|---|---|---|
| A45 | 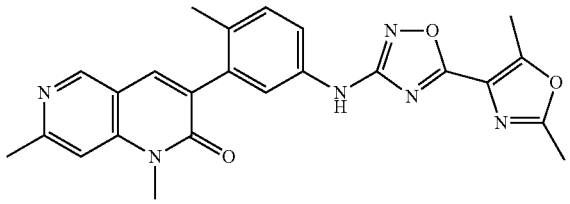 | MS m/z 443.2 (M + 1) | 0.263 | 3 |
| A46 | 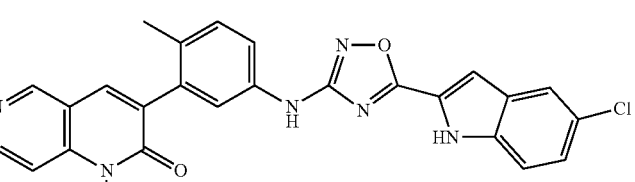 | MS m/z 497.3, 499.3 (M + 1) | 0.338 | 3 |
| A47 | 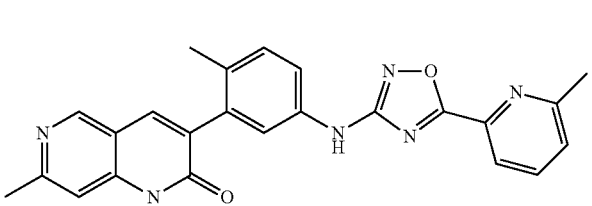 | ¹H NMR (400 MHz, DMSO) δ 10.10 (s, 1H), 9.01 (s, 1H), 8.05 (s, 1H), 7.96-8.00 (m, 2H), 7.71 (s, 1H), 7.57 (m, 1H), 7.47 (d, J = 8.4 Hz, 1H), 7.38 (s, 1H), 7.27 (d, J = 8.4 Hz, 1H), 2.70 (s, 3H), 2.59 (s, 3H), 2.51 (s, 3H), 2.10 (s, 3H) MS m/z 439.2 (M + 1) | 0.311 | 3 |
| A48 | 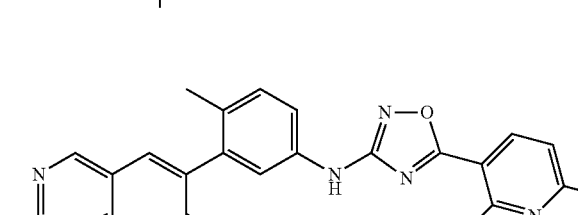 | MS m/z 473.2, 475.2 (M + 1) | 0.361 | 3 |
| A49 | 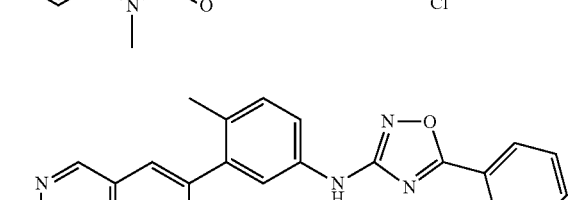 | MS m/z 459.2, 461.2 (M + 1) | 0.333 | 3 |
| A50 | 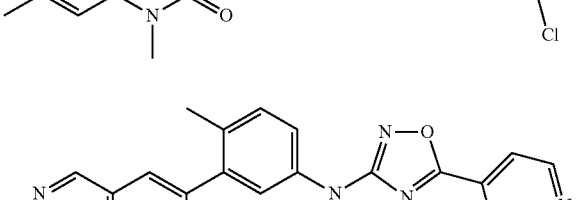 | ¹H NMR (400 MHz, DMSO) δ 10.20 (s, 1H), 9.06 (s, 1H), 8.89 (d, J = 4.8 Hz, 2H), 8.06 (s, 1H), 7.97 (d, J = 4.8 Hz, 2H), 7.77 (s, 1H), 7.47 (d, J = 8.4 Hz, 1H), 7.41 (s, 1H), 7.28 (d, J = 8.0 Hz, 1H), 2.72 (s, 3H), 2.51 (s, 3H), 2.11 (s, 3H) MS m/z 425.2 (M + 1) | 0.271 | 3 |

TABLE 1-continued

| Compound Number | Structure | $^1$H NMR 400 MHz and/or MS m/z | IC$_{50}$ Mo7e (μM) | Synthesis Method |
|---|---|---|---|---|
| A51 | 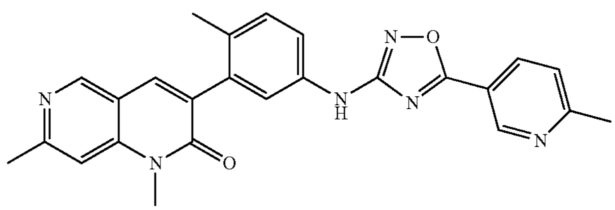 | $^1$H NMR (400 MHz, d6-DMSO) δ 9.27 (d, J = 2.0 Hz, 1H), 9.10 (s, 1H), 8.73 (dd, J = 2.0, 8.4 Hz, 1H), 8.07 (s, 1H), 7.94 (s, 1H), 7.85 (d, J = 8.4 Hz, 1H), 7.50 (d, J = 2.4 Hz, 1H), 7.46 (dd, J = 2.4, 8.4 Hz, 1H), 7.29 (d, J = 8.4 Hz, 1H), 3.85 (s, 3H), 2.87 (s, 3H), 2.79 (s, 3H), 2.19 (s, 3H) MS m/z 439.2 (M + 1) | 0.119 | 3 |
| A52 | 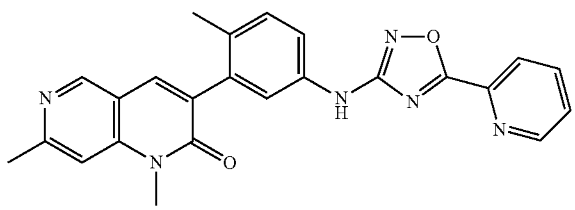 | $^1$H NMR (400 MHz, d$_6$-DMSO) δ 10.18 (s, 1H), 9.17 (bs, 1H), 8.82 (m, 1H), 8.18 (m, 1H), 8.10 (m, 2H), 7.92 (bs, 1H), 7.72 (m, 1H), 7.47 (dd, J = 8. 2 Hz, 1H), 7.43 (d, J,= 2 Hz, 1H), 7.29 (d, J = 8 Hz, 1H), 3.72 (s, 3H), 2.70 (s, 3H), 2.11 (s, 3H) MS m/z 425.1 (M + 1) | 0.068 | 3 |
| A53 | 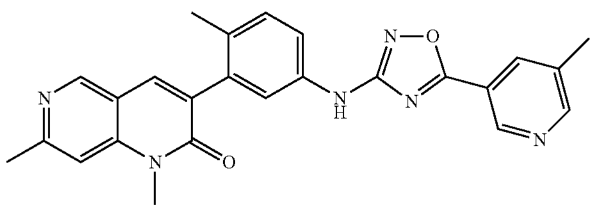 | MS m/z 439.2 (M + 1) | 0.427 | 3 |
| A54 | 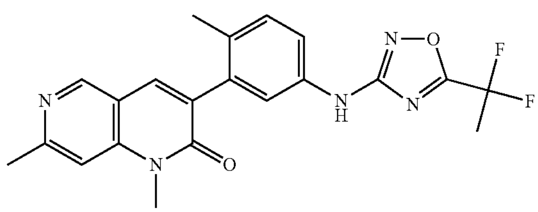 | $^1$H NMR (400 MHz, DMSO) δ 10.27 (s, 1H), 9.00 (s, 1H), 8.03 (s, 1H), 7.70 (s, 1H), 7.42 (d, J = 8.4 Hz, 1H), 7.33 (s, 1H), 7.27 (d, J = 8.0 Hz, 1H), 2.70 (s, 3H), 2.51 (s, 3H), 2.16 (t, J = 19.6 Hz, 3H), 2.10 (s, 3H) MS m/z 412.2 (M + 1) | 0.148 | 3 |
| A55 | 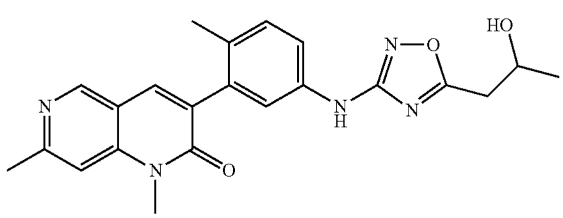 | MS m/z 406.6 (M + 1) | 0.294 | 3 |
| A56 | 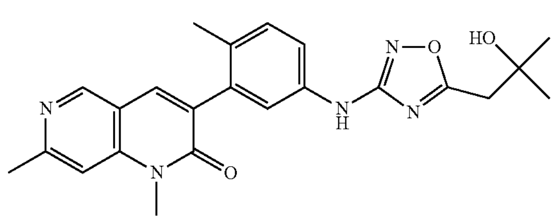 | MS m/z 420.4 (M + 1) | 0.23 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A57 | 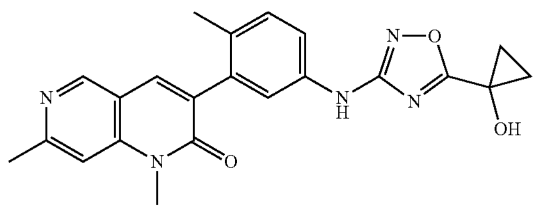 | MS m/z 404.4 (M + 1) | 0.185 | 3 |
| A58 | 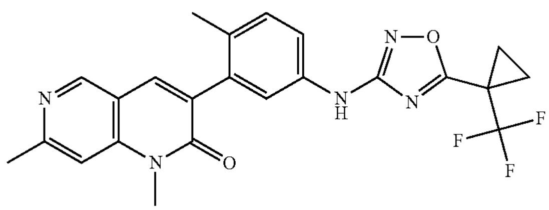 | MS m/z 456.6 (M + 1) | 0.399 | 3 |
| A59 | 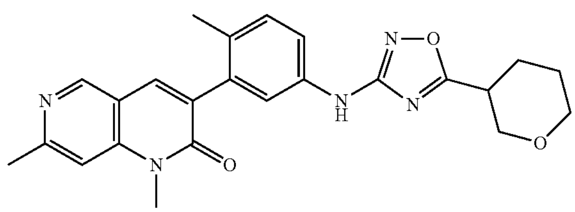 | ¹H NMR (400 MHz, d$_4$-MeOH) δ 9.02 (s, 1H), 8.01 (s, 1H), 7.85 (s, 1H), 7.41 (d, J = 1 Hz, 1H), 7.33 (dd, J = 8, 4 Hz, 1H), 7.22 (d, J = 4 Hz, 1H), 4.08 (dd, J = 11, 4 Hz, 1H), 3.87-3.80 (m, 1H) 3.83 (s, 3H), 3.75 (dd, J = 12, 8 Hz, 1H), 3.59-3.53 (m, 1H), 3.15 (m, 1H), 2.15 (s, 3H), 2.05-1.60 (m, 4H)<br>MS m/z 432.4 (M + 1) | 0.233 | 3 |
| A60 | 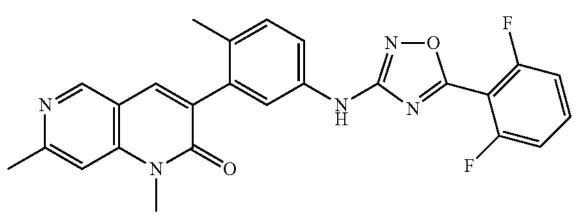 | MS m/z 460.1 (M + 1) | 0.082 | 3 |
| A61 | 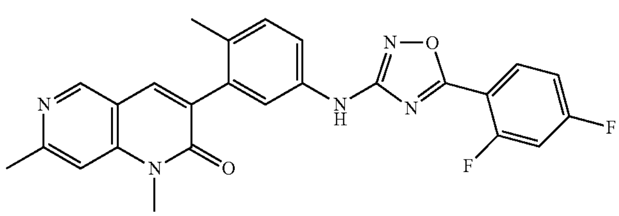 | MS m/z 460.0 (M + 1) | 0.097 | 3 |
| A62 | 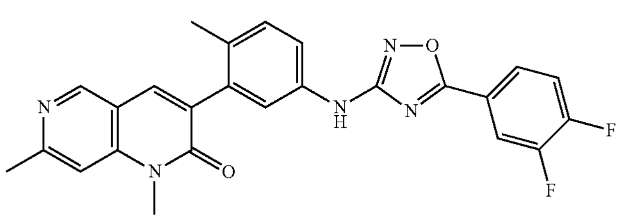 | MS m/z 460.4 (M + 1) | 0.126 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A63 | 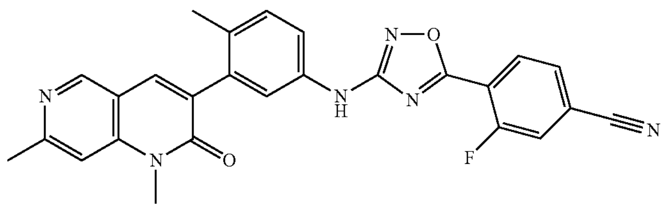 | MS m/z 467.2 (M + 1) | 0.123 | 3 |
| A64 | 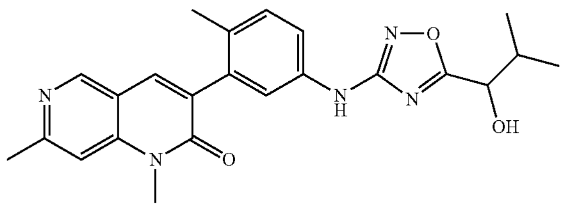 | ¹H NMR (400 MHz, CD$_4$OD) δ 8.76 (s, 1H), 7.93 (s, 1H), 7.47 (s, 1H), 7.39 (dd, J = 8, 2 Hz, 1H), 7.36 (d, J = 2 Hz, 1H), 7.22 (d, J = 8 Hz, 1H), 4.51 (d, J = 6 Hz, 1H), 3.76 (s, 3H), 2.69 (s, 3H), 2.16 (m, 1H), 2.14 (s, 3H), 1.02 (d, J = 6 Hz, 3H), 0.94 (d, J = 6 Hz, 3H) MS m/z 420.4 (M + 1) | 0.118 | 3 |
| A65 | 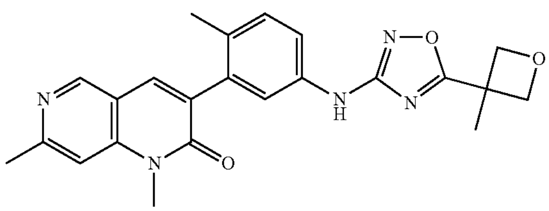 | ¹H NMR (400 MHz, DMSO) δ 9.98 (s, 1H), 9.00 (s, 1H), 8.01 (s, 1H), 7.70 (s, 1H), 7.42 (dd, J = 2.4, 8.4 Hz, 1H), 7.33 (d, J = 2.4 Hz, 1H), 7.24 (m, 1H), 4.89 (d, J = 6.0 Hz, 2H), 4.55 (d, J = 6.0 Hz, 2H), 2.70 (s, 3H), 2.51 (s, 3H), 2.08 (s, 3H), 1.74 (s, 3H) MS m/z 418.2 (M + 1) | 0.413 | 3 |
| A66 | 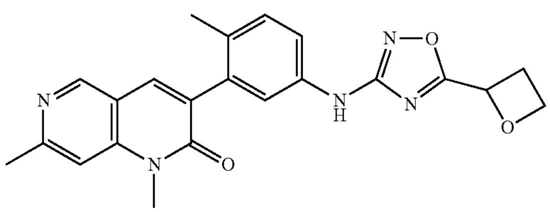 | MS m/z 404.2 (M + 1) | 0.143 | 3 |
| A67 | 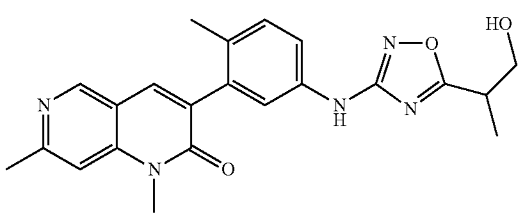 | ¹H NMR (400 MHz, d6-DMSO) δ 9.06 (s, 1H), 8.03 (s, 1H), 7.91 (s, 1H), 7.42 (d, J = 2.4 Hz, 1H), 7.35 (dd, J = 2.4, 8.0 Hz, 1H), 7.23 (d, J = 8.4 Hz, 1H), 3.82 (m, 2H), 3.35 (s, 3H), 3.18 (m, 1H), 2.86 (s, 3H), 2.16 (s, 3H), 1.35 (d, J = 7.2 Hz, 3H) MS m/z 406.2 (M + 1) | 0.299 | 3 |
| A68 | 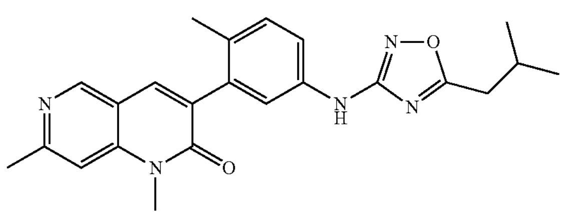 | ¹H NMR (400 MHz, d$_4$-MeOH) δ 8.92 (s, 1H), 7.92 (s, 1H), 7.73 (s, 1H), 7.33 (d, J = 1 Hz, 1H), 7.24 (dd, J = 8, 4 Hz, 1H), 7.14 (d, J = 4 Hz, 1H), 3.72 (s, 3H), 2.72 (s, 3H), 2.60 (d, J = 8 Hz, 2H), 2.10-2.01 (m, 1H), 2.06 (s, 3H), 0.92 (d, J = 8 Hz, 6H) MS m/z 404.5 (M + 1) | 0.128 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A69 | 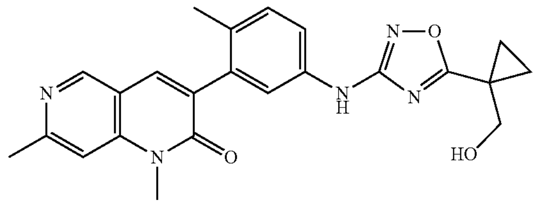 | ¹H NMR (400 MHz, d6-DMSO) δ 9.07 (s, 1H), 8.03 (s, 1H), 7.91 (s, 1H), 7.41 (d, J = 2.4 Hz, 1H), 7.33 (dd, J = 2.4, 8.4 Hz, 1H), 7.23 (d, J = 8.4 Hz, 1H), 3.87 (s, 2H), 3.83 (s, 3H), 2.86 (s, 3H), 2.16 (s, 3H), 1.35 (m, 2H), 1.21 (m, 2H) MS m/z 418.2 (M + 1) | 0.148 | 3 |
| A70 | 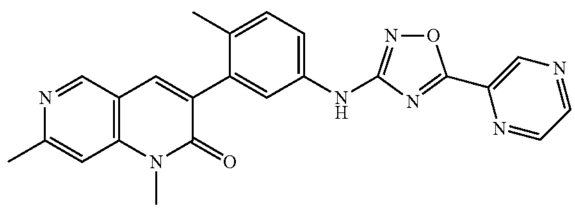 | ¹H NMR (400 MHz, d$_4$-MeOH) δ 9.30 (d, J = 2 Hz, 1H), 8.94 (s, 1H), 8.75 (d, J = 2 Hz, 1H), 8.71 (dd, J = 4, 2 Hz, 1H), 7.95 (s, 1H), 7.75 (s, 1H), 7.42 (d, J = 2 Hz, 1H), 7.34 (dd, J = 4, 2 Hz, 1H), 7.19 (d, J = 8 Hz, 1H), 3.73 (s, 3H), 2.73 (s, 3H), 2.08 (s, 3H) MS m/z 426.5 (M + 1) | 0.211 | 3 |
| A71 | 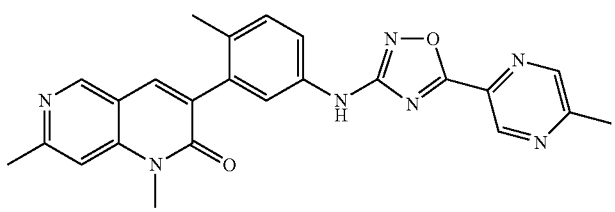 | MS m/z 440.2 (M + 1) | 0.424 | 3 |
| A72 | 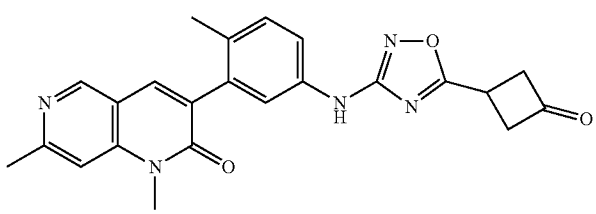 | MS m/z 416.5 (M + 1) | 0.204 | 3 |
| A73 | 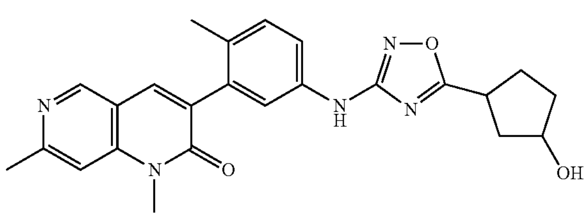 | MS m/z 432.6 (M + 1) | 0.178 | 3 |
| A74 | 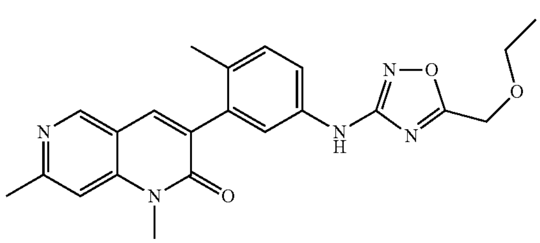 | MS m/z 406.5 (M + 1) | 0.296 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A75 | 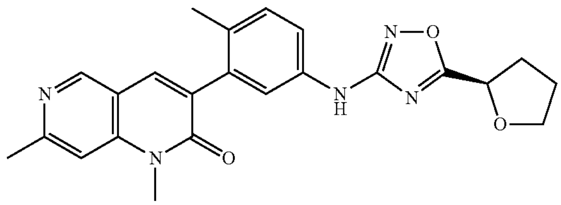 | ¹H NMR (400 MHz, d$_4$-MeOH) δ 9.07 (s, 1H), 8.04 (s, 1H), 7.91 (s, 1H), 7.45 (d, J = 4 Hz, 1H), 7.36 (dd, J = 8, 4 Hz, 1H), 7.25 (d, J = 4 Hz, 1H), 5.10 (dd, J = 8, 4 Hz, 1H), 4.03 (dd, J = 12, 8 Hz, 1H), 3.96 (dd, J = 12, 8 Hz, 1H), 3.83 (s, 3H), 2.85 (s, 3H), 2.41-2.34 (m, 1H), 2.28-2.20 (m, 1H), 2.16 (s, 3H), 2.12-2.03 (m, 2H) MS m/z 418.5 (M + 1) | 0.04 | 3 |
| A76 | 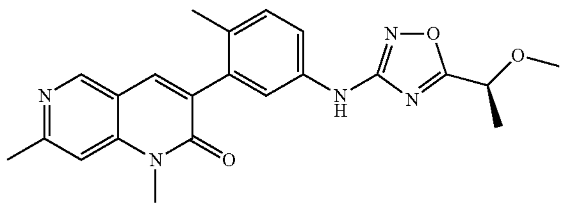 | ¹H NMR (400 MHz, d$_6$-DMSO) δ 9.94 (s, 1H), 8.81 (s, 1H), 7.94 (s, 1H), 7.43 (s, 1H) 7.40 (dd, J = 8, 2 Hz, 1H), 7.30 (d, J = 2 Hz, 1H), 7.22 (d, J = 8 Hz, 1H), 4.68 (d, J = 6 Hz, 1H), 3.65 (s, 3H), 3.45 (s, 3H), 2.61 (s, 3H), 2.07 (s, 3H), 1.49 (d, J = 6 Hz, 3H) MS m/z 406.4 (M + 1) | 0.142 | 3 |
| A77 | 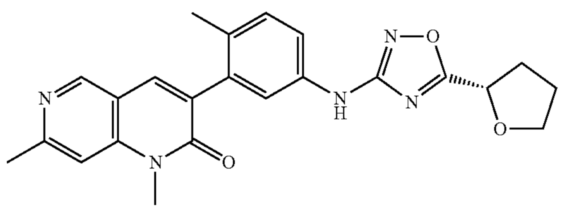 | ¹H NMR (400 MHz, d$_4$-MeOH) δ 9.07 (s, 1H), 8.04 (s, 1H), 7.91 (s, 1H), 7.45 (d, J = 4 Hz, 1H), 7.36 (dd, J = 8, 4 Hz, 1H), 7.25 (d, J = 4 Hz, 1H), 5.10 (dd, J = 8, 4 Hz, 1H), 4.03 (dd, J = 12, 8 Hz, 1H), 3.96 (dd, J = 12, 8 Hz, 1H), 3.83 (s, 3H), 2.85 (s, 3H), 2.41-2.34 (m, 1H), 2.28-2.20 (m, 1H), 2.16 (s, 3H), 2.12-2.03 (m, 2H) MS m/z 418.5 (M + 1) | 0.027 | 3 |
| A78 | 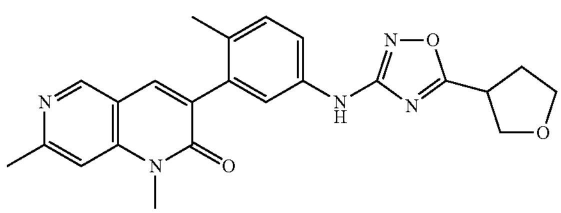 | MS m/z 418.5 (M + 1) | 0.12 | 3 |
| A79 | 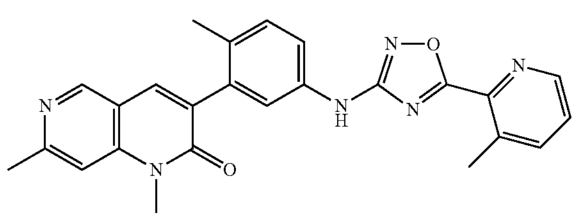 | MS m/z 439.4 (M + 1) | 0.094 | 3 |
| A80 | 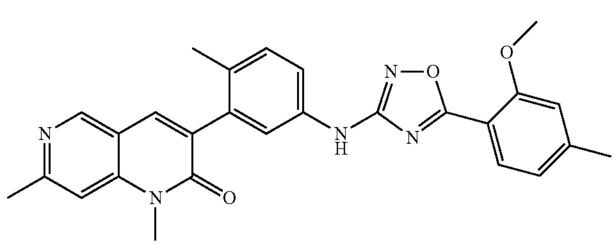 | MS m/z 468.4 (M + 1) | 0.338 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A81 | 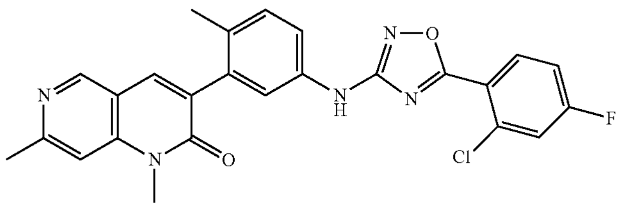 | MS m/z 476.3 (M + 1) | 0.237 | 3 |
| A82 | 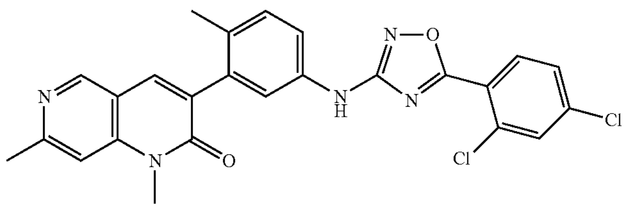 | MS m/z 492.3, 494.2, 496.3 (M + 1) | 0.262 | 3 |
| A83 | 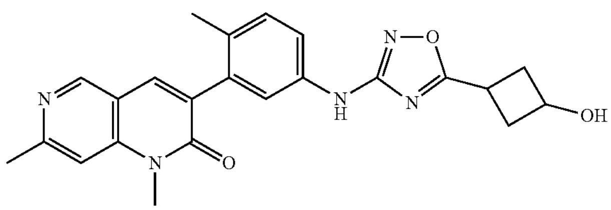 | MS m/z 418.5 (M + 1) | 0.251 | 3 |
| A84 | 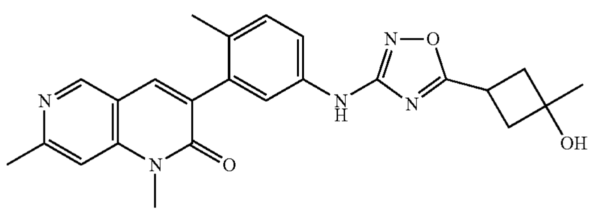 | MS m/z 432.5 (M + 1) | 0.176 | 3 |
| A85 | 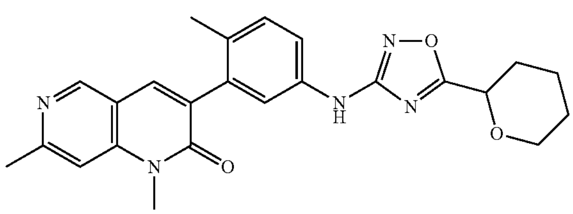 | MS m/z 432.5 (M + 1) | 0.079 | 3 |
| A86 | 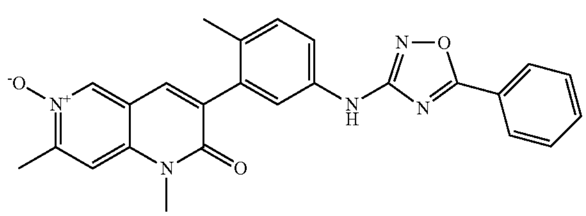 | MS m/z 440.4 (M + 1) | 0.216 | 3 |
| A87 | 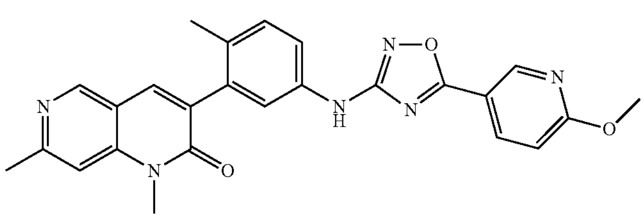 | MS m/z 455.2 (M + 1) | 0.095 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A88 | 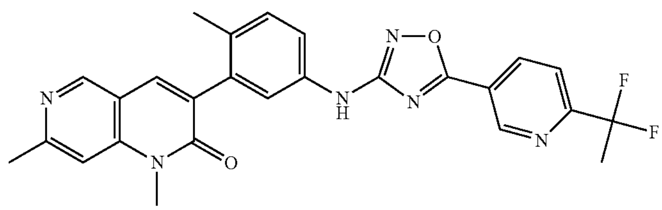 | MS m/z 489.2 (M + 1) | 0.259 | 3 |
| A89 | 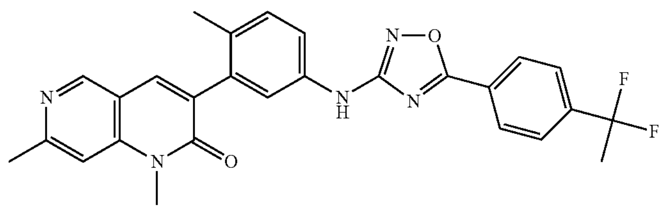 | MS m/z 488.2 (M + 1) | 0.217 | 3 |
| A90 | 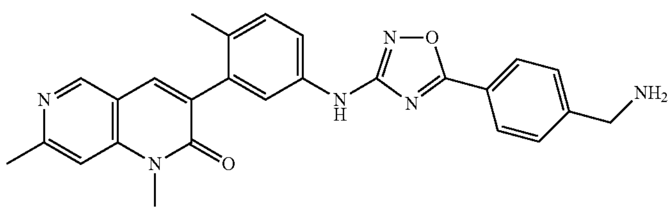 | MS m/z 453.5 (M + 1) | 0.434 | 3 |
| A91 | 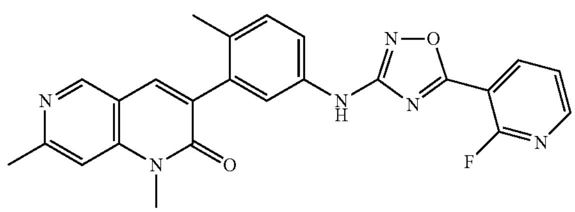 | ¹H NMR (400 MHz, d$_6$-DMSO) δ 10.21 (s, 1H), 9.08 (s, 1H), 8.57 (m, 2H), 8.07 (s, 1H), 7.80 (s, 1H), 7.65 (m, 1H), 7.47 (dd, J = 8, 2 Hz, 1H), 7.41 (d, J = 2 Hz, 1H), 7.28 (d, J = 8 Hz, 1H), 3.71 (s, 3H), 2.73 (s, 3H), 2.05 (s, 3H) MS m/z 443.2 (M + 1) | 0.244 | 3 |
| A92 | 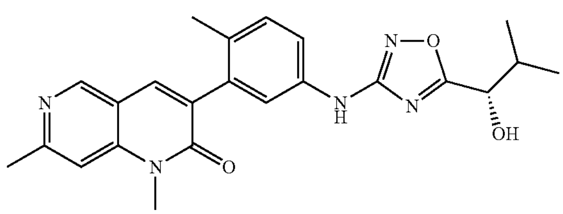 | ¹H NMR (400 MHz, d$_6$-DMSO) δ 9.87 (s, 1H), 8.81 (s, 1H), 7.94 (s, 1H), 7.43 (s, 1H), 7.39 (dd, J = 8, 2 Hz, 1H), 7.30 (d, J = 2 Hz, 1H), 7.21 (d, J = 8 Hz, 1H), 6.02 (d, J = 6 Hz, 1H), 4.48 (bt, J = 6 Hz, 1H), 3.67 (s, 3H), 2.61 (s, 3H), 2.07 (s, 3H) 0.94 (d, J = 6 Hz, 3H), 0.87 (d, J = 6 Hz, 3H) MS m/z 420.4 (M + 1) | 0.104 | 3 |
| A93 | 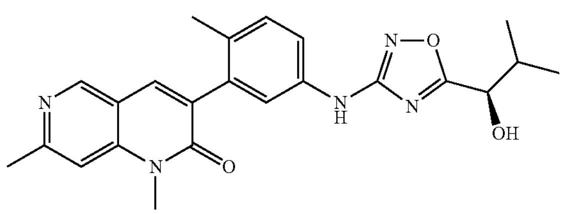 | ¹H NMR (400 MHz, d$_6$-DMSO) δ 9.87 (s, 1H), 8.81 (s, 1H), 7.94 (s, 1H), 7.43 (s, 1H), 7.39 (dd, J = 8, 2 Hz, 1H), 7.30 (d, J = 2 Hz, 1H), 7.21 (d, J = 8 Hz, 1H), 6.02 (d, J = 6 Hz, 1H), 4.48 (bt, J = 6 Hz, 1H), 3.67 (s, 3H), 2.61 (s, 3H), 2.07 (s, 3H) 0.94 (d, J = 6 Hz, 3H), 0.87 (d, J = 6 Hz, 3H) MS m/z 420.4 (M + 1) | 0.283 | 3 |

TABLE 1-continued

| Compound Number | Structure | $^1$H NMR 400 MHz and/or MS m/z | IC$_{50}$ Mo7e (μM) | Synthesis Method |
|---|---|---|---|---|
| A94 | 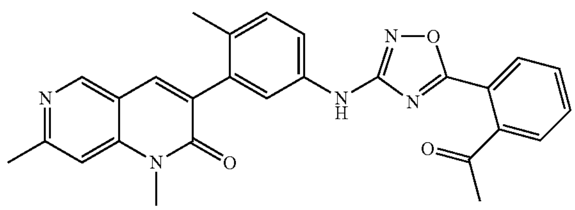 | $^1$H NMR (400 MHz, d$_6$-DMSO) δ 10.00 (s, 1H), 8.99 (s, 1H), 8.04 (s, 1H), 7.91 (d, J = 8 Hz, 1H), 7.85 (d, J = 8 Hz, 1H), 7.70 (m, 2H), 7.69 (s, 1H), 7.42 (m, 2H), 7.25 (m, 1H), 3.68 (s, 3H), 2.69 (s, 3H), 2.57 (s, 3H) 2.09 (s, 3H) MS m/z 466.4 (M + 1) | 0.258 | 3 |
| A95 | 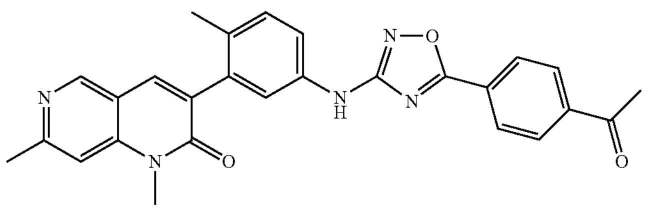 | $^1$H NMR (400 MHz, d$_6$-DMSO) δ 10.11 (s, 1H), 8.99 (s, 1H), 8.18 (m, 4H), 8.03 (s, 1H), 7.67 (s, 1H), 7.47 (dd, J = 8, 2 Hz, 1H), 7.40 (d, J = 2 Hz, 1H), 7.27 (d, J = 8 Hz, 1H), 3.69 (s, 3H), 2.69 (s, 3H), 2.65 (s, 3H) 2.10 (s, 3H) MS m/z 466.4 (M + 1) | 0.31 | 3 |
| A96 | 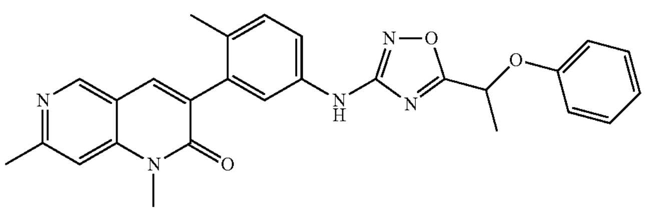 | MS m/z 468.5 (M + 1) | 0.419 | 3 |
| A97 | 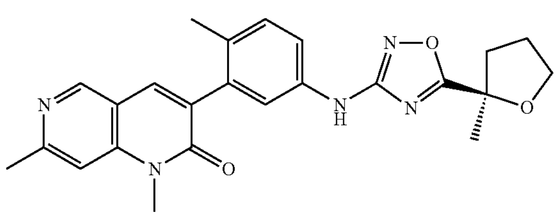 | $^1$H NMR (400 MHz, d$_4$-MeOH) δ 9.03 (s, 1H), 8.02 (s, 1H), 7.85 (s, 1H), 7.42 (d, J = 4 Hz, 1H), 7.35 (dd, J = 8, 4 Hz, 1H), 7.25 (d, J = 4 Hz, 1H), 4.06-3.95 (m, 2H), 3.83 (s, 3H), 2.83 (s, 3H), 2.54-2.48 (m, 1H), 2.16 (s, 3H), 2.12-2.00 (m, 2H), 1.65 (s, 3H) MS m/z 432.5 (M + 1) | 0.16 | 3 |
| A98 | 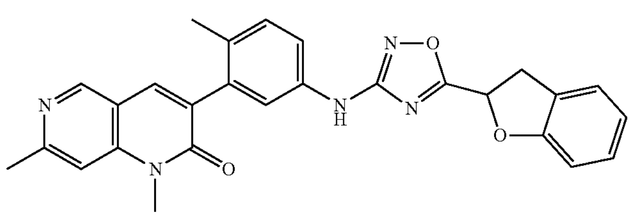 | $^1$H NMR (400 MHz, d$_6$-MeOH) δ 9.02 (s, 1H), 8.01 (s, 1H), 7.85 (s, 1H), 7.42-7.13 (m, 5H), 6.92 (t, J = 4 Hz, 1H), 6.84 (d, J = 4 Hz, 1H), 5.90 (dd, J = 8, 4 Hz, 1H), 3.81 (s, 3H), 3.73 (dd, J = 16, 12 Hz, 1H), 3.61 (dd, J = 16, 4 Hz, 1H), 2.83 (s, 3H), 2.16 (s, 3H) MS m/z 466.5 (M + 1) | 0.389 | 3 |
| A99 | 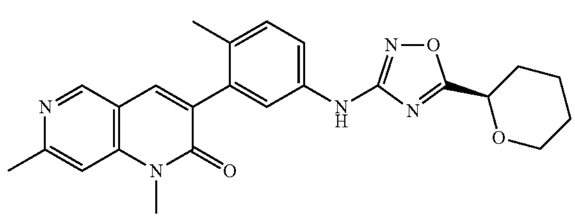 | MS m/z 432.5 (M + 1) | 0.1 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| A100 | 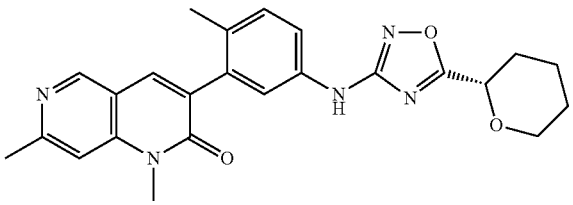 | MS m/z 432.5 (M + 1) | 0.07 | 3 |
| A101 | 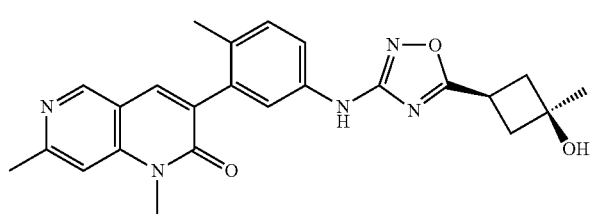 | ¹H NMR (400 MHz, d$_4$-MeOH) δ 9.08 (s, 1H), 8.05 (s, 1H), 7.92 (s, 1H), 7.45 (d, J = 4 Hz, 1H), 7.36 (dd, J = 8, 4 Hz, 1H), 7.25 (d, J = 4 Hz, 1H), 3.83 (s, 3H), 2.83 (s, 3H), 2.49 (s, 2H), 2.46 (s, 2H), 2.16 (s, 3H), 1.43 (s, 3H) MS m/z 432.5 (M + 1) | 0.205 | 3 |
| A102 | 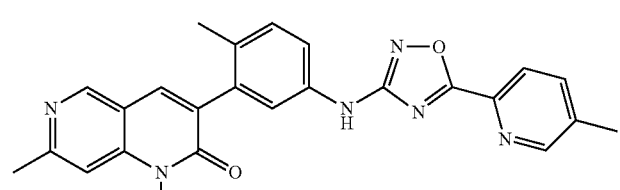 | ¹H NMR (400 MHz, DMSO) δ 10.08 (s, 1H), 9.02 (s, 1H), 8.66 (s, 1H), 8.03-8.10 (m, 2H), 7.90 (d, J = 7.6 Hz, 1H), 7.71 (s, 1H), 7.47 (d, J = 8.4 Hz, 1H), 7.40 (s, 1H), 7.27 (d, J = 8.8 Hz, 1H), 2.70 (s, 3H), 2.51 (s, 3H), 2.42 (s, 3H), 2.10 (s, 3H) MS m/z 439.2 (M + 1) | 0.113 | 3 |
| A103 | 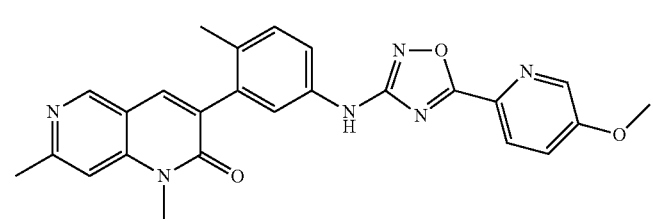 | ¹H NMR (400 MHz, DMSO) δ 10.05 (s, 1H), 9.04 (s, 1H), 8.50 (d, J = 2.8 Hz, 1H), 8.14 (d, J = 8.8 Hz, 1H), 8.05 (s, 1H), 7.74 (s, 1H), 7.64 (dd, J = 2.8, 8.8 Hz, 1H), 7.45 (dd, J = 2.0, 8.0 Hz, 1H), 7.40 (s, 1H), 7.26 (d, J = 8.4 Hz, 1H), 3.95 (s, 3H), 2.71 (s, 3H), 2.51 (s, 3H), 2.10 (s, 3H) MS m/z 455.2 (M + 1) | 0.082 | 3 |
| A104 | 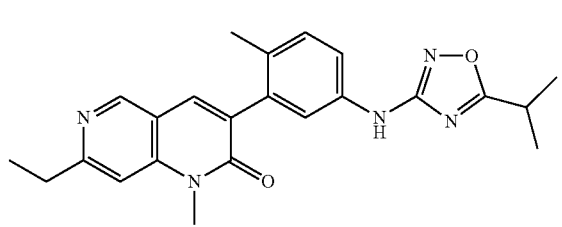 | ¹H NMR (400 MHz, d$_6$-DMSO) δ 9.91 (s, 1H), 9.10 (s, 1H), 8.05 (s, 1H), 7.78 (s, 1H), 7.41 (dd, J = 8, 2 Hz, 1H), 7.33 (d, J = 2 Hz, 1H), 7.23 (d, J = 8 Hz, 1H), 3.72 (s, 3H), 3.19 (m, 1H), 3.01 (q, J = 7.6 Hz, 2H), 2.08 (s, 3H), 1.36 (t, J = 7.6 Hz, 3H), 1.31, (d, J = 6.8 Hz, 6H) MS m/z 404.1 (M + 1) | 0.088 | 3 |
| A105 | 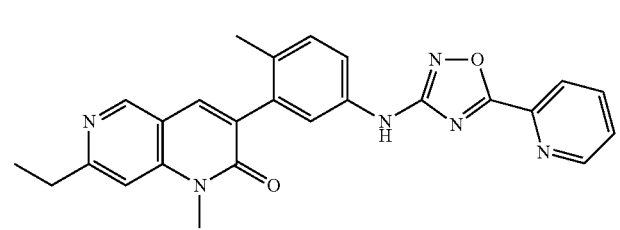 | ¹H NMR (400 MHz, d$_6$-DMSO) δ 10.13 (s, 1H), 9.09 (s, 1H), 8.81 (s, 1H), 8.18 (d, J = 8 Hz, 1H), 8.10 (m, 2H), 7.75 (s, 1H), 7.71 (m, 1H), 7.47 (d, J = 8 Hz, 1H), 7.41 (s, 1H), 7.28 (d, J = 8 Hz, 1H), 3.72 (s, 3H), 3.01 (q, J = 7.6 Hz, 2H), 2.10 (s, 3H), 1.36 (t, J = 7.6 Hz, 3H) MS m/z 439.3 (M + 1) | 0.285 | 3 |

TABLE 1-continued

| Compound Number | Structure | ¹H NMR 400 MHz and/or MS m/z | IC$_{50}$ Mo7e (μM) | Synthesis Method |
|---|---|---|---|---|
| B1 | 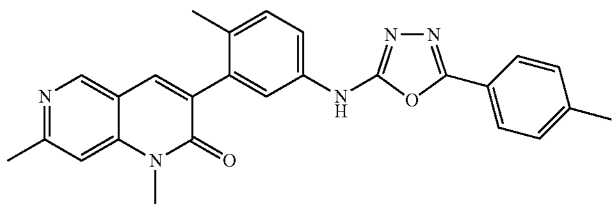 | ¹H NMR (400 MHz, d$_4$-MeOH) δ 9.04 (s, 1H), 8.07 (s, 1H), 7.87 (s, 1H), 7.82 (d, J = 8.2 Hz, 2H), 7.61 (d, J = 2.4 Hz, 1H), 7.42 (dd, J = 8.3, 2.4 Hz, 1H), 7.36 (d, J = 8.1 Hz, 2H), 7.3 (d, J = 8.4 Hz, 1H), 3.82 (s, 3H), 2.84 (s, 3H), 2.42 (s, 3H), 2.19 (s, 3H) MS m/z 438.2 (M + 1) | 0.076 | 6 |
| B2 | 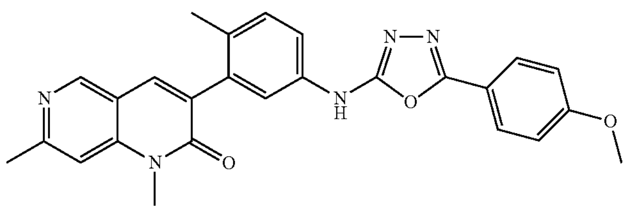 | ¹H NMR (400 MHz, d$_6$-MeOH) δ 9.06 (s, 1H), 8.07 (s, 1H), 7.88 (m, 3H), 7.61 (d, J = 2.4 Hz, 1H), 7.41 (dd, J = 8.3, 2.4 Hz, 1H), 7.3 (d, J = 8.4 Hz, 1H), 7.08 (d, J = 7 Hz, 2H), 3.87 (s, 3H), 3.83 (s, 3H), 2.85 (s, 3H), 2.19 (s, 3H) MS m/z 454.2 (M + 1) | 0.085 | 6 |
| B3 | 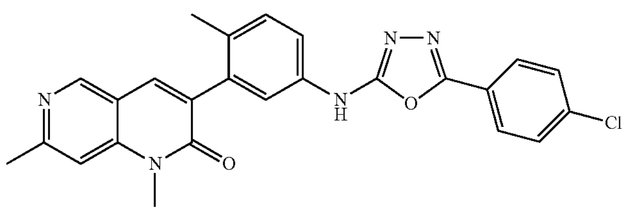 | ¹H NMR (400 MHz, d$_4$-MeOH) δ 9.07 (s, 1H), 8.08 (s, 1H), 7.93 (d, J = 8.6 Hz, 2H), 7.9 (s, 1H), 7.63 (d, J = 2.4 Hz, 1H), 7.57 (d, J = 8.6 Hz, 2H), 7.42 (dd, J = 8.3, 2.4 Hz, 1H), 7.31 (d, J = 8.4 Hz, 1H), 3.84 (s, 3H), 2.85 (s, 3H), 2.2 (s, 3H) MS m/z 458.1, 460.1 (M + 1) | 0.088 | 6 |
| B4 | 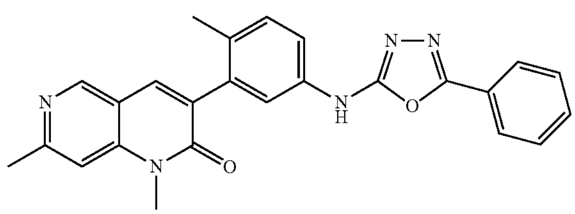 | ¹H NMR (400 MHz, d$_4$-MeOH) δ 9.07 (s, 1H), 8.09 (s, 1H), 7.96 (m, 2H), 7.89 (s, 1H), 7.64 (d, J = 2.4 Hz, 1H), 7.55 (m, 3H), 7.43 (dd, J = 8.3, 2.4 Hz, 1H), 7.32 (d, J = 8.3 Hz, 1H), 3.84 (s, 3H), 2.85 (s, 3H), 2.2 (s, 3H) MS m/z 424.3 (M + 1) | 0.105 | 6 |
| B5 | 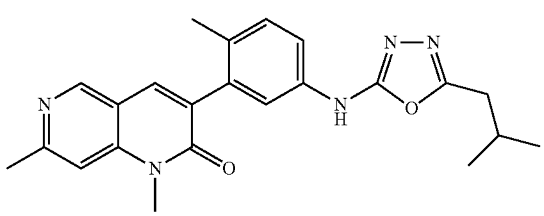 | MS m/z 404.2 (M + 1) | 0.108 | 6 |
| B6 | 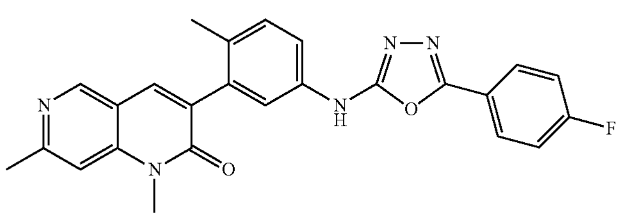 | ¹H NMR (400 MHz, d$_6$-MeOH) δ 9.06 (s, 1H), 8.08 (s, 1H), 8 (dd, J = 6.9, 5.2 Hz, 2H), 7.87 (s, 1H), 7.63 (d, J = 2.4 Hz, 1H), 7.43 (dd, J = 8.3, 2.3 Hz, 1H), 7.31 (m, 3H), 3.84 (s, 3H), 2.84 (s, 3H), 2.2 (s, 3H) MS m/z 442.2 (M + 1) | 0.121 | 6 |

TABLE 1-continued

| Compound Number | Structure | ¹H NMR 400 MHz and/or MS m/z | IC$_{50}$ Mo7e (μM) | Synthesis Method |
|---|---|---|---|---|
| B7 | 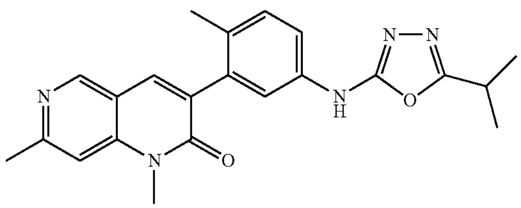 | MS m/z 390.3 (M + 1) | 0.162 | 6 |
| B8 | 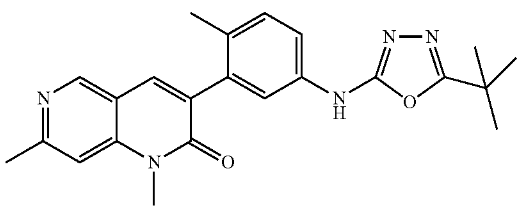 | MS m/z 404.2 (M + 1) | 0.211 | 6 |
| B9 | 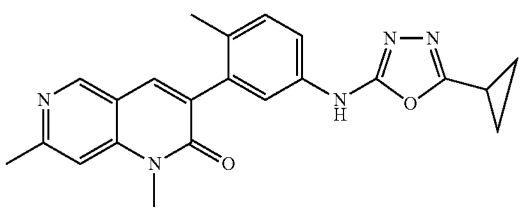 | MS m/z 388.2 (M + 1) | 0.334 | 6 |
| B10 | 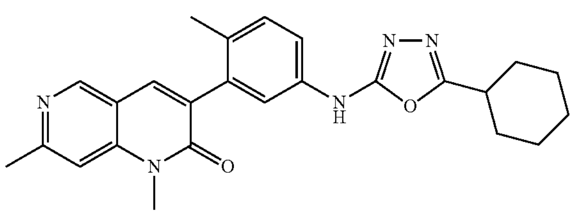 | ¹H NMR (400 MHz, d$_4$-MeOH) δ 9.06 (s, 1H), 8.05 (s, 1H), 7.89 (s, 1H), 7.53 (d, J = 2.4 Hz, 1H), 7.36 (dd, J = 8.3, 2.4 Hz, 1H), 7.26 (d, J = 8.4 Hz, 1H), 3.82 (s, 3H), 2.85 (s, 3H), 2.17 (s, 3H), 2.07 (dd, J = 13.1, 3.1 Hz, 2H), 1.84 (dt, J = 13, 3.6 Hz, 2H), 1.74 (dt, J = 8.7, 3.5 Hz, 1H), 1.58 (dq, J = 11.8, 3.1 Hz, 2H), 1.44 (tq, J = 12.6, 3 Hz, 2H), 1.34 (tquin, J = 11.9, 3.1 Hz, 2H)<br>MS m/z 430.2 (M + 1) | 0.378 | 6 |
| C1 | 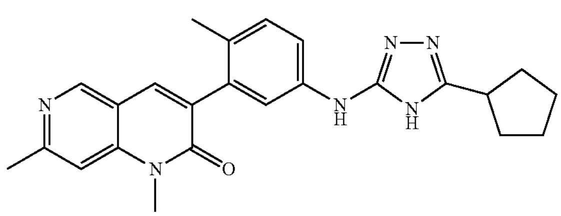 | MS m/z 415.2 (M + 1) | 0.12 | 7 |
| C2 | 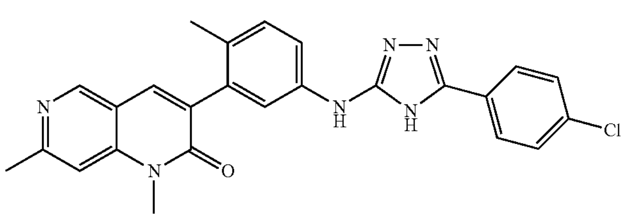 | MS m/z 457.1, 459.1 (M + 1) | 0.256 | 7 |

TABLE 1-continued

| Compound Number | Structure | ¹H NMR 400 MHz and/or MS m/z | IC$_{50}$ Mo7e (μM) | Synthesis Method |
|---|---|---|---|---|
| C3 | 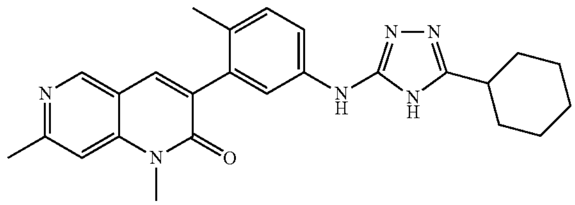 | MS m/z 429.2 (M + 1) | 0.279 | 7 |
| C4 | 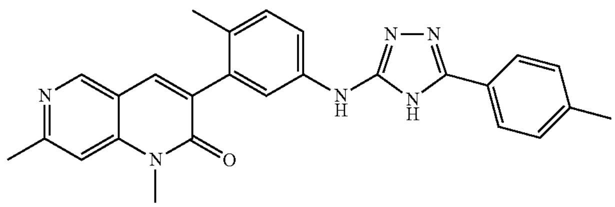 | ¹H NMR (400 MHz, d$_4$-MeOH) δ 9 (s, 1H), 8.02 (s, 1H), 7.85 (s, 1H), 7.81 (d, J = 8.2 Hz,. 2H), 7.47 (s, 1H), 7.42 (d, J = 8.2 Hz, 1H), 7.3 (d, J = 8.2 Hz, 2H), 7.27 (d, J = 8.3 Hz, 1H), 3.79 (s, 3H), 2.84 (s, 3H), 2.4 (s, 3H), 2.17 (s, 3H) MS m/z 437.2 (M + 1) | 0.288 | 7 |
| C5 | 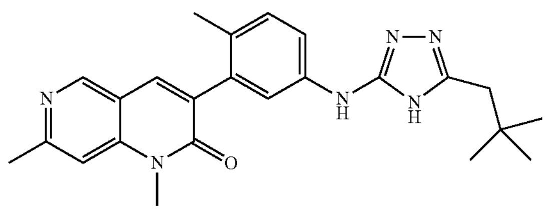 | MS m/z 417.2 (M + 1) | 0.32 | 7 |
| C6 | 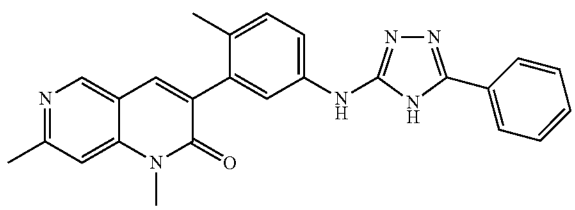 | ¹H NMR (400 MHz, d$_4$-MeOH) δ 9.04 (s, 1H), 8.05 (s, 1H), 7.95 (m, 1H), 7.93 (d, J = 2 Hz, 1H), 7.86 (s, 1H), 7.47 (m, 5H), 7.25 (d, J = 7.9 Hz, 1H), 7.29 (d, J = 8.4 Hz, 1H), 3.83 (s, 3H), 2.84 (s, 3H), 2.17 (s, 3H) MS m/z 423.2 (M + 1) | 0.335 | 7 |
| C7 | 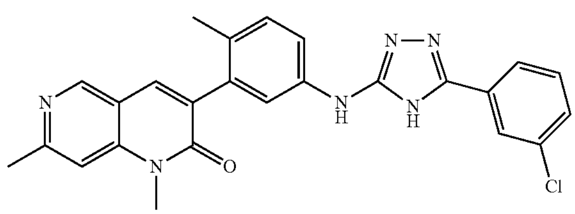 | ¹H NMR (400 MHz, d$_4$-MeOH) δ 9.06 (s, 1H), 8.07 (s, 1H), 7.98 (dd, J = 2.6, 1.6 Hz, 1H), 7.88 (m, 2H), 7.49 (d, J = 2.5 Hz, 1H), 7.44 (m, 3H), 7.27 (d, J = 8.3 Hz, 1H), 3.84 (s, 3H), 2.84 (s, 3H), 2.18 (s, 3H) MS m/z 457.2, 459.2 (M + 1) | 0.378 | 7 |
| C8 | 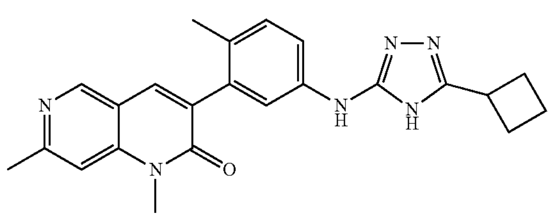 | MS m/z 401.2 (M + 1) | 0.435 | 7 |
| D1 | 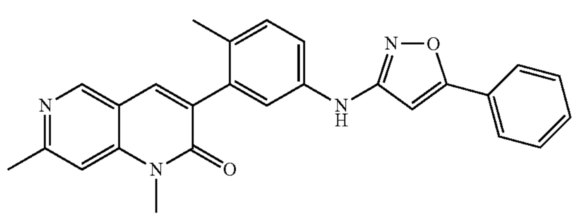 | MS m/z 423.1 (M + 1) | 0.068 | 10 |

TABLE 1-continued

| Compound Number | Structure | ¹H NMR 400 MHz and/or MS m/z | IC$_{50}$ Mo7e (μM) | Synthesis Method |
|---|---|---|---|---|
| D2 | 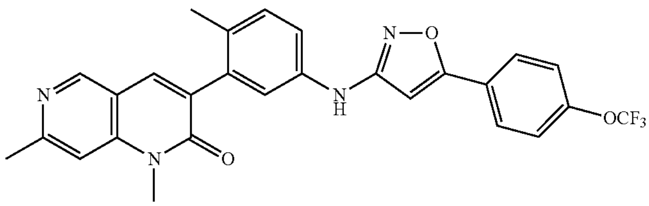 | MS m/z 507.2 (M + 1) | 0.428 | 8 |
| D3 | 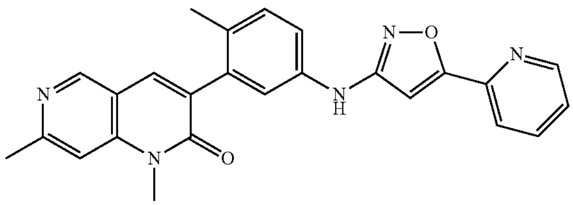 | ¹H NMR (400 MHz, DMSO) δ 9.37 (s, 1H), 9.07 (s, 1H), 8.71 (d, J = 4.4 Hz, 1H), 8.07 (s, 1H), 7.99 (m, 1H), 7.89 (d, J = 8.0 Hz, 1H), 7.79 (s, 1H), 7.51 (m, 1H), 7.45 (d, J = 1.6 Hz, 1H), 7.36 (dd, J = 2.4, 8.0 Hz, 1H), 7.24 (d, J = 8.4 Hz, 1H), 6.70 (s, 1H), 2.73 (s, 3H), 2.51 (s, 3H), 2.10 (s, 3H) MS m/z 424.2 (M + 1) | 0.158 | 8 |
| D4 | 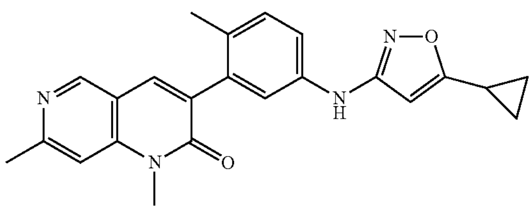 | ¹H NMR (400 MHz, d6-DMSO) δ 9.21 (s, 1H), 9.13 (s, 1H), 8.10 (s, 1H), 7.96 (s, 1H), 7.39 (d, J = 2.4 Hz, 1H), 7.29 (dd, J = 2.4, 8.4 Hz, 1H), 7.19 (d, J = 8.4 Hz, 1H), 5.83 (s, 1H), 3.72 (s, 3H), 2.79 (s, 3H), 2.07 (s, 3H), 2.05 (m, 1H), 1.01 (m, 2H), 0.84 (m, 2H) MS m/z 387.2 (M + 1) | 0.056 | 10 |
| D5 | 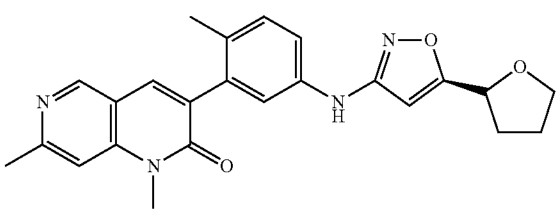 | MS m/z 417.2 (M + 1) | 0.197 | 10 |
| D6 | 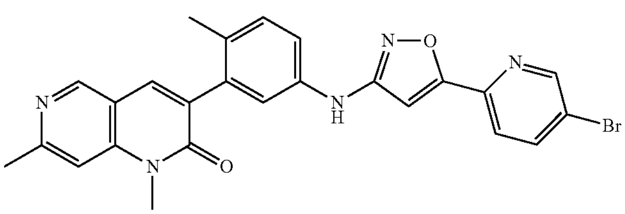 | MS m/z 502.2, 504.2 (M + 1) | 0.229 | 8 |
| D7 | 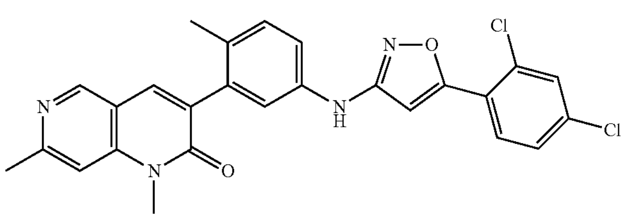 | MS m/z 491.3, 493.2, 495.2 (M + 1) | 0.401 | 8 |

TABLE 1-continued

| Compound Number | Structure | $^1$H NMR 400 MHz and/or MS m/z | IC$_{50}$ Mo7e (μM) | Synthesis Method |
|---|---|---|---|---|
| D8 | 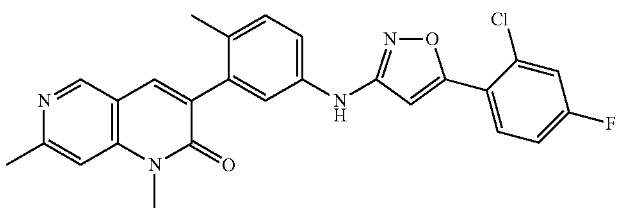 | $^1$H NMR (400 MHz, DMSO) δ 9.36 (s, 1H), 9.04 (s, 1H), 8.05 (s, 1H), 7.93 (m, 1H), 7.67-7.75 (m, 2H), 7.40-7.44 (m, 2H), 7.34 (dd, J = 2.0, 8.4 Hz, 1H), 7.23 (d, J = 8.4 Hz, 1H), 6.69 (s, 1H), 2.71 (s, 3H), 2.51 (s, 3H), 2.09 (s, 3H) MS m/z 475.3, 477.3 (M + 1) | 0.361 | 8 |
| D9 | 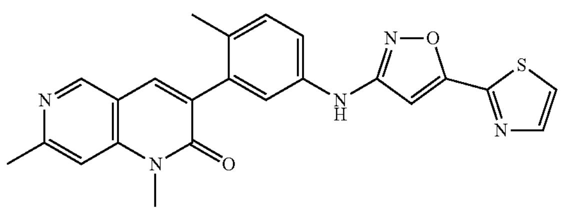 | $^1$H NMR (400 MHz, d6-DMSO) δ 10.73 (s, 1H), 9.19 (s, 1H), 8.11 (s, 1H), 7.93 (s, 1H), 7.87 (d, J = 3.2 Hz, 1H), 7.74 (d, J = 3.2 Hz, 1H), 7.65 (d, J = 2.4 Hz, 1H), 7.61 (s, 1H), 7.53 (dd, J = 2.4, 8.0 Hz, 1H), 7.27 (d, J = 8.0 Hz, 1H), 3.72 (s, 3H), 2.78 (s, 3H), 2.10 (s, 3H) MS m/z 430.2 (M + 1) | 0.141 | 9 |
| D10 | 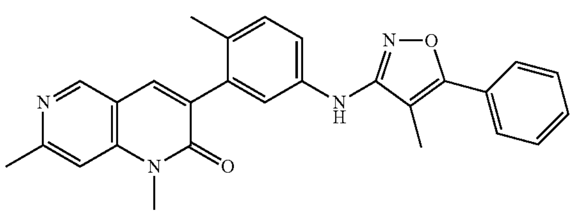 | MS m/z 437.2 (M + 1) | 0.339 | 10 |
| D11 | 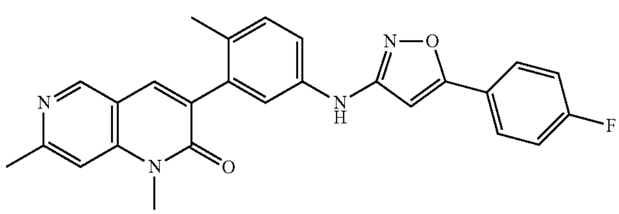 | $^1$H NMR (400 MHz, DMSO) δ 9.25 (s, 1H), 8.81 (s, 1H), 7.95 (s, 1H), 7.90 (m, 2H), 7.43 (s, 1H), 7.38 (m, 4H), 7.19 (d, J = 8.4 Hz, 1H), 6.58 (s, 1H), 2.61 (s, 3H), 2.51 (s, 3H), 2.08 (s, 3H) MS m/z 441.1 (M + 1) | 0.082 | 8 |
| D12 | 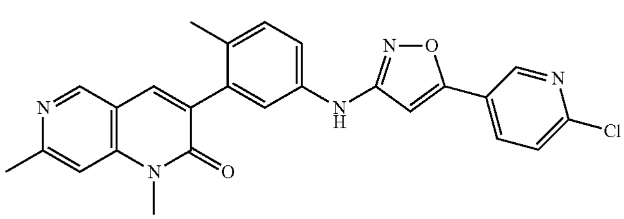 | MS m/z 458.1, 460.1 (M + 1) | 0.198 | 8 |
| D13 | 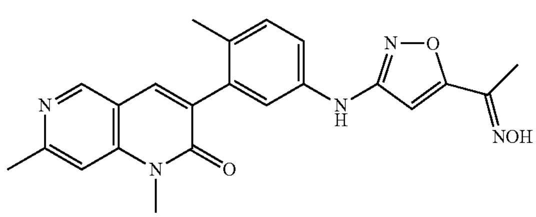 | MS m/z 404.1 (M + 1) | 0.476 | 10 |

TABLE 1-continued

| Compound Number | Structure | ¹H NMR 400 MHz and/or MS m/z | IC$_{50}$ Mo7e (μM) | Synthesis Method |
|---|---|---|---|---|
| D14 | 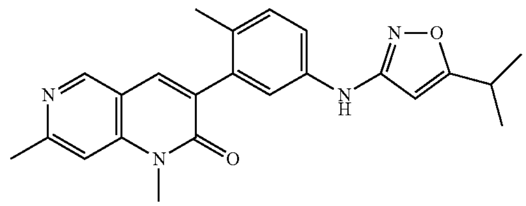 | ¹H NMR (400 MHz, DMSO) δ 9.06 (s, 1H), 9.00 (s, 1H), 8.01 (s, 1H), 7.70 (s, 1H), 7.36 (d, J = 2.0 Hz, 1H), 7.30 (dd, J = 2.0, 8.0 Hz, 1H), 7.18 (d, J = 8.4 Hz, 1H), 5.82 (s, 1H), 2.96 (m, 1H), 2.70 (s, 3H), 2.51 (s, 3H), 2.07 (s, 3H), 1.22 (d, J = 6.8 Hz, 6H) MS m/z 389.1 (M + 1) | 0.144 | 10 |
| E1 | 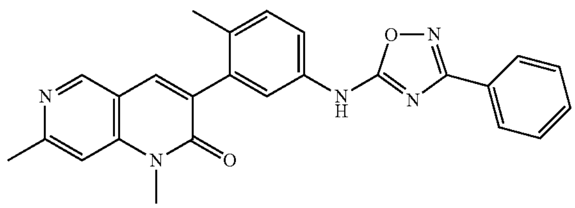 | MS m/z 424.4 (M + 1) | 0.423 | 11 |
| E2 | 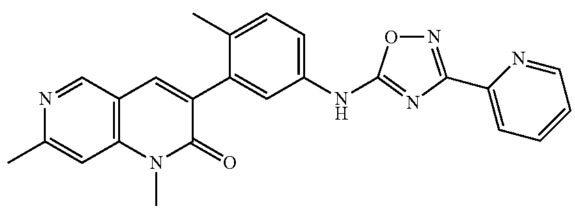 | ¹H NMR (400 MHz, d$_6$-DMSO) δ 11.17 (s, 1H), 9.05 (s, 1H), 8.72 (s, 1H), 8.08 (s, 1H), 8.01 (m, 2H), 7.75 (s, 1H), 7.66 (dd, J = 8, 2 Hz, 1H), 7.57 (s, 1H), 7.44 (d, J = 2 Hz, 1H), 7.35 (d, J = 8 Hz, 1H), 3.70 (s, 3H), 2.72 (s, 3H), 2.13 (s, 1H) MS m/z 425.3 (M + 1) | 0.256 | 11 |
| E3 | 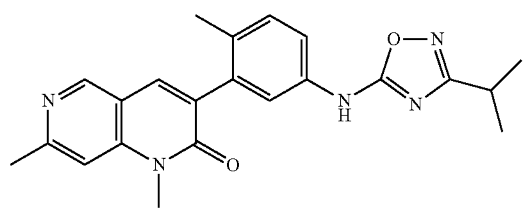 | ¹H NMR (400 MHz, d$_6$-DMSO) δ 10.84 (s, 1H), 9.05 (s, 1H), 8.05 (s, 1H), 7.77 (s, 1H), 7.55 (dd, J = 8, 2 Hz, 1H), 7.33 (d, J = 2 Hz, 1H), 7.30 (d, J = 8 Hz, 1H), 3.69 (s, 3H), 2.91 (m, 1H), 2.72 (s, 3H), 2.11 (s, 1H), 1.23, (d, J = 6.8 Hz, 6H) MS m/z 390.4 (M + 1) | 0.181 | 11 |
| F1 | 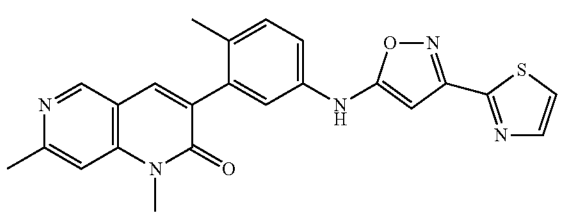 | ¹H NMR (400 MHz, d6-DMSO) δ 9.50 (s, 1H), 9.13 (s, 1H), (7.95-8.10 (m, 3H), 7.88 (s, 1H), 7.38 (s, 1H), 7.30 (d, J = 8.0 Hz, 1H), 7.18 (d, J = 8.0 Hz, 1H), 6.94 (s, 1H), 3.65 (s, 1H), 2.72 (s, 3H), 2.03 (s, 3H) MS m/z 430.1 (M + 1) | 0.111 | 12 |
| G1 | 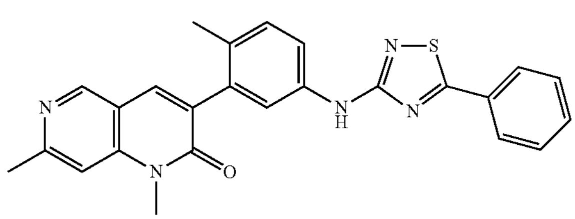 | MS m/z 440.3 (M + 1) | 0.733 | 13 |

TABLE 1-continued

| Compound Number | Structure | ¹H NMR 400 MHz and/or MS m/z | IC$_{50}$ Mo7e (µM) | Synthesis Method |
|---|---|---|---|---|
| H1 | 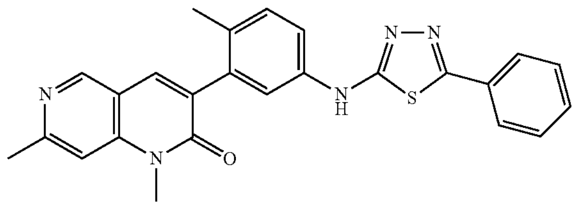 | MS m/z 440.1 (M + 1) | 0.552 | 14 |

Assays

Compounds of the present invention are assayed to measure their capacity to selectively inhibit the proliferation of wild type Ba/F3 cells and Ba/F3 cells transformed with Tel c-kit kinase and Tel PDGFR fused tyrosine kinases. In addition, compounds of the invention may selectively inhibit SCF dependent proliferation in Mo7e cells. Further, compounds are assayed to measure their capacity to inhibit Abl, ARG, BCR-Abl, BRK, EphB, Fms, Fyn, KDR, c-Kit, LCK, PDGF-R, b-Raf, c-Raf, SAPK2, Src, Tie2 and TrkB kinases.

Proliferation Assay: BaF3 Library—Bright Glo Readout Protocol

Compounds are tested for their ability to inhibit the proliferation of wt Ba/F3 cells and Ba/F3 cells transformed with Tel fused tyrosine kinases. Untransformed Ba/F3 cells are maintained in media containing recombinant IL3. Cells are plated into 384 well TC plates at 5,000 cells in 50 ul media per well and test compound at 0.06 nM to 10 µM is added. The cells are then incubated for 48 hours at 37° C., 5% CO$_2$. After incubating the cells, 25 µL of BRIGHT GLO® (Promega) is added to each well following manufacturer's instructions and the plates are read using Analyst GT—Luminescence mode—50000 integration time in RLU. IC$_{50}$ values are determined from a dose response curve.

Mo7e Assay

The compounds described herein are tested for inhibition of SCF dependent proliferation using Mo7e cells which endogenously express c-kit in a 96 well format. Two-fold serially diluted test compounds (Cmax=10 µM) are evaluated for their antiproliferative activity of Mo7e cells stimulated with human recombinant SCF. After 48 hours of incubation at 37° C., cell viability is measured by using a MTT colorimetric assay from Promega. IC$_{50}$ values for compounds of the invention are quoted in table 1, supra.

c-kit HTRF Protocol

An aliquot (5 µL) of a 2× concentration of c-kit enzyme mix 25 ng c-kit (5 ng/µL) and 2 µM of Biotin-EEEPQYEE-IPIYLELLP-NH$_2$ peptide in kinase buffer (20 mM Tris pH 7.5, 10 mM MgCl$_2$, 0.01% BSA, 0.1% Brij35, 1 mM DTT, 5% glycerol, 0.05 mM Na$_3$VO$_4$) is added to each well of a 384 proxiplate (Packard). Each well of the last row of the proxiplate has 5 µL of c-kit enzyme mix without c-kit to ascertain the background level. Compounds of the invention are added to each well and the plates are incubated for 30 minutes at room temperature. 2×ATP (40 µM) in kinase buffer (5 µL) is added to each well and the plate is incubated at room temperature form 3 hours. Detection mix (50% KF, 40% kinase buffer, 10% EDTA, 1:100 diluted Mab PT66-K (cat #61T66KLB) and 1:100 diluted Streptavidin-XL (cat #611SAXLB) (10 µL) is added to each well and the plates are further incubated for 1 to 2 hours at room temperature. The HTRF signal is then read on a detector.

Human TG/HA-VSMC Proliferation Assay

Human TG/HA-VSMC cells (ATCC) were resuspended in DMEM supplemented with 1% FBS and 30 ng/mL recombinant human PDGF-BB at 60,000 cells/mL. The cells were aliquoted into 384 well plates at 50 µL/well and incubated for 4 hours at 37° C. in a humidified incubator in the presence of 5% carbon dioxide. 0.5 µL of test compound diluted in DMSO was added to each well. The plates were returned to the incubator for a further 68 hours. 25 µL of CellTiter-Glo (Promega) was added to each well and the plates were incubated on the bench for 15 minutes. Luminescence was then read using a CLIPR CCD camera (Molecular Devices).

Compounds of Formula I, in free form or in pharmaceutically acceptable salt form, exhibit valuable pharmacological properties. Compounds of the invention show an IC$_{50}$ for c-kit and PDGFR of between 1×10$^{-5}$ and 1×10$^{-10}$ M, preferably less than 500 nM, more preferably less than 250 nM and 100 nM. Some of the compounds of the invention show increased selectivity for c-kit over PDGFR, for example, as shown in the table below:

| Structure | IC$_{50}$ Mo7e (µM) | IC$_{50}$ VSMC (µM) | ID |
|---|---|---|---|
| 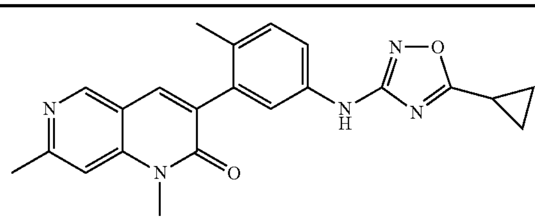 | 0.016 | 0.506 | A3 |

-continued

| Structure | IC$_{50}$ Mo7e (μM) | IC$_{50}$ VSMC (μM) | ID |
|---|---|---|---|
| 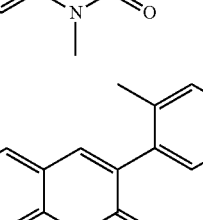 | 0.014 | 1.82 | A14 |
| 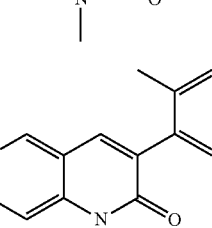 | 0.076 | 2.26 | B1 |
| 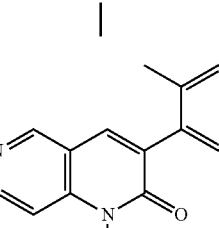 | 0.335 | 3.39 | C6 |
| 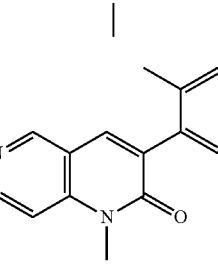 | 0.141 | 1.07 | D9 |
| 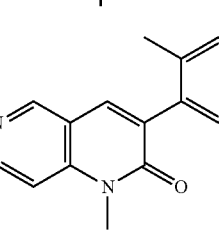 | 0.256 | 2.36 | E2 |
| 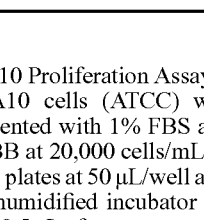 | 0.111 | 2.14 | F1 |

Rat A10 Proliferation Assay

Rat A10 cells (ATCC) were resuspended in DMEM supplemented with 1% FBS and 10 ng/mL recombinant rat PDGF-BB at 20,000 cells/mL. The cells were aliquoted into 384 well plates at 50 μL/well and incubated for 4 hours at 37° C. in a humidified incubator in the presence of 5% carbon dioxide. 0.5 μL of test compound diluted in DMSO was added to each well. The plates were returned to the incubator for a further 68 hours. 25 μL of CellTiter-Glo (Promega) was added to each well and the plates were incubated on the bench for 15 minutes. Luminescence was then read using a CLIPR CCD camera (Molecular Devices).

PDGFRα/β Lance Assay Protocol

An aliquot (2.5 μL) of a 2× concentration of PDGFRβ peptide and ATP mix (4 μM biotin-βA-βA-(3A-AEEEEYVFIEAKKK peptide, 20 μM ATP in assay buffer (20 mM Hepes, 54 mM MgCl$_2$, 0.01% BSA, 0.05% Tween-20, 1 mM DTT, 10% glycerol, 50 μM Na$_3$VO$_4$)) is added to each well of a 384 proxiplate (Packard). The plates are centrifuged and compounds of the invention (50 nL) are added to each well via a pintool dispenser. To each well is added (2.5 µL) of a 2× concentration of enzyme mix (PDGFRα at 4.5 ng/µL (cat #PV4117) or PDGFRβ at 1.5 ng/µL (cat #PV3591) in assay buffer) or assay buffer alone without PDGFRα/β enzyme. The plates are incubated for 1.5 hours at room temperature. Detection mix (5 µL; 50% 1M KF, 40% kinase buffer, 10% EDTA, 1:100 diluted Mab PT66-K (cat #61T66KLB) and 1:100 diluted Streptavidin-XL (cat #611SAXLB) is added to each well and the proxiplate is incubated for 1 hour at room temperature before reading the HTRF signal on a detector.

Ba/F3 FL FLT3 Proliferation Assay

The murine cell line used is the Ba/F3 murine pro-B cell line that over expresses full length FLT3 construct. These cells are maintained in RPMI 1640/10% fetal bovine serum (RPMI/FBS) supplemented with penicillin 50 µg/mL, streptomycin 50 µg/mL and L-glutamine 200 mM with the addition of murine recombinant IL3. Ba/F3 full length FLT3 cells undergo IL3 starvation for 16 hours and then plated into 384 well TC plates at 5,000 cells in 25 uL media per well and test compound at 0.06 nM to 10 µM is added. After the compound addition FLT3 ligand or IL3 for cytotoxicity control are added in 25 ul media per well at the appropriate concentrations. The cells are then incubated for 48 hours at 37° C., 5% $CO_2$. After incubating the cells, 25 µL of BRIGHT GLO® (Promega) is added to each well following manufacturer's instructions and the plates are read using Analyst GT—Luminescence mode—50000 integration time in RLU.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 µg/mL, streptomycin 50 µg/mL and L-glutamine 200 mM. Untransformed 32D cells are similarly maintained with the addition of 15% of WEHI conditioned medium as a source of IL3.

50 µL of a 32D or 32D-p210 cells suspension are plated in Greiner 384 well microplates (black) at a density of 5000 cells per well. 50 nL of test compound (1 mM in DMSO stock solution) is added to each well (STI571 is included as a positive control). The cells are incubated for 72 hours at 37° C., 5% $CO_2$. 10 µL of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 µL of two fold serial dilutions of the test compound ($C_{max}$ is 40 µM) are added to each well (STI571 is included as a positive control). After incubating the cells for 48 hours at 37° C., 5% $CO_2$, 15 µL of MTT (Promega) is added to each well and the cells are incubated for an additional 5 hours. The optical density at 570 nm is quantified spectrophotometrically and $IC_{50}$ values are determined from a dose response curve.

Effect on Cell Cycle Distribution 32D and 32D-p210 cells are plated into 6 well TC plates at $2.5 \times 10^6$ cells per well in 5 mL of medium and a test compound at 1 or 10 µM is added (STI571 is included as a control). The cells are then incubated for 24 or 48 hours at 37° C., 5% $CO_2$. 2 mL of cell suspension is washed with PBS, fixed in 70% EtOH for 1 hour and treated with PBS/EDTA/RNase A for 30 minutes. Propidium iodide (Cf=10 µg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture ELISA using a c-abl specific capture antibody and an antiphosphotyrosine antibody. 32D-p210 cells are plated in 96 well TC plates at $2 \times 10^5$ cells per well in 50 µL of medium. 50 µL of two fold serial dilutions of test compounds ($C_{max}$ is 10 µM) are added to each well (STI571 is included as a positive control). The cells are incubated for 90 minutes at 37° C., 5% $CO_2$. The cells are then treated for 1 hour on ice with 150 µL of lysis buffer (50 mM Tris-HCl, pH 7.4, 150 mM NaCl, 5 mM EDTA, 1 mM EGTA and 1% NP-40) containing protease and phosphatase inhibitors. 50 µL of cell lysate is added to 96 well optiplates previously coated with anti-abl specific antibody and blocked. The plates are incubated for 4 hours at 4° C. After washing with TBS-Tween 20 buffer, 50 µL of alkaline-phosphatase conjugated anti-phosphotyrosine antibody is added and the plate is further incubated overnight at 4° C. After washing with TBS-Tween 20 buffer, 90 µL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of BCR-Abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells are tested at 10, 3.3, 1.1 and 0.37 µM as described above (in media lacking IL3). The $IC_{50}$ values of the compounds lacking toxicity on the untransformed cells are determined from the dose response curves obtained as describe above.

FGFR3 (Enzymatic Assay)

Kinase activity assay with purified FGFR3 (Upstate) is carried out in a final volume of 10 µL containing 0.25 ng/mL of enzyme in kinase buffer (30 mM Tris-HCl pH 7.5, 15 mM $MgCl_2$, 4.5 mM $MnCl_2$, 15 nM $Na_3VO_4$ and 50 ng/mL BSA), and substrates (5 ng/mL biotin-poly-EY (Glu, Tyr) (CIS-US, Inc.) and 3 µM ATP). Two solutions are made: the first solution of 5 µL containing the FGFR3 enzyme in kinase buffer is first dispensed into 384-format ProxiPlate® (Perkin-Elmer) followed by adding 50 nL of compounds dissolved in DMSO. A 5 µL of second solution containing the substrate (poly-EY) and ATP in kinase buffer is then added to each wells. The reactions are incubated at room temperature for one hour, stopped by adding 10 µL of HTRF detection mixture, which contains 30 mM Tris-HCl pH7.5, 0.5 M KF, 50 mM ETDA, 0.2 mg/mL BSA, 15 ng/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 µM to 0.28 nM). In this assay, compounds of the invention have an $IC_{50}$ in the range of 10 nM to 2 µM.

FGFR3 (Cellular Assay)

Compounds of the invention are tested for their ability to inhibit transformed Ba/F3-TEL-FGFR3 cells proliferation, which is depended on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 µL culture medium. Compounds of the invention are dissolved and diluted in dimethylsufoxide (DMSO). Twelve points 1:3 serial dilutions are made into DMSO to create concentrations gradient ranging typically from 10 mM to 0.05 µM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After an additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

b-Raf—Enzymatic Assay

Compounds of the invention are tested for their ability to inhibit the activity of b-Raf. The assay is carried out in 384-well MaxiSorp plates (NUNC) with black walls and clear bottom. The substrate, IκBα is diluted in DPBS (1:750) and 15 µL is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 µL/well) for 3 hours at room temperature, washed 3 times with TBST and pat-dried. Assay buffer containing 20 µM ATP (10 µL) is added to each well followed by 100 nL or 500 nL of compound. B-Raf is diluted in the assay buffer (1 µL into 25 µL) and 10 µL of diluted b-Raf is added to each well (0.4 µg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 µL is added to each well. The plates are incubated at 4° C. overnight and washed 6 times with TBST. AP-conjugated goat-anti-mouse IgG is diluted in Superblock (1:1,500) and 15 µL is added to each well. Plates are incubated at room temperature for 1 hour and washed 6 times with TBST. 15 µL of fluorescent Attophos AP substrate (Promega) is added to each well and plates are incubated at room temperature for 15 minutes. Plates are read on Acquest or Analyst GT using a Fluorescence Intensity Program (Excitation 455 nm, Emission 580 nm).

b-Raf—Cellular Assay

Compounds of the invention are tested in A375 cells for their ability to inhibit phosphorylation of MEK. A375 cell line (ATCC) is derived from a human melanoma patient and it has a V599E mutation on the B-Raf gene. The levels of phosphorylated MEK are elevated due to the mutation of B-Raf. Sub-confluent to confluent A375 cells are incubated with compounds for 2 hours at 37° C. in serum free medium. Cells are then washed once with cold PBS and lysed with the lysis buffer containing 1% Triton X100. After centrifugation, the supernatants are subjected to SDS-PAGE, and then transferred to nitrocellulose membranes. The membranes are then subjected to western blotting with anti-phospho-MEK antibody (ser217/221) (Cell Signaling). The amount of phosphorylated MEK is monitored by the density of phospho-MEK bands on the nitrocellulose membranes.

Upstate KinaseProfiler™—Radio-Enzymatic Filter Binding Assay

Compounds of the invention are assessed for their ability to inhibit individual members of the kinase panel. The compounds are tested in duplicates at a final concentration of 10 µM following this generic protocol. Kinase buffer (2.5 µL, 10×-containing $MnCl_2$ when required), active kinase (0.001-0.01 Units; 2.5 µL), specific or Poly(Glu-4-Tyr) peptide (5-500 µM or 0.01 mg/ml) in kinase buffer and kinase buffer (50 µM; 5 µL) are mixed in an eppendorf on ice. A Mg/ATP mix (10 µL; 67.5 (or 33.75) mM $MgCl_2$, 450 (or 225) µM ATP and 1 µCi/µl [γ-$^{32}$P]-ATP (3000 Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu-4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

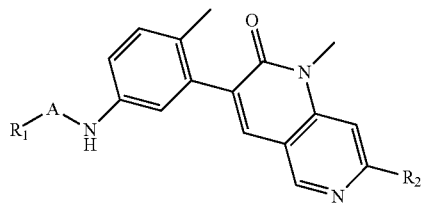

in which $R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, =N(OH), $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1NR_{3a}R_{3b}$, —$X_1C(O)R_{3a}$, —$X_1C(O)OR_{3a}$, —$X_1OR_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein $R_{3a}$ and $R_{3b}$ are independently selected from hydrogen and $C_{1-6}$alkyl;

$R_2$ is selected from methyl and ethyl;

A is 1,2,4-oxadiazolyl, 1,3,4-oxadiazolyl, 1,2,4-triazolyl, 1,2-oxazolyl, 1,2,4-thiadiazolyl or 1,3,4-thiadiazolyl; wherein the oxadiazolyl, triazolyl, isoxazolyl and thiadiazolyl of A can be optionally substituted with $C_{1-2}$alkyl;

or the pharmaceutically acceptable salts thereof.

2. The compound of claim 1, of Formula Ia:

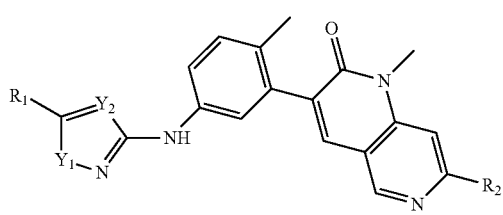

Ia in which $R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, =N(OH), $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, -$X_1$NR$_{3a}$R$_{3b}$, —$X_1$C(O)R$_{3a}$, —$X_1$C(O)OR$_{3a}$, —$X_1$OR$_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein R$_{3a}$ and R$_{3b}$ are independently selected from hydrogen and $C_{1-6}$alkyl;

$R_2$ is selected from methyl and ethyl;

$Y_1$ is selected from O, and S; and $Y_2$ is selected from N and CR$_4$; wherein R$_4$ is selected from hydrogen and $C_{1-2}$alkyl.

3. The compound of claim 2 in which $R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from hydroxy, halo, $C_{1-6}$alkoxy, benzoxy and =N(OH); wherein said cycloalkyl, heterocycloalkyl, aryl or heteroaryl of $R_1$ is optionally substituted with 1 to 3 radicals independently selected from halo, hydroxy, cyano, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1$NR$_{3a}$R$_{3b}$, —OR$_{3a}$, —C(O)R$_{3a}$ and $C_{3-10}$heteroaryl; wherein $X_1$ is selected from a bond and $C_{1-4}$alkylene; wherein R$_{3a}$ and R$_{3b}$ are independently selected from hydrogen and $C_{1-6}$alkyl; and $R_2$ is selected from methyl and ethyl.

4. The compound of claim 3 in which $R_1$ is selected from ethyl, t-butyl, t-butyl-methyl, isobutyl, propyl, isopropyl, neopentyl, sec-butyl, pentan-3-yl, 2-hydroxypropan-2-yl, 1-hydroxy-2-methylpropan-2-yl, 1-hydroxy-propan-2-yl, 1-hydroxy-2-methylpropyl, 1,1-difluoroethyl, 2-hydroxy-2-methylpropyl, 2-hydroxypropyl, ethoxy-methyl, 1-methoxyethyl, 1-phenoxyethyl, 1-(hydroxyimino)ethyl, pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl and cyclohexyl; wherein said pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl or cyclohexyl is optionally substituted with 1 to 3 radicals independently selected from chloro, fluoro, bromo, hydroxy, hydroxy-methyl, pyridinyl, cyano, methyl, methoxy, amino-methyl, methylcarbonyl, trifluoromethyl, difluoroethyl and trifluoromethoxy.

5. The compound of claim 4 selected from: 1,7-dimethyl-3-(2-methyl-5-(5-(pyridin-2-yl)-1,2,4-oxadiazol-3-ylamino)phenyl)-1,6-naphthyridin-2(1H)-one; 1,7-dimethyl-3-(2-methyl-5-(5-(6-methylpyridin-3-yl)-1,2,4-oxadiazol-3-ylamino)phenyl)-1,6-naphthyridin-2(1H)-one; 3-(5-{[5-(6-chloropyridin-3-yl)-1,2,4-oxadiazol-3-yl]amino}-2-methylphenyl)-1,7-dimethyl-1,2-dihydro-1,6-naphthyridin-2-one; 3-(5-{[5-(2,5-dimethylfuran-3-yl)-1,2,4-oxadiazol-3-yl]amino}-2-methylphenyl)-1,7-dimethyl-1,2-dihydro-1,6-naphthyridin-2-one; 3-{5-[(5-cyclopropyl-1,2,4-oxadiazol-3-yl)amino]-2-methylphenyl}-1,7-dimethyl-1,2-dihydro-1,6-naphthyridin-2-one; 1,7-dimethyl-3-[2-methyl-5-({5-[6-(trifluoromethyl)pyridin-3-yl]-1,2,4-oxadiazol-3-yl]amino}phenyl)-1,2-dihydro-1,6-naphthyridin-2-one; 3-{5-[(5-ethyl-1,2,4-oxadiazol-3-yl)amino]-2-methylphenyl}-1,7-dimethyl-1,2-dihydro-1,6-naphthyridin-2-one; 1,7-dimethyl-3-(2-methyl-5-{[5-(propan-2-yl)-1,2,4-oxadiazol-3-yl]amino}-phenyl)-1,2-dihydro-1,6-naphthyridin-2-one; 1,7-dimethyl-3-{2-methyl-5-[(5-phenyl-1,2,4-oxadiazol-3-yl)amino]phenyl}-1,2-dihydro-1,6-naphthyridin-2-one; 3-(5-{[5-(2-chlorophenyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(1,3-thiazol-2-yl)-1,2,4-oxadiazol-3-yl]amino}phenyl)-1,2-dihydro-1,6-naphthyridin-2-one; 1,7-dimethyl-3-(2-methyl-5-{[5-(pyridin-3-yl)-1,2,4-oxadiazol-3-yl]amino}phenyl)-1,2-dihydro-1,6-naphthyridin-2-one; 3-{5-[(5-cyclobutyl-1,2,4-oxadiazol-3-yl)amino]-2-methylphenyl}-1,7-dimethyl-1,2-dihydro-1,6-naphthyridin-2-one; 3-(5-{[5-(4-chlorophenyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(4-methylphenyl)-1,2,4-oxadiazol-3-yl]amino}phenyl)-1,2-dihydro-1,6-naphthyridin-2-one; 3-(5-{[5-(4-methoxyphenyl)-1,2,4-oxadiazol-3-yl]amino}-2-methylphenyl)-1,7-dimethyl-1,2-dihydro-1,6-naphthyridin-2-one; 3-{5-[(5-cyclopentyl-1,2,4-oxadiazol-3-yl)amino]-2-methylphenyl}-1,7-dimethyl-1,2-dihydro-1,6-naphthyridin-2-one; 1,7-dimethyl-3-(2-methyl-5-{[5-(2-methylphenyl)-1,2,4-oxadiazol-3-yl]amino}phenyl)-1,2-dihydro-1,6-naphthyridin-2-one; 1,7-dimethyl-3-(2-methyl-5-{[5-(3-methylphenyl)-1,2,4-oxadiazol-3-yl]amino}phenyl)-1,2-dihydro-1,6-naphthyridin-2-one; 3-{5-[(5-cyclohexyl-1,2,4-oxadiazol-3-yl)amino]-2-methylphenyl}-1,7-dimethyl-1,2-dihydro-1,6-naphthyridin-2-one; 3-(5-{[5-(2,2-dimethylpropyl)-1,2,4-oxadiazol-3-yl]amino}-2-methylphenyl)-1,7-dimethyl-1,2-dihydro-1,6-naphthyridin-2-one; 3-(5-{[5-(3-chlorophenyl)-

1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(1-methyl-1H-pyrrol-2-yl)-1,2,4-oxadiazol-3-yl]amino}phenyl)-1,2-dihydro-1,6-naphthyridin-2-one; 1,7-dimethyl-3-(2-methyl-5-{[5-(1-methyl-1H-imidazol-2-yl)-1,2,4-oxadiazol-3-yl]amino}phenyl)-1,2-dihydro-1,6-naphthyridin-2-one; 1,7-dimethyl-3-(2-methyl-5-{[5-(1-methylpyrrolidin-2-yl)-1,2,4-oxadiazol-3-yl]amino}phenyl)-1,2-dihydro-1,6-naphthyridin-2-one; 3-(5-{[5-(4-fluorophenyl)-1,2,4-oxadiazol-3-yl]amino}-2-methylphenyl)-1,7-dimethyl-1,2-dihydro-1,6-naphthyridin-2-one; 3-(5-{[5-(5-fluoropyridin-2-yl)-1,2,4-oxadiazol-3-yl]amino}-2-methylphenyl)-1,7-dimethyl-1,2-dihydro-1,6-naphthyridin-2-one; 3-(5-{[5-(5-chloropyridin-2-yl)-1,2,4-oxadiazol-3-yl]amino}-2-methylphenyl)-1,7-dimethyl-1,2-dihydro-1,6-naphthyridin-2-one; 3-[5-({5-[(2S)-butan-2-yl]-1,2,4-oxadiazol-3-yl}amino)-2-methylphenyl]-1,7-dimethyl-1,2-dihydro-1,6-naphthyridin-2-one; 1,7-dimethyl-3-{2-methyl-5-[(5-propyl-1,2,4-oxadiazol-3-yl)amino]phenyl}-1,2-dihydro-1,6-naphthyridin-2-one; 3-(5-{[5-(butan-2-yl)-1,2,4-oxadiazol-3-yl]amino}-2-methylphenyl)-1,7-dimethyl-1,2-dihydro-1,6-naphthyridin-2-one; 3-{5-[(5-tert-butyl-1,2,4-oxadiazol-3-yl)amino]-2-methylphenyl}-1,7-dimethyl-1,2-dihydro-1,6-naphthyridin-2-one; 1,7-dimethyl-3-(2-methyl-5-{[5-(pentan-3-yl)-1,2,4-oxadiazol-3-yl]amino}phenyl)-1,2-dihydro-1,6-naphthyridin-2-one; 3-(5-{[5-(2-hydroxypropan-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(oxan-4-yl)-1,2,4-oxadiazol-3-yl]amino}phenyl)-1,2-dihydro-1,6-naphthyridin-2-one; 1,7-dimethyl-3-(2-methyl-5-{[5-(1-methylcyclopropyl)-1,2,4-oxadiazol-3-yl]amino}phenyl)-1,2-dihydro-1,6-naphthyridin-2-one; 3-(5-{[5-(1-hydroxy-2-methylpropan-2-yl)-1,2,4-oxadiazol-3-yl]amino}-2-methylphenyl)-1,7-dimethyl-1,2-dihydro-1,6-naphthyridin-2-one; 3-(5-{[5-(4-hydroxyphenyl)-1,2,4-oxadiazol-3-yl]amino}-2-methylphenyl)-1,7-dimethyl-1,2-dihydro-1,6-naphthyridin-2-one; 4-(3-{[3-(1,7-dimethyl-2-oxo-1,2-dihydro-1,6-naphthyridin-3-yl)-4-methylphenyl]amino}-1,2,4-oxadiazol-5-yl)benzonitrile; 2-(3-{[3-(1,7-dimethyl-2-oxo-1,2-dihydro-1,6-naphthyridin-3-yl)-4-methylphenyl]amino}-1,2,4-oxadiazol-5-yl)benzonitrile; 3-(5-{[5-(3-hydroxyphenyl)-1,2,4-oxadiazol-3-yl]amino}-2-methylphenyl)-1,7-dimethyl-1,2-dihydro-1,6-naphthyridin-2-one; 3-(3-{[3-(1,7-dimethyl-2-oxo-1,2-dihydro-1,6-naphthyridin-3-yl)-4-methylphenyl]amino}-1,2,4-oxadiazol-5-yl)benzonitrile; 1,7-dimethyl-3-[2-methyl-5-({5-[4-(trifluoromethoxy)phenyl]-1,2,4-oxadiazol-3-yl}amino)phenyl]-1,2-dihydro-1,6-naphthyridin-2-one; 3-(5-{[5-(6-hydroxypyridin-2-yl)-1,2,4-oxadiazol-3-yl]amino}-2-methylphenyl)-1,7-dimethyl-1,2-dihydro-1,6-naphthyridin-2-one; 3-[5-({5-[4-(hydroxymethyl)phenyl]-1,2,4-oxadiazol-3-yl}amino)-2-methylphenyl]-1,7-dimethyl-1,2-dihydro-1,6-naphthyridin-2-one; 1,7-dimethyl-3-[2-methyl-5-({5-[2-(pyridin-3-yl)-1,3-thiazol-4-yl]-1,2,4-oxadiazol-3-yl}amino)phenyl]-1,2-dihydro-1,6-naphthyridin-2-one; 3-(5-{[5-(2,5-dimethyl-1,3-oxazol-4-yl)-1,2,4-oxadiazol-3-yl]amino}-2-methylphenyl)-1,7-dimethyl-1,2-dihydro-1,6-naphthyridin-2-one; 3-(5-{[5-(5-chloro-1H-indol-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(6-methylpyridin-2-yl)-1,2,4-oxadiazol-3-yl]amino}phenyl)-1,2-dihydro-1,6-naphthyridin-2-one; 3-(5-{[5-(2-chloro-6-methylpyridin-3-yl)-1,2,4-oxadiazol-3-yl]amino}-2-methylphenyl)-1,7-dimethyl-1,2-dihydro-1,6-naphthyridin-2-one; 3-(5-{[5-(6-chloropyridin-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(pyridin-4-yl)-1,2,4-oxadiazol-3-yl]amino}phenyl)-1,2-dihydro-1,6-naphthyridin-2-one; 1,7-dimethyl-3-(2-methyl-5-{[5-(6-methylpyridin-3-yl)-1,2,4-oxadiazol-3-yl]amino}phenyl)-1,2-dihydro-1,6-naphthyridin-2-one; 1,7-dimethyl-3-(2-methyl-5-{[5-(pyridin-2-yl)-1,2,4-oxadiazol-3-yl]amino}phenyl)-1,2-dihydro-1,6-naphthyridin-2-one; 1,7-dimethyl-3-(2-methyl-5-{[5-(5-methylpyridin-3-yl)-1,2,4-oxadiazol-3-yl]amino}phenyl)-1,2-dihydro-1,6-naphthyridin-2-one; 3-(5-{[5-(1,1-difluoroethyl)-1,2,4-oxadiazol-3-yl]amino}-2-methylphenyl)-1,7-dimethyl-1,2-dihydro-1,6-naphthyridin-2-one; 3-(5-{[5-(2-hydroxypropyl)-1,2,4-oxadiazol-3-yl]amino}-2-methylphenyl)-1,7-dimethyl-1,2-dihydro-1,6-naphthyridin-2-one; 3-(5-{[5-(2-hydroxy-2-methylpropyl)-1,2,4-oxadiazol-3-yl]amino}-2-methylphenyl)-1,7-dimethyl-1,2-dihydro-1,6-naphthyridin-2-one; 3-(5-{[5-(1-hydroxycyclopropyl)-1,2,4-oxadiazol-3-yl]amino}-2-methylphenyl)-1,7-dimethyl-1,2-dihydro-1,6-naphthyridin-2-one; 1,7-dimethyl-3-[2-methyl-5-({5-[1-(trifluoromethyl)cyclopropyl]-1,2,4-oxadiazol-3-yl}amino)phenyl]-1,2-dihydro-1,6-naphthyridin-2-one; 1,7-dimethyl-3-(2-methyl-5-{[5-(oxan-3-yl)-1,2,4-oxadiazol-3-yl]amino}phenyl)-1,2-dihydro-1,6-naphthyridin-2-one; 3-(5-{[5-(2,6-difluorophenyl)-1,2,4-oxadiazol-3-yl]amino}-2-methylphenyl)-1,7-dimethyl-1,2-dihydro-1,6-naphthyridin-2-one; 3-(5-{[5-(2,4-difluorophenyl)-1,2,4-oxadiazol-3-yl]amino}-2-methylphenyl)-1,7-dimethyl-1,2-dihydro-1,6-naphthyridin-2-one; 3-(5-{[5-(3,4-difluorophenyl)-1,2,4-oxadiazol-3-yl]amino}-2-methylphenyl)-1,7-dimethyl-1,2-dihydro-1,6-naphthyridin-2-one; 4-(3-{[3-(1,7-dimethyl-2-oxo-1,2-dihydro-1,6-naphthyridin-3-yl)-4-methylphenyl]amino}-1,2,4-oxadiazol-5-yl)-3-fluorobenzonitrile; 3-(5-{[5-(1-hydroxy-2-methylpropyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(3-methyloxetan-3-yl)-1,2,4-oxadiazol-3-yl]amino}phenyl)-1,2-dihydro-1,6-naphthyridin-2-one; 1,7-dimethyl-3-(2-methyl-5-{[5-(oxetan-2-yl)-1,2,4-oxadiazol-3-yl]amino}phenyl)-1,2-dihydro-1,6-naphthyridin-2-one; 3-(5-{[5-(1-hydroxypropan-2-yl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(2-methylpropyl)-1,2,4-oxadiazol-3-yl]amino}phenyl)-1,2-dihydro-1,6-naphthyridin-2-one; 3-[5-({5-[1-(hydroxymethyl)cyclopropyl]-1,2,4-oxadiazol-3-yl}amino)-2-methylphenyl]-1,7-dimethyl-1,2-dihydro-1,6-naphthyridin-2-one; 1,7-dimethyl-3-(2-methyl-5-{[5-(pyrazin-2-yl)-1,2,4-oxadiazol-3-yl]amino}phenyl)-1,2-dihydro-1,6-naphthyridin-2-one; 1,7-dimethyl-3-(2-methyl-5-{[5-(5-methylpyrazin-2-yl)-1,2,4-oxadiazol-3-yl]amino}phenyl)-1,2-dihydro-1,6-naphthyridin-2-one; 1,7-dimethyl-3-(2-methyl-5-{[5-(3-oxocyclobutyl)-1,2,4-oxadiazol-3-yl]

amino}phenyl)-1,2-dihydro-1,6-naphthyridin-2-one; 3-(5-{[5-(3-hydroxycyclopentyl)-1,2,4-oxadiazol-3-yl]amino}-2-methylphenyl)-1,7-dimethyl-1,2-dihydro-1,6-naphthyridin-2-one; 3-(5-{[5-(ethoxymethyl)-1,2,4-oxadiazol-3-yl]amino}-2-methylphenyl)-1,7-dimethyl-1,2-dihydro-1,6-naphthyridin-2-one; 1,7-dimethyl-3-[2-methyl-5-({5-[(2S)-oxolan-2-yl]-1,2,4-oxadiazol-3-yl}amino)phenyl]-1,2-dihydro-1,6-naphthyridin-2-one; 3-[5-({5-[(1S)-1-methoxyethyl]-1,2,4-oxadiazol-3-yl}amino)-2-methylphenyl]-1,7-dimethyl-1,2-dihydro-1,6-naphthyridin-2-one; 1,7-dimethyl-3-[2-methyl-5-({5-[(2S)-oxolan-2-yl]-1,2,4-oxadiazol-3-yl}amino)phenyl]-1,2-dihydro-1,6-naphthyridin-2-one; 1,7-dimethyl-3-(2-methyl-5-{[5-(oxolan-3-yl)-1,2,4-oxadiazol-3-yl]amino}phenyl)-1,2-dihydro-1,6-naphthyridin-2-one; 1,7-dimethyl-3-(2-methyl-5-{[5-(3-methylpyridin-2-yl)-1,2,4-oxadiazol-3-yl]amino}phenyl)-1,2-dihydro-1,6-naphthyridin-2-one; 3-(5-{[5-(2-methoxy-4-methylphenyl)-1,2,4-oxadiazol-3-yl]amino}-2-methylphenyl)-1,7-dimethyl-1,2-dihydro-1,6-naphthyridin-2-one; 3-(5-{[5-(2-chloro-4-fluorophenyl)-1,2,4-oxadiazol-3-yl]amino}-2-methylphenyl)-1,7-dimethyl-1,2-dihydro-1,6-naphthyridin-2-one; 3-(5-{[5-(2,4-dichlorophenyl)-1,2,4-oxadiazol-3-yl]amino}-2-methylphenyl)-1,7-dimethyl-1,2-dihydro-1,6-naphthyridin-2-one; 3-(5-{[5-(3-hydroxycyclobutyl)-1,2,4-oxadiazol-3-yl]amino}-2-methylphenyl)-1,7-dimethyl-1,2-dihydro-1,6-naphthyridin-2-one; 3-(5-{[5-(3-hydroxy-3-methylcyclobutyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(oxan-2-yl)-1,2,4-oxadiazol-3-yl]amino}phenyl)-1,2-dihydro-1,6-naphthyridin-2-one; 1,7-dimethyl-3-{2-methyl-5-[(5-phenyl-1,2,4-oxadiazol-3-yl)amino]phenyl}-6-oxido-2-oxo-1,2-dihydro-1,6-naphthyridin-6-ium; 3-(5-{[5-(6-methoxypyridin-3-yl)-1,2,4-oxadiazol-3-yl]amino}-2-methylphenyl)-1,7-dimethyl-1,2-dihydro-1,6-naphthyridin-2-one; 3-[5-({5-[6-(1,1-difluoroethyl)pyridin-3-yl]-1,2,4-oxadiazol-3-yl}amino)-2-methylphenyl]-1,7-dimethyl-1,2-dihydro-1,6-naphthyridin-2-one; 3-[5-({5-[4-(1,1-difluoroethyl)phenyl]-1,2,4-oxadiazol-3-yl}amino)-2-methylphenyl]-1,7-dimethyl-1,2-dihydro-1,6-naphthyridin-2-one; 3-[5-({5-[4-(aminomethyl)phenyl]-1,2,4-oxadiazol-3-yl}amino)-2-methylphenyl]-1,7-dimethyl-1,2-dihydro-1,6-naphthyridin-2-one; 3-(5-{[5-(2-fluoropyridin-3-yl)-1,2,4-oxadiazol-3-yl]amino}-2-methylphenyl)-1,7-dimethyl-1,2-dihydro-1,6-naphthyridin-2-one; 3-[5-({5-[(1R)-1-hydroxy-2-methylpropyl]-1,2,4-oxadiazol-3-yl}amino)-2-methylphenyl]-1,7-dimethyl-1,2-dihydro-1,6-naphthyridin-2-one; 3-[5-({5-[(1S)-1-hydroxy-2-methylpropyl]-1,2,4-oxadiazol-3-yl}amino)-2-methylphenyl]-1,7-dimethyl-1,2-dihydro-1,6-naphthyridin-2-one; 3-(5-{[5-(2-acetylphenyl)-1,2,4-oxadiazol-3-yl]amino}-2-methylphenyl)-1,7-dimethyl-1,2-dihydro-1,6-naphthyridin-2-one; 3-(5-{[5-(4-acetylphenyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(1-phenoxyethyl)-1,2,4-oxadiazol-3-yl]amino}phenyl)-1,2-dihydro-1,6-naphthyridin-2-one; 1,7-dimethyl-3-[2-methyl-5-({5-[(2R)-2-methyloxolan-2-yl]-1,2,4-oxadiazol-3-yl}amino)phenyl]-1,2-dihydro-1,6-naphthyridin-2-one; 3-(5-{[5-(2,3-dihydro-1-benzofuran-2-yl)-1,2,4-oxadiazol-3-yl]amino}-2-methylphenyl)-1,7-dimethyl-1,2-dihydro-1,6-naphthyridin-2-one; 1,7-dimethyl-3-[2-methyl-5-({5-[(2R)-oxan-2-yl]-1,2,4-oxadiazol-3-yl}amino)phenyl]-1,2-dihydro-1,6-naphthyridin-2-one; 1,7-dimethyl-3-[2-methyl-5-({5-[(2S)-oxan-2-yl]-1,2,4-oxadiazol-3-yl}amino)phenyl]-1,2-dihydro-1,6-naphthyridin-2-one; 3-(5-{[5-(3-hydroxy-3-methylcyclobutyl)-1,2,4-oxadiazol-3-yl]amino}-2-methylphenyl)-1,7-dimethyl-1,2-dihydro-1,6-naphthyridin-2-one; 1,7-dimethyl-3-(2-methyl-5-{[5-(5-methylpyridin-2-yl)-1,2,4-oxadiazol-3-yl]amino}phenyl)-1,2-dihydro-1,6-naphthyridin-2-one; 3-(5-{[5-(5-methoxypyridin-2-yl)-1,2,4-oxadiazol-3-yl]amino}-2-methylphenyl)-1,7-dimethyl-1,2-dihydro-1,6-naphthyridin-2-one; 7-ethyl-1-methyl-3-(2-methyl-5-{[5-(propan-2-yl)-1,2,4-oxadiazol-3-yl]amino}phenyl)-1,2-dihydro-1,6-naphthyridin-2-one; 7-ethyl-1-methyl-3-(2-methyl-5-{[5-(pyridin-2-yl)-1,2,4-oxadiazol-3-yl]amino}phenyl)-1,2-dihydro-1,6-naphthyridin-2-one; and 1,7-dimethyl-3-{2-methyl-5-[(5-phenyl-1,2,4-thiadiazol-3-yl)amino]phenyl}-1,2-dihydro-1,6-naphthyridin-2-one.

6. The compound of claim 1, of Formula Ib:

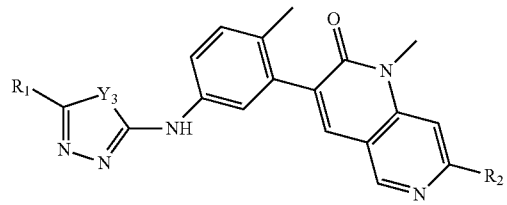

in which $R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1NR_{3a}R_{3b}$, —$X_1C(O)R_{3a}$, —$X_1C(O)OR_{3a}$, —$X_1OR_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein $R_{3a}$ and $R_{3b}$ are independently selected from hydrogen and $C_{1-6}$alkyl;

$R_2$ is selected from methyl and ethyl;

$Y_3$ is selected from O, S and $NR_4$; wherein $R_4$ is selected from hydrogen and $C_{1-2}$alkyl.

7. The compound of claim 6 in which $R_1$ is selected from ethyl, t-butyl, t-butyl-methyl, isobutyl, propyl, isopropyl, neopentyl, sec-butyl, pentan-3-yl, 2-hydroxypropan-2-yl, 1-hydroxy-2-methylpropan-2-yl, 1-hydroxy-propan-2-yl, 1-hydroxy-2-methylpropyl, 1,1-difluoroethyl, 2-hydroxy-2-methylpropyl, 2-hydroxypropyl, ethoxy-methyl, 1-methoxyethyl, 1-phenoxyethyl, 1-(hydroxyimino)ethyl, pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl and cyclohexyl; wherein said pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl or cyclohexyl is optionally substituted with 1 to 3 radicals independently selected from chloro, fluoro, bromo, hydroxy, hydroxy-methyl, pyridinyl, cyano, methyl, methoxy, amino-methyl, methylcarbonyl, trifluoromethyl, difluoroethyl and trifluoromethoxy.

8. The compound of claim 7 selected from: 1,7-dimethyl-3-(2-methyl-5-{[5-(4-methylphenyl)-1,3,4-oxadiazol-2-yl]amino}phenyl)-1,2-dihydro-1,6-naphthyridin-2-one; 3-(5-{[5-(4-methoxyphenyl)-1,3,4-oxadiazol-2-yl]amino}-2-methylphenyl)-1,7-dimethyl-1,2-dihydro-1,6-naphthyridin-2-one; 3-(5-{[5-(4-chlorophenyl)-1,3,4-oxadiazol-2-yl]amino}-2-methylphenyl)-1,7-dimethyl-1,2-dihydro-1,6-naphthyridin-2-one; 1,7-dimethyl-3-{2-methyl-5-[(5-phenyl-1,3,4-oxadiazol-2-yl)amino]phenyl}-1,2-dihydro-1,6-naphthyridin-2-one; 1,7-dimethyl-3-(2-methyl-5-{[5-(2-methylpropyl)-1,3,4-oxadiazol-2-yl]amino}phenyl)-1,2-dihydro-1,6-naphthyridin-2-one; 3-(5-{[5-(4-fluorophenyl)-1,3,4-oxadiazol-2-yl]amino}-2-methylphenyl)-1,7-dimethyl-1,2-dihydro-1,6-naphthyridin-2-one; 1,7-dimethyl-3-(2-methyl-5-{[5-(propan-2-yl)-1,3,4-oxadiazol-2-yl]amino}phenyl)-1,2-dihydro-1,6-naphthyridin-2-one; 3-{5-[(5-tert-butyl-1,3,4-oxadiazol-2-yl)amino]-2-methylphenyl}-1,7-dimethyl-1,2-dihydro-1,6-naphthyridin-2-one; 3-{5-[(5-cyclopropyl-1,3,4-oxadiazol-2-yl)amino]-2-methylphenyl}-1,7-dimethyl-1,2-dihydro-1,6-naphthyridin-2-one; 3-{5-[(5-cyclohexyl-1,3,4-oxadiazol-2-yl)amino]-2-methylphenyl}-1,7-dimethyl-1,2-dihydro-1,6-naphthyridin-2-one; 3-{5-[(5-cyclopentyl-4H-1,2,4-triazol-3-yl)amino]-2-methylphenyl}-1,7-dimethyl-1,2-dihydro-1,6-naphthyridin-2-one; 3-(5-{[5-(4-chlorophenyl)-4H-1,2,4-triazol-3-yl]amino}-2-methylphenyl)-1,7-dimethyl-1,2-dihydro-1,6-naphthyridin-2-one; 3-{5-[(5-cyclohexyl-4H-1,2,4-triazol-3-yl)amino]-2-methylphenyl}-1,7-dimethyl-1,2-dihydro-1,6-naphthyridin-2-one; 1,7-dimethyl-3-(2-methyl-5-{[5-(4-methylphenyl)-4H-1,2,4-triazol-3-yl]amino}phenyl)-1,2-dihydro-1,6-naphthyridin-2-one; 3-(5-{[5-(2,2-dimethylpropyl)-4H-1,2,4-triazol-3-yl]amino}-2-methylphenyl)-1,7-dimethyl-1,2-dihydro-1,6-naphthyridin-2-one; 1,7-dimethyl-3-{2-methyl-5-[(5-phenyl-4H-1,2,4-triazol-3-yl)amino]phenyl}-1,2-dihydro-1,6-naphthyridin-2-one; 3-(5-{[5-(3-chlorophenyl)-4H-1,2,4-triazol-3-yl]amino}-2-methylphenyl)-1,7-dimethyl-1,2-dihydro-1,6-naphthyridin-2-one; 3-{5-[(5-cyclobutyl-4H-1,2,4-triazol-3-yl)amino]-2-methylphenyl}-1,7-dimethyl-1,2-dihydro-1,6-naphthyridin-2-one; and 1,7-dimethyl-3-{2-methyl-5-[(5-phenyl-1,3,4-thiadiazol-2-yl)amino]phenyl}-1,2-dihydro-1,6-naphthyridin-2-one.

9. The compound of claim 1, of Formula Ic:

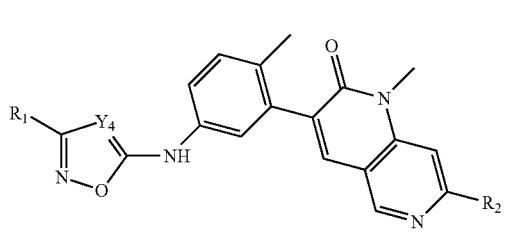

Ic in which $R_1$ is selected from halo, $C_{1-6}$alkyl, $C_{3-12}$cycloalkyl, $C_{3-8}$heterocycloalkyl, $C_{6-10}$aryl and $C_{3-10}$heteroaryl; wherein said $C_{1-6}$alkyl of $R_1$ is optionally substituted with 1 to 3 radicals independently selected from halo, hydroxy, cyano, nitro, $C_{1-4}$alkoxy and benzoxy; wherein said cycloalkyl, heterocycloalkyl, aryl or heteroaryl of $R_1$ is optionally substituted with 1 to 3 radicals independently selected from halo, hydroxy, cyano, nitro, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —$X_1NR_{3a}R_{3b}$, —$X_1C(O)R_{3a}$, —$X_1C(O)OR_{3a}$, —$X_1OR_{3a}$, $C_{3-12}$cycloalkyl, $C_{3-8}$heterocycloalkyl, $C_{6-10}$aryl and $C_{3-10}$heteroaryl; wherein $X_1$ is selected from a bond and $C_{1-4}$alkylene; wherein $R_{3a}$ and $R_{3b}$ are independently selected from hydrogen and $C_{1-6}$alkyl;

$R_2$ is selected from methyl and ethyl;

$Y_4$ is selected from $CR_4$ and $N_4$; wherein $R_4$ is selected from hydrogen and $C_{1-2}$alkyl.

10. The compound of claim 9 in which $R_1$ is selected from ethyl, t-butyl, t-butyl-methyl, isobutyl, propyl, isopropyl, neopentyl, sec-butyl, pentan-3-yl, 2-hydroxypropan-2-yl, 1-hydroxy-2-methylpropan-2-yl, 1-hydroxy-propan-2-yl, 1-hydroxy-2-methylpropyl, 1,1-difluoroethyl, 2-hydroxy-2-methylpropyl, 2-hydroxypropyl, ethoxy-methyl, 1-methoxyethyl, 1-phenoxyethyl, 1-(hydroxyimino)ethyl, pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl and cyclohexyl; wherein said pyridinyl, piperazinyl, furanyl, phenyl, thiazolyl, 2,3-dihydrobenzofuran-2-yl, 3-oxocyclobutyl, oxetan-3-yl, oxetan-2-yl, tetrahydro-2H-pyran-4-yl, tetrahydro-2H-pyran-3-yl, tetrahydro-2H-pyran-2-yl, tetrahydrofuranyl, 1H-indol-2-yl, cyclobutyl, cyclopropyl, cyclopentyl or cyclohexyl is optionally substituted with 1 to 3 radicals independently selected from chloro, fluoro, bromo, hydroxy, hydroxy-methyl, pyridinyl, cyano, methyl, methoxy, amino-methyl, methylcarbonyl, trifluoromethyl, difluoroethyl and trifluoromethoxy.

11. The compound of claim 10 selected from: 1,7-dimethyl-3-{2-methyl-5-[(3-phenyl-1,2,4-oxadiazol-5-yl)amino]phenyl}-1,2-dihydro-1,6-naphthyridin-2-one; 1,7-dimethyl-3-(2-methyl-5-{[3-(pyridin-2-yl)-1,2,4-oxadiazol-5-yl]amino}phenyl)-1,2-dihydro-1,6-naphthyridin-2-one; 1,7-dimethyl-3-(2-methyl-5-{[3-(propan-2-yl)-1,2,4-oxadiazol-5-yl]amino}phenyl)-1,2-dihydro-1,6-naphthyridin-2-one; and 1,7-dimethyl-3-(2-methyl-5-{[3-(1,3-thiazol-2-yl)-1,2-oxazol-5-yl]amino}phenyl)-1,2-dihydro-1,6-naphthyridin-2-one.

12. A pharmaceutical composition comprising a therapeutically effective amount of a compound of any one of claims 1-11 and a pharmaceutically acceptable excipient.

13. The pharmaceutical composition of claim 12, wherein the pharmaceutically acceptable excipient is suitable for parenteral administration.

14. The pharmaceutical composition of claim 13, wherein the pharmaceutically acceptable excipient is suitable for oral administration.

* * * * *